(12) United States Patent
Kuwata et al.

(10) Patent No.: US 10,939,890 B2
(45) Date of Patent: Mar. 9, 2021

(54) RADIOGRAPHIC IMAGING SYSTEM

(71) Applicant: KONICA MINOLTA, INC., Tokyo (JP)

(72) Inventors: Masahiro Kuwata, Machida (JP); Nobuyuki Miyake, Yokohama (JP); Koji Kashima, Higashiyamato (JP); Kohei Isogai, Kawasaki (JP); Kentaro Hara, Hino (JP); Hidetake Tezuka, Tachikawa (JP)

(73) Assignee: KONICA MINOLTA, INC., Tokyo (JP)

( * ) Notice: Subject to any disclaimer, the term of this patent is extended or adjusted under 35 U.S.C. 154(b) by 60 days.

(21) Appl. No.: 16/360,501

(22) Filed: Mar. 21, 2019

(65) Prior Publication Data

US 2019/0290237 A1 Sep. 26, 2019

(30) Foreign Application Priority Data

Mar. 23, 2018 (JP) .............................. JP2018-056477
Mar. 23, 2018 (JP) .............................. JP2018-056482

(51) Int. Cl.
*A61B 6/00* (2006.01)

(52) U.S. Cl.
CPC ............ *A61B 6/548* (2013.01); *A61B 6/4233* (2013.01); *A61B 6/461* (2013.01); *A61B 6/5211* (2013.01); *A61B 6/56* (2013.01)

(58) Field of Classification Search
CPC ........... A61B 6/548; A61B 6/56; A61B 6/461; A61B 6/5211; A61B 6/4233; A61B 6/4283; A61B 6/541; A61B 6/542; A61B 6/566; A61B 6/4494; A61B 6/44
See application file for complete search history.

(56) References Cited

U.S. PATENT DOCUMENTS

2013/0102245 A1* 4/2013 Ohguri .................. A61B 6/548
455/39

FOREIGN PATENT DOCUMENTS

| JP | 2006333898 A | 12/2006 |
| JP | 2009186439 A | 8/2009 |
| JP | 2010081960 A | 4/2010 |
| JP | 2011041866 A | 3/2011 |
| JP | 2013046819 A | 3/2013 |
| JP | 2014166578 A | 9/2014 |

* cited by examiner

*Primary Examiner* — Courtney D Thomas
(74) *Attorney, Agent, or Firm* — Cantor Colburn LLP

(57) ABSTRACT

A radiographic imaging system includes an irradiating apparatus, a first clock, a radiographic imaging apparatus, a second clock and a hardware processor. The irradiating apparatus generates radiation. The first clock keeps time and works with the irradiating apparatus. The radiographic imaging apparatus generates image data based on received radiation. The second clock keeps time and works with the radiographic imaging apparatus. The hardware processor (i) obtains a clock value of the first clock at a predetermined time point and a clock value of the second clock at the predetermined time point respectively as first clock information and second clock information, (ii) makes a determination as to whether a specific condition is met based on the obtained first clock information and the obtained second clock information, and (iii) in response to the specific condition being met, performs a specific output.

10 Claims, 40 Drawing Sheets

RADIOGRAPHIC IMAGING SYSTEM

CROSS REFERENCE TO RELATED APPLICATION

The present application claims priority under 35 U.S.C. § 119 to Japanese Application No. 2018-056477, filed Mar. 23, 2018 and Japanese Application No. 2018-056482, filed on Mar. 23, 2018, the entire content of which are incorporated herein by reference.

BACKGROUND

1. Technological Field

The present invention relates to a radiographic imaging system.

2. Description of the Related Art

Radiographic images have been taken with a radiographic imaging system that includes an irradiating apparatus for generating radiation and a radiographic imaging apparatus for generating image data of a radiographic image based on received radiation. In order to prevent the imaging apparatus from being irradiated over the charge accumulation time of the imaging apparatus, techniques to ensure the operation of the system have been used that involve sending and receiving an irradiation permission request signal and an irradiation permission signal between the irradiating apparatus and the imaging apparatus (see JP 2006-333898A, JP 2011-041866A, JP 2013-046819A and JP 2014-166578A).

In recent years, a dynamic behavior (movement) of a subject has been analyzed for diagnostic purposes by means of serial imaging in which the subject is radiographed at regular intervals to take frame images.

In a serial imaging process, an imaging apparatus repeats an imaging sequence at predetermined intervals, which mainly involves accumulating charges caused by irradiation in imaging elements, reading and transferring the accumulated charges and initializing the imaging elements.

Further, in a serial imaging process, the imaging sequence has to be repeated at a frame rate of as high as 15 frame/s or 30 frame/s so that the movement of a subject is completely captured. For example, even when a serial imaging process is performed at a relatively low frame rate of 15 frame/s, each imaging sequence for taking a frame image has to be completed within 66.6 ms. However, it takes approximately 50 ms for conventional imaging apparatuses as disclosed in the above-described publications to complete an imaging sequence.

Accordingly, the time that can be spent on irradiation is only approximately 15 ms.

However, conventional systems as disclosed in the above-described publications suffer from communication delay that occurs, for example, due to CSMA/CA specified in wireless communication standards for avoiding collision of packets, and it takes a long time to send or receive the irradiation permission request signal and the irradiation permission signal.

When communication delay occurs, for example, an irradiation cannot be completed within a period of time of accumulating charges in the imaging apparatus. This results in the decreased amount of radiation emitted to a frame compared to the amount of radiation in a normal condition in which no communication delay occurs. The decrease of radiation causes an overall decrease of the signal values of the resultant frame image.

An analysis of dynamic behavior of a subject using frame images, particularly an analysis that focuses on temporal difference of a subject, is greatly affected by such change in the amount of radiation.

That is, when signal values are decreased only in a certain frame, the difference of feature values between the certain frame and the previous frame thereof is greatly different from the difference of feature values between other two frames. The variation in the feature values may sometimes be erroneously recognized as an abnormality in some analysis.

Universally prevalent communication methods such as wireless LAN suffer from a delay of approximately 9 ms at the maximum. That is, a delay of 18 ms can occur in a process of sending an irradiation permission request signal and receiving a reply of an irradiation permission signal. In this case, radiation is not emitted at the timing of accumulating charges in the imaging elements, which results in a failure of serial imaging.

SUMMARY

It is an object of the present invention to provide a radiographic imaging system that includes an irradiating apparatus for generating radiation and a radiographic imaging apparatus for generating image data of a radiographic image based on the received radiation and that can take a suitable measure before the operation lag between the irradiating apparatus and the radiographic imaging apparatus becomes large enough to have an influence on diagnosis.

To achieve at least one of the abovementioned objects, according to an aspect of the present invention, a radiographic imaging system includes:

an irradiating apparatus which generates radiation;

a first clock which keeps time and which works with the irradiating apparatus;

a radiographic imaging apparatus which generates image data based on received radiation;

a second clock which keeps time and which works with the radiographic imaging apparatus; and a hardware processor, wherein the hardware processor (i) obtains a clock value of the first clock at a predetermined time point and a clock value of the second clock at the predetermined time point respectively as first clock information and second clock information, (ii) makes a determination as to whether a specific condition is met based on the obtained first clock information and the obtained second clock information, and (iii) in response to the specific condition being met, performs a specific output.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiment of the present invention will be described with reference to the drawings. However, the scope of the invention is not limited to the disclosed embodiments.

Configuration of Radiographic Imaging System

Figure 1:
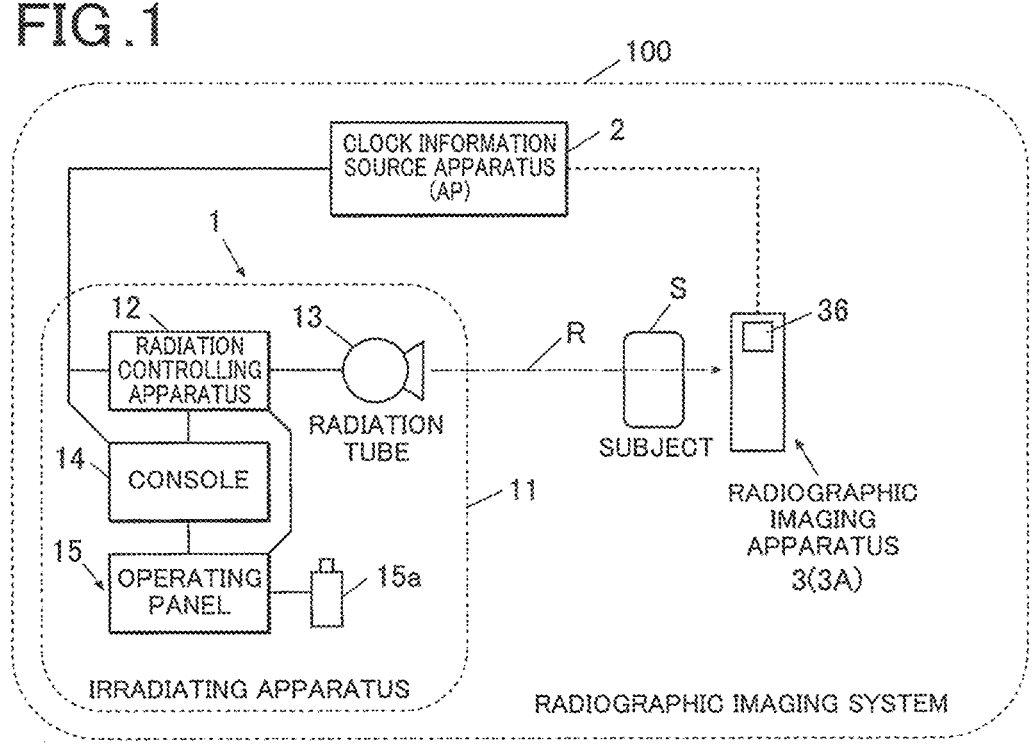
FIG. 1 is a block diagram of a radiographic imaging system according to an embodiment of the present invention, illustrating the configuration thereof.

First, an overview of a radiographic imaging system (hereinafter referred to as an imaging system 100) of the embodiment will be described. FIG. 1 is a block diagram of the imaging system 100, illustrating the schematic configuration thereof.

As illustrated in FIG. 1, the imaging system 100 of the embodiment includes an irradiating apparatus 1, an access point (hereinafter referred to as an AP 2) and at least one radiographic imaging apparatus (hereinafter referred to as an imaging apparatus 3).

The imaging system 100 is configured such that communication is possible between the irradiating apparatus 1 and the AP 2 and between the AP 2 and the imaging apparatus 3. That is, communication between the irradiating apparatus 1 and the imaging apparatus 3 is possible via the AP 2.

The imaging system 100 can communicate with a radiology information system (RIS), a picture archiving and communication system (PACS) and the like, which are not shown in the figures.

The irradiating apparatus 1 generates a radiation (X-ray radiation or the like) and emits the radiation R to a subject S and the imaging apparatus 3 disposed behind the subject S. The irradiating apparatus 1 includes a housing 11, a radiation controlling apparatus (hereinafter referred to as a controlling apparatus 12), a radiation tube (hereinafter referred to as a tube 13), a console 14, an operating panel 15 and the like.

Wired connection is established between the controlling apparatus 12 and the tube 13, between the controlling apparatus 12 and the console 14 and between the console 14 and the operating panel 15 so that communication is possible.

In response to a user operation to start an exposure, the controlling apparatus 12 applies a voltage to the tube 13 according to a preset irradiating condition.

The specific configuration of the controlling apparatus 12 will be described later.

When a voltage is applied from the controlling apparatus 12, the tube 13 generates the radiation R at a dose corresponding to the voltage for a period of time corresponding to the application time of the voltage.

That is, when the voltage is continuously applied from the controlling apparatus 12, the tube 13 continuously emits the radiation R. When the pulsed voltage is applied, the tube 13 emits the pulsed radiation R.

The console 14 is constituted by a PC, a portable terminal or a dedicated device.

The console 14 is capable of performing a variety of image processing to received image data according to need.

The console 14, which includes a display (not shown), can display a radiographic image based on image data.

With the console 14, it is possible to set an imaging mode.

In the embodiment, there are two imaging modes of a still imaging mode and serial imaging mode, and it is possible to select one of them.

In the still imaging mode, the radiation R is emitted only once for a duration specified as an irradiating condition in response to each exposure starting operation, and a single radiographic image is generated.

In the serial imaging mode, one or more pulses of the radiation R each having a duration specified as the irradiating condition is emitted in response to each exposure starting operation, and one or more radiographic images are generated.

With the console 14, it is possible to set the frame rate when the imaging mode is the serial imaging mode. The frame rate may be set according to a value input by a user or selected from options (e.g. 15 frames per second (hereinafter fps), 7.5 fps, 30 fps and the like).

The operating panel 15 includes a two-button exposure switch 15a.

The exposure switch 15a is connected to a main body of the operating panel 15 in a wired manner.

In response to a user operation on the exposure switch 15a, the operating panel 15 sends a radiographing start signal to the controlling apparatus 12 and the imaging apparatus 3. That is, in the embodiment, a user operation of pressing down the exposure switch 15a is one of the above-described exposure starting operations.

Figure 19:
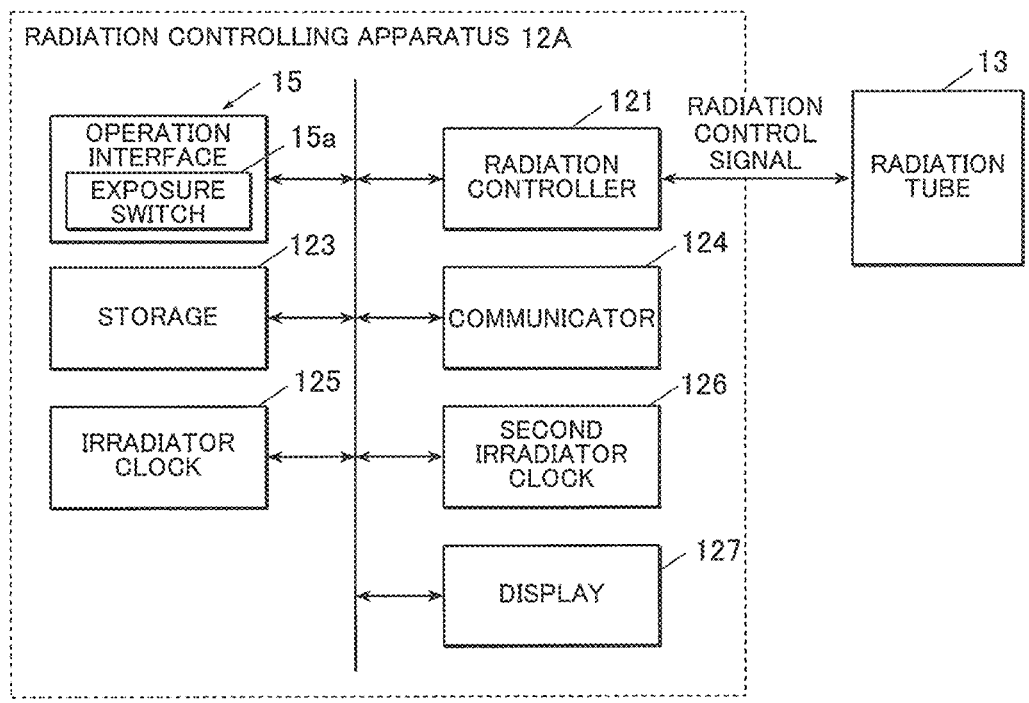
FIG. 19 is a block diagram of the radiation controlling apparatus of the radiographic imaging system in FIG. 10, illustrating the specific configuration thereof.

The operating panel 15 may be incorporated in the controlling apparatus 12 as an operation interface 15, which will be described later (as illustrated in FIG. 19).

The AP 2, which includes a communicator, relays communication between the irradiating apparatus 1 and the imaging apparatus 3.

The communicator, which includes an antenna and a connector, can perform both wired and wireless communications.

The communicator also sends beacons to the irradiating apparatus 1 and the imaging apparatus 3 repeatedly at predetermined intervals.

Instead of being provided separately from the irradiating apparatus 1 and the imaging apparatus 3, the AP 2 may be incorporated in the irradiating apparatus 1 or the imaging apparatus 3.

The imaging apparatus 3 receives the radiation R from the irradiating apparatus 1 to generate image data.

The details of the imaging apparatus 3 will be described later.

The imaging system 100 of the embodiment having the above-described configuration can take a radiographic image of the subject S by emitting the radiation R from the irradiating apparatus 1 to the subject S who is in front of the imaging apparatus 3.

When the still imaging mode is selected as the imaging mode on the console 14, a single still image is obtained. When the serial imaging mode is selected, a dynamic image composed of a series of images is obtained.

As used herein, a series of images obtained by serial imaging is referred to as a dynamic image, and each image constituting the dynamic image is referred to as a frame image.

Figure 17:
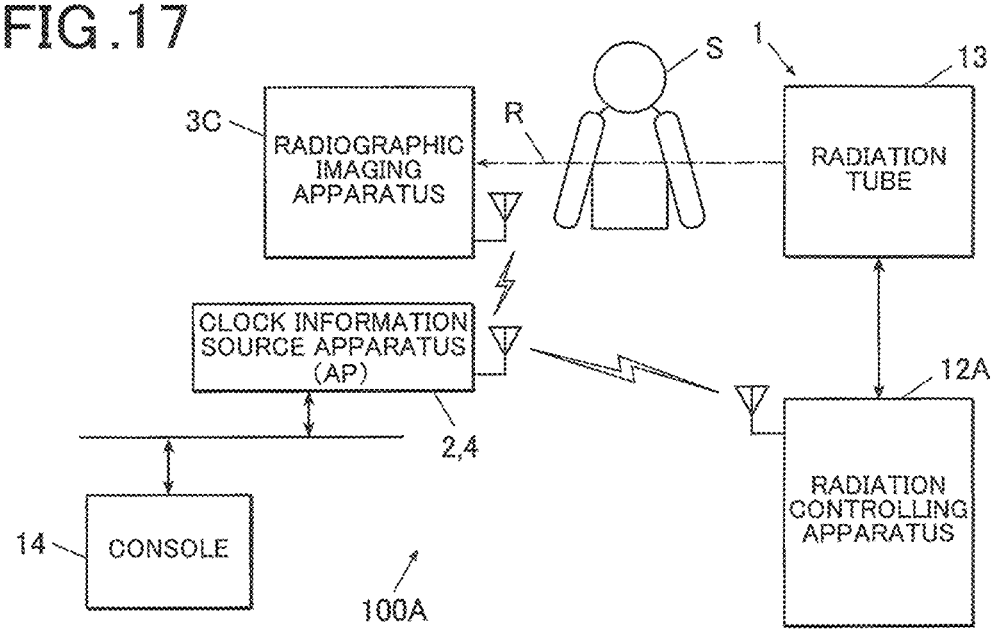
FIG. 17 is a block diagram of the radiographic imaging system according to a supplementary technique, illustrating the configuration thereof.

FIG. 1 illustrates an example configuration of the imaging system 100 in which the AP 2 communicates with the irradiating apparatus 1 in a wired manner while the AP 2 communicates with the imaging apparatus in a wireless manner. However, it is only necessary in the present invention that the AP 2 communicates with at least one of the irradiating apparatus 1 and the imaging apparatus 3 in a wireless manner. For example, as illustrated in FIG. 17, the AP 2 may communicate with both the irradiating apparatus 1 and the imaging apparatus 3 in a wireless manner. Alternatively, the AP 2 may communicate with the irradiating apparatus 1 in a wireless manner while the AP 2 may communicate with the imaging apparatus 3 in a wired manner.

The imaging system 100 of the embodiment having the above-described configuration can be installed in a radiography room of a hospital. Alternatively, the imaging system 100 can be used as a mobile system by configuring the irradiating apparatus 1 as a wheeled visiting wagon. When the system is mobile, it is possible to visit a subject S (Subject S) who cannot move around to take a radiographic image.

For example, when a radiographic table in a radiography room of a hospital is used to take a radiographic image, the imaging apparatus 3 disposed in the radiographic table may be connected by a cable for wired connection so that the imaging apparatus 3 can send and receive information to and from the irradiating apparatus 1 and receive an electric power supply.

For example, when the cable is used for wired connection with the imaging apparatus 3 as described above, a pulse signal or a timing signal may be included in signals for the wired connection. This allows synchronizing the irradiating apparatus 1 with the imaging apparatus 3 to take a radiographic image.

However, for example, even when an image is taken in a radiography room, it is sometimes necessary to radiograph a subject who is sifting on a wheel chair or laying on a bed. In such cases, the imaging apparatus 3 connected with a cable suffers from the following problems.

The cable distracts the user.

The cable may be detached to cause a communication failure.

The cable contacts with a subject, which causes hygienic concern.

Therefore, there is a need for radiography that does not use a cable for wired connection.

When a user visits a subject along with a visiting wagon, an image is taken at a ward where the subject is cared. In such cases, an image is taken at a bed on which the subject is laying, and it is necessary to put the radiographic imaging apparatus between the subject and the bed. Therefore, the problems (the cable distracts the user, the cable may be detached to cause communication failure, the cable contacts with a subject, which causes hygienic concern, etc.) are more serious than taking an image in a radiography room, and it has been desired to take an image without using a cable for wired connection.

In particular, since the CR, which is a conventional technique before radiographic imaging apparatuses with an FPD is developed, did not require a cable for wired connection, there is a need for radiography that does not use a cable for wired connection in order to achieve the same operability as the CR.

With the imaging system 100 of the embodiment, it is possible to develop a visiting wagon that satisfies the needs.

Configuration of Radiation Controlling Apparatus

Figure 2:
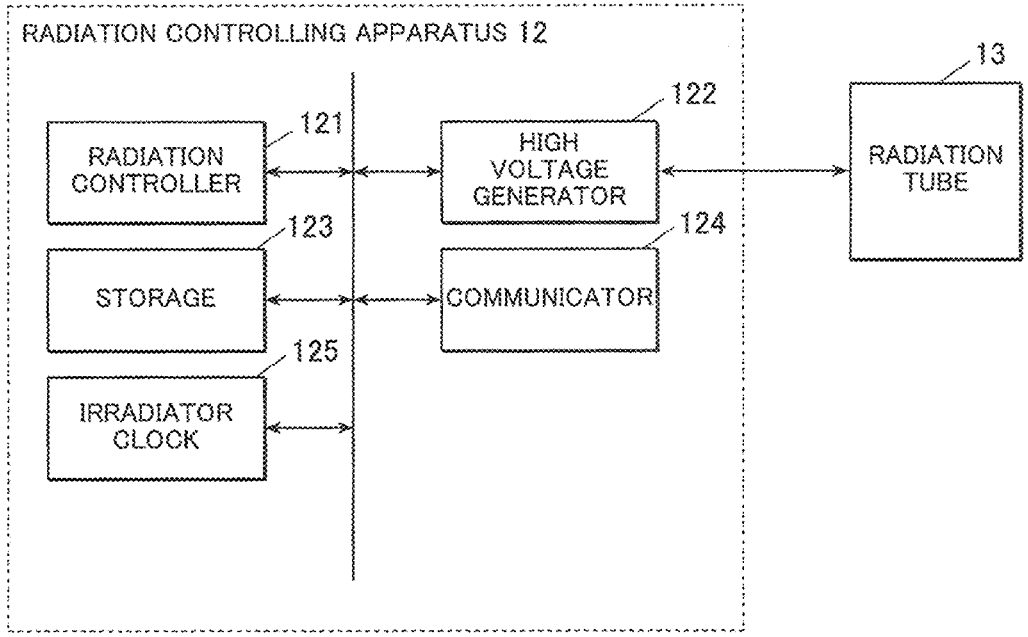
FIG. 2 is a block diagram of a radiation controlling apparatus of the radiographic imaging system in FIG. 1, illustrating the specific configuration thereof.

Next, a specific configuration of a controlling apparatus 12 of the irradiating apparatus 1 will be described. FIG. 2 is a block diagram of the controlling apparatus 12, illustrating the specific configuration thereof.

As illustrated in FIG. 2, the controlling apparatus 12 according to the embodiment includes a radiation controller 121, a high voltage generator 122, a storage 123, a communicator 124, an irradiator clock 125 and the like.

The radiation controller 121 can set radiographing conditions (conditions relating to the subject S such as a body part to be radiographed and the body shape, and conditions relating to irradiation such as a tube voltage, a tube current, an irradiation time and a current-time product) according to a control signal from the console 14 or the operating panel 15. In response to receiving a radiographing start signal from the exposure switch 15a, the radiation controller 121 sends a controlling signal to the high voltage generator 122 to start applying a voltage (irradiation).

In response to receiving the control signal from a radiation controller, the high voltage generator 122 applies a voltage to the tube 13 according to the preset irradiating conditions.

The storage 123 is constituted by a SRAM (Static RAM), an SDRAM (Synchoronous DRAM), a NAND flash memory, an HDD (Hard Disk Drive) and the like.

The communicator 124 includes an antenna and a connector for communication with external devices.

The communicator 124 can select between wired communication and wireless communication according to an external control signal. That is, when selecting wireless communication, the communicator 124 performs wireless communication by using the antenna. When selecting wired communication, the communicator 124 can send and receive information via a wired LAN or the like. To perform synchronization by wired communication, for example, a protocol such as NTP (Network Time Protocol) or the method specified in the international standard, the IEEE Std. 1588-2008 (hereinafter referred to as the IEEE1588) can be used.

The irradiator clock 125, which serves as a second clock of the present invention, starts a clocking operation to generate clock information when the apparatus is powered on or it receives a predetermined external control signal.

The irradiator clock 125 may output either timing information such as pulses at regular intervals or time information such as year, month, day, hour and minute and second and the number of counts that is counted up at regular intervals from a certain time point.

Instead of being incorporated in the controlling apparatus 12, the irradiator clock 125 may be provided as an external device with respect to the controlling apparatus 12.

In recent years, some LAN chips have such timer function as a default function, which is a timing synchronization function (hereinafter referred to as a TSF) specified in the communication standards of the IEEE 802.11. This type of a wireless LAN chip can be used as the irradiator clock 125.

In the embodiment, the high voltage generator 122 is incorporated in the controlling apparatus 12. This allows the user to use radiation without concern for the high voltage generator 122. As a result, it is possible to use radiation with the system configuration that is less likely to have a defect due to mismatch between components.

However, the high voltage generator 122 may not be incorporated in the controlling apparatus 12, but the high voltage generator 122 may be configured as an independent device from the controlling apparatus 12. This configuration allows the user to select a suitable device as the high voltage generator 122 independently from the controlling apparatus 12, i.e. improves the flexibility in selection of the components.

Configuration of Radiographic Imaging Apparatus

Figure 3:
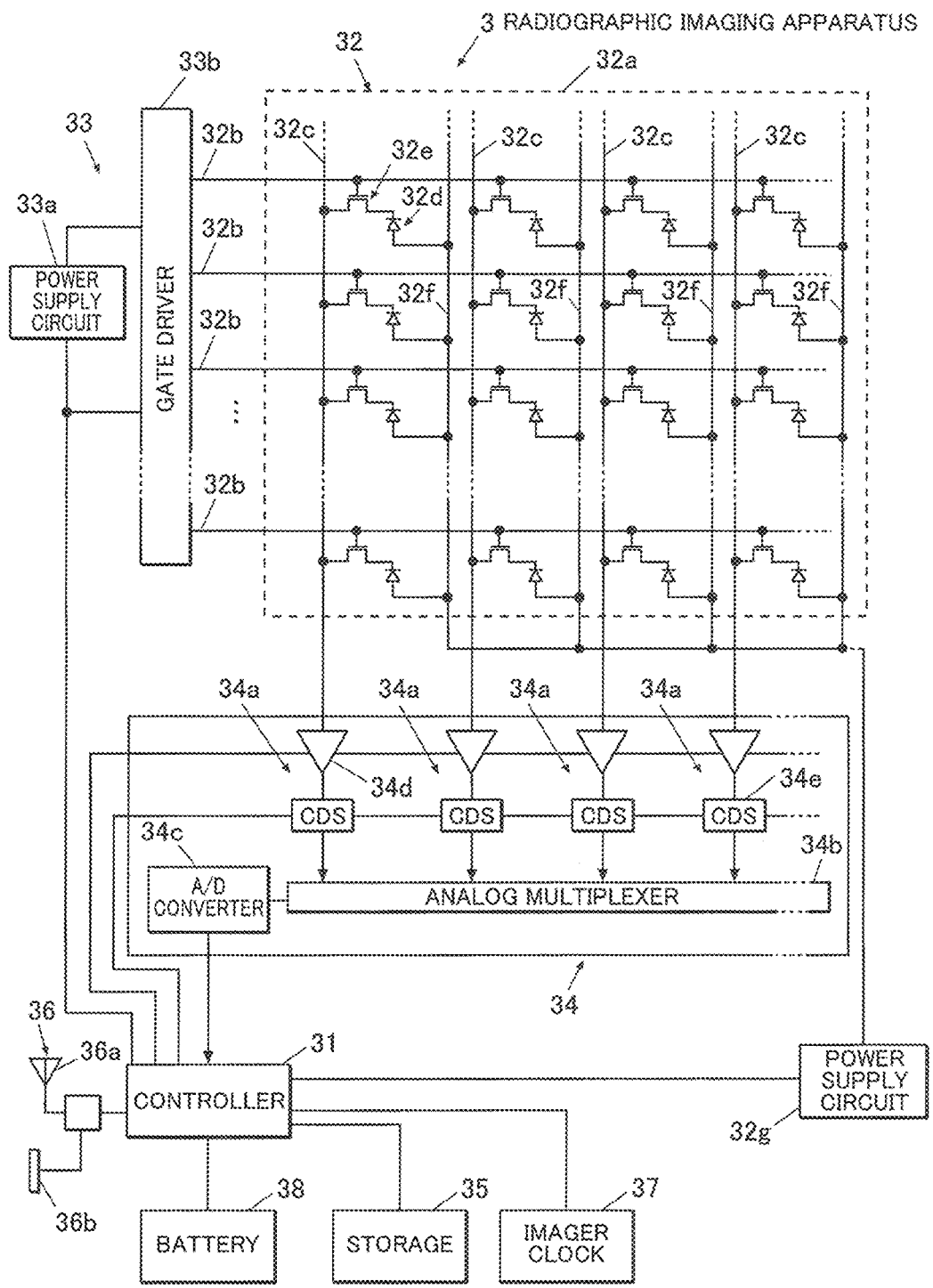
FIG. 3 is a block diagram of a radiographic imaging apparatus of the radiographic imaging system in FIG. 1, illustrating the specific configuration thereof.

Next, a specific configuration of the imaging apparatus 3 of the imaging system 100 will be described. FIG. 3 is a block diagram of the imaging apparatus 3, illustrating the specific configuration thereof.

In the embodiment, the imaging apparatus 3 is a so-called indirect imaging apparatus which obtains electric signals by converting the radiation R to an electromagnetic wave of a different wavelength such as visible light. However, the present invention is not limited thereto, and the imaging apparatus 3 may be a so-called direct imaging apparatus that directly converts the radiation R to electric signals with detecting elements.

Further, the other configurations of the imaging apparatus 3 is not limited to the example in FIG. 3, and the imaging apparatus 3 may have any configuration that can generate image data of a radiographic image.

As illustrated in FIG. 3, the imaging apparatus 3 of the embodiment includes an imaging controller 31, a radiation detector 32, a scanner driver 33, a reader 34, a storage 35, a communicator 36, an imager clock 37 and the like as well as a housing and a scintillator (not shown). A battery 38 supplies electric power to the components 31 to 37.

On the housing, a power switch, a selector switch, an indicator, a connector 36 of the communicator 36 (described later) and the like (not shown) are disposed.

When the Scintillator receives the radiation R, it emits an electromagnetic wave of a longer wavelength than the radiation R such as visible light.

The imaging controller 31 includes a computer with a CPU (Central Processing Unit), a ROM (Read Only Memory), a RAM (Random Access Memory), an input/output interface and the like connected to each other via a bus, a FPGA (Field Programmable Gate Array) and the like, which are not shown in the figure.

The imaging controller 31 may be constituted by a dedicated controller circuit.

The radiation detector 32 generates charges when it receives the radiation R. The radiation detector 32 includes a substrate 32a, a scanning lines 32b, signal lines 32c, radiation detecting elements 32d, switching elements 32e, bias lines 32f, a power supply circuit 32g and the like.

The substrate 32a, which is formed in a plate shape, is disposed opposite and parallel to the scintillator.

The scanning lines 32b extend parallel to each other at predetermined intervals.

The signal lines 32c extend parallel to each other at predetermined intervals, which extend perpendicular to the scanning lines 32b but are not electrically connected to the scanning lines.

That is, the scanning lines 32b and the signal lines 32 are disposed in a grid pattern.

The radiation detecting elements 32d generate electric signals (currents, charges) according to the dose of radiation emitted to the radiation detecting elements (or the amount of electromagnetic wave converted by the scintillator. The radiation detecting elements 32d are constituted by photodiodes or phototransistors.

The radiation detecting elements 32d are disposed on the surface of the substrate 32a respectively in the areas segmented by the scanning lines 32b and the signal lines 32c. That is, the radiation detecting elements 32d are arranged in a matrix. Accordingly, each of the radiation detecting elements 32d is opposed to the scintillator.

One terminal of each radiation detecting element 32d is connected to a drain terminal of each switching element 32e, and the other terminal is connected to a bias line.

As with the radiation detecting elements 32d, the switching elements 32e are disposed in the respective areas segmented by the scanning lines 32b and the signal lines 32c.

A gate electrode, a source electrode and a drain electrode of each switching element 32e are connected respectively to an adjacent scanning line 32b, an adjacent signal line 32 and one terminal of a radiation detecting element 32d disposed in the same area.

The bias lines 32f are connected to the other terminal of each radiation detecting element 32d.

The power supply circuit 32g generates a reverse bias voltage and applies it to the radiation detecting elements through the bias lines 32f.

The scanning driver 33 includes a power supply circuit 33a, a gate driver 33b and the like.

The power supply circuit 33a generates an on-voltage and an off-voltage, which are different from each other, and supplies them to the gate driver 33b.

The gate driver 33b switches the voltage to be applied to the scanning lines 32 between the on-voltage and the off-voltage.

The reader 34 includes reader circuits 34a, an analog multiplexer 34b, an A/D converter 34c and the like.

The reader circuits 34a are connected respectively to the signal lines 32c of the radiation detector 32 to apply a reference voltage to the signal lines 32c.

Each of the reader circuits 34a includes an integrator circuit 34d, a correlated double sampling circuit (hereinafter referred to as a CDS circuit) 34e and the like.

The integrator circuit 34d integrates charges released to the corresponding signal line 32c and outputs a voltage corresponding to the integral of the charges to the CDS circuit 34e.

The CDS circuits 34e samples and holds an output voltage of the integrator circuit 34d before the on-voltage is applied (i.e. while the off-voltage is applied) to a scanning line 32b connected to radiation detecting elements 32d from which a signal is to be read, so as to output the difference of an output voltage of the integrator circuit 34d after the on-voltage is applied to the scanning line 32b to read a signal charge of the radiation detecting element and then the off-voltage is applied to the scanning line 32b.

The analog multiplexer 34b sequentially outputs differential signals from the CDS circuits 34e to the A/D converter 34c one by one.

The A/D converter 34c sequentially converts input image data composed of analog voltages to image data composed of digital values.

The storage 35 is constituted by an SRAM (Static RAM), an SDRAM (Synchronous DRAM), a NAND flash memory, an HDD (Hard Disk Drive) and the like.

The communicator 36 includes an antenna 36a and a connector 36b for communication with external devices.

The communicator 36 can select between wired communication and wireless communication according to an external control signal. That is, when selecting wireless communication, the communicator 36 performs wireless communication by using the antenna 36a. When selecting wired communication, the communicator 36 can send and receive information via a wired LAN or the like. To perform synchronization by wired communication, for example, a protocol such as NTP (Network Time Protocol) or the method specified in the IEEE 1588 can be used.

The imager clock 37, which serves as a second clock of the present invention, starts a clocking operation to generate clock information when the apparatus is powered on or it receives a predetermined control signal.

The imager clock 37 may output either timing information such as pulses at regular intervals, or time information such as year, month, day, hour, minute and second and the number of counts that is counted up at regular intervals from a certain time point.

Instead of being incorporated in the imaging apparatus 3, the imager clock 37 may be provided as an external device with respect to the imaging apparatus 3.

In recent years, some LAN chips have such timer function as a default function, which is a timing synchronization function (hereinafter referred to as a TSF) specified in the communication standards of the IEEE 802.11. Accordingly, this type of wireless LAN chip can be used as the imager clock 37.

When the power of the imaging apparatus 3 having the above-described configuration is turned on, the imaging apparatus 3 puts itself into one of an "initialized state", an "accumulating state" and a "reading and transferring state". The timing of switching the state will be described later.

In the "initialized state", the on-voltage is applied to each of the switching elements 32e so that charges generated in the radiation detecting elements 32d are not accumulated in the respective pixels (i.e. the charges are released to the signal lines 32c).

In the "accumulating state", the off-voltage is applied to each of the switching elements 32e so that charges generated in the radiation detecting elements 32d can be accumulated in the respective pixels (i.e. the charges are not released to the signal lines 32c).

In the "reading and transferring state", the on-voltage is applied to each of the switching elements 32e, and the reader 34 is driven to read image data from received charges so that the reader 34 can send the image data to the other devices.

Depending on the configuration of the elements and the apparatus, accumulated charges are cleared in the reading step. In such cases, "reading" and "initializing" are not distinguished from each other as separate steps, but "reading" and "initializing" are performed simultaneously as a single step.

Imaging Operation of Radiographic Imaging System

Figure 4:
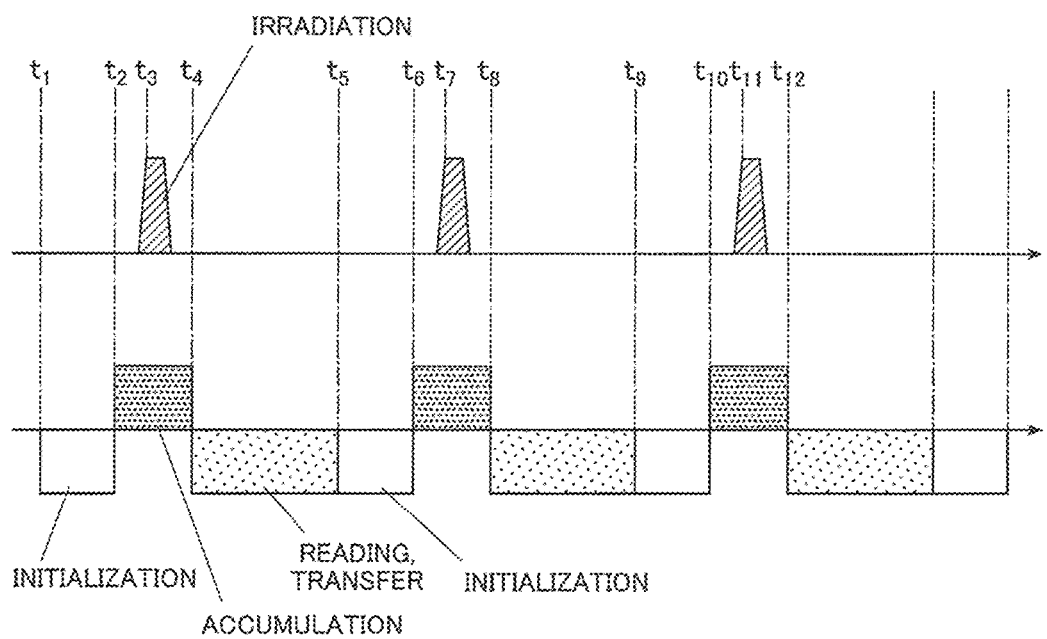
FIG. 4 is a timing chart of a basic operation of the radiographic imaging system in FIG. 1.
Figure 5:
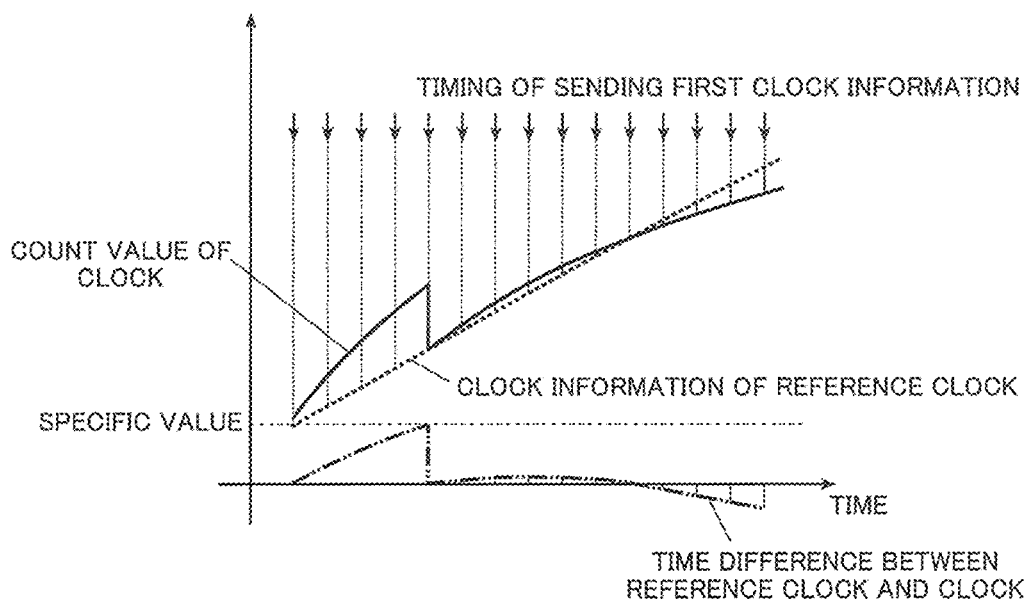
FIG. 5 illustrates clock information of clocks when the imaging system 100 in FIG. 1 is in operation.

Next, a basic imaging operation of the imaging system 100 will be described. FIG. 4 is a timing chart of an operation of the imaging system 100, and FIG. 5 illustrates the clock information of the clocks when the imaging system 100 is in operation.

First, when an action is performed which triggers the clocking operation of the irradiator clock 125 of the controlling apparatus 12 and the clocking operation of the imager clock 37 of the imaging apparatus 3 (e.g. when the apparatuses of the imaging system 100 is powered on), the irradiator clock 125 and the imager clock 37 individually start the respective clocking operations.

In this step, the irradiator clock 125 may start the clocking operation at a different timing from the imager clock 37. However, the clock information of one clock is synchronized with the clock information of the other clock based on the clock information of the other clock or clock information of a clock that is synchronized with the other clock.

Then, when the user presses down the exposure switch 15a of the irradiating apparatus 1, the irradiating apparatus 1 sends a radiographing start signal to the controlling apparatus 12 and the imaging apparatus 3.

When the clock information (time information) of the imager clock 37 reaches a first predetermined value (t1) (i.e. a first predetermined time (t1) has elapsed since the start of the clocking operation), the imaging apparatus 3 performs initialization by applying the on-voltage to the switching elements 32e to release dark charges accumulated in the pixels to the signal lines 32c.

Then, when the clock information of the imager clock 37 reaches a second predetermined value (t2) that is greater than the first predetermined value (i.e. a second predetermined time (t2) has elapsed since the start of the clocking operation), the imaging apparatus 3 applies the off-voltage to the scanning lines 32b so that charges generated by the radiation detecting elements 32d can be accumulated in the respective pixels. This charge accumulable state is maintained until the clock information of the imager clock 37 reaches a fourth predetermined value (t4) that is greater than the second predetermined value (i.e. a fourth predetermined time has elapsed from the start of the clocking operation).

When the clock information of the irradiator clock 125 of the controlling apparatus 12 reaches a third predetermined value (t3) that is greater than the second predetermined value but less than the fourth predetermined value (i.e. a third predetermined time has elapsed from the start of the timing operation), the irradiating apparatus 1 emits the radiation R to the subject S and the imaging apparatus 3 behind the subject S. That is, the irradiating apparatus 1 emits the radiation when the imaging apparatus 3 can accumulate charges (between t2 and t3).

When the imaging apparatus 3 receives the radiation R, it generates charges by the radiation detecting elements 32d of the radiation detector 32 and accumulate the charges in the respective pixels.

When the clock information of the imager clock 37 reaches the fourth predetermined value (t4) that is greater than the third predetermined value (i.e. a fourth predetermined time (t4) has elapsed since the start of the clocking operation), the imaging apparatus 3 applies the on-voltage to the TFTs 35 connected to the scanning lines 32b to release charges accumulated in the pixels to the signal lines 32c in the same way as the initialization. Then, the imaging apparatus 3 reads image data from the released charges by the reader 34.

Depending on the configuration of the radiation detecting elements of the imaging apparatus 3, initialization by releasing accumulated charges may be performed in the charge reading step.

When the imaging mode is the serial imaging mode, the irradiating apparatus 1 and the imaging apparatus 3 repeat the above-described series of steps based on the clock information of a TSF timer 22 and the imager clock 37 for the same times as the number of frame images to be taken.

Time Difference of Clocks

While the imaging system 100 is in operation as described above, for example, there may sometimes be a slight difference in clock rate between the irradiator clock 125 of the controlling apparatus 12 and the imager clock 37 of the imaging apparatus 3 due to the frequency error of an oscillator of the controlling apparatus 12 or the imaging apparatus 3 or the like. When a relatively lengthy imaging process such as serial imaging is performed in such cases, the time difference between the clock information of the irradiator clock 125 and the clock information of the imager clock 37 is incrementally increased, for example, as illustrated in FIG. 5. This causes a time lag between the operation timing of the irradiating apparatus 1 and the operation timing of the imaging apparatus 3.

To prevent this, the imaging system 100 of the embodiment takes a suitable measure before the time lag of the operation timing between the irradiating apparatus 1 and the imaging apparatus 3 becomes large enough to have an influence on diagnosis.

To check the length of the time lag, a first clock information as a standard and a second clock information as a target for comparison are required.

For example, the first clock information can be generated by the following methods.

Method for Generating First Clock Information 1

A first generating method uses the time information of the timing synchronization function (hereinafter referred to as the TSF) specified in the IEEE 802.11 communication standard as the first clock information.

The "TSF" is a function of synchronizing the time between an access point and devices when the devices communicate with each other in a wireless manner.

Specifically, the access point is provided with a free running clock (TSF timer) that counts up periodically (at 1 µs intervals) to send periodic beacons along with the information on the sent time (normally every 100 ms).

Further, each of the terminals are also provided with a clock that counts up periodically (at 1 µs intervals). When the terminals receive a beacon, it updates the time information of the own clock 125, 37 according to the time information included in the beacon and continues the counting up operation.

Figure 6:
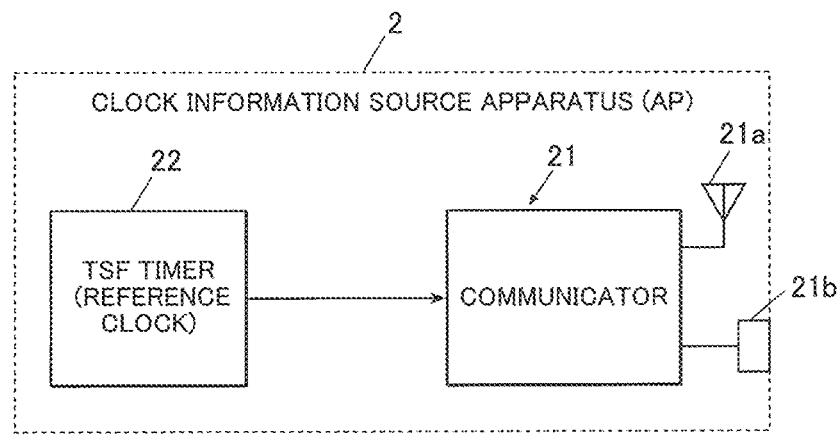
FIG. 6 a block diagram of an access point of the radiographic imaging system in FIG. 1, illustrating an example of the configuration thereof.

When the time information of the TSF is used as the first clock information, the AP 2 is provided with a TSF timer 22, and the communicator 21 of the AP 2 outputs the beacons including the time information to the controlling apparatus 12 and the imaging apparatus 3, for example, as illustrated in FIG. 6.

For example, the TSF timer 22 counts up from 0. When the time information reaches a predetermined maximum value, it resets the number to 0 and counts up from 0 again.

The TSF timer 22 may output the clock information that is generated independently from the controlling apparatus 12 or the imaging apparatus 3. Alternatively, the TSF timer 22 may output the clock information that is synchronized with the clock information of the controlling apparatus 12 or the imaging apparatus 3.

The time information of the TSF timer 22 included in each beacon, i.e. the time information of the TSF timer 22 at the time of sending each beacon, is used as the first clock information.

In this configuration, the TSF timer 22 serves as the first clock of the present invention.

Hereinafter, when the TSF is utilized as the first clock information, the AP 2 is referred to as a clock information source apparatus 2.

Method for Generating First Clock Information 2

A second generating method uses a dedicated apparatus that outputs the first clock information.

Figure 7:
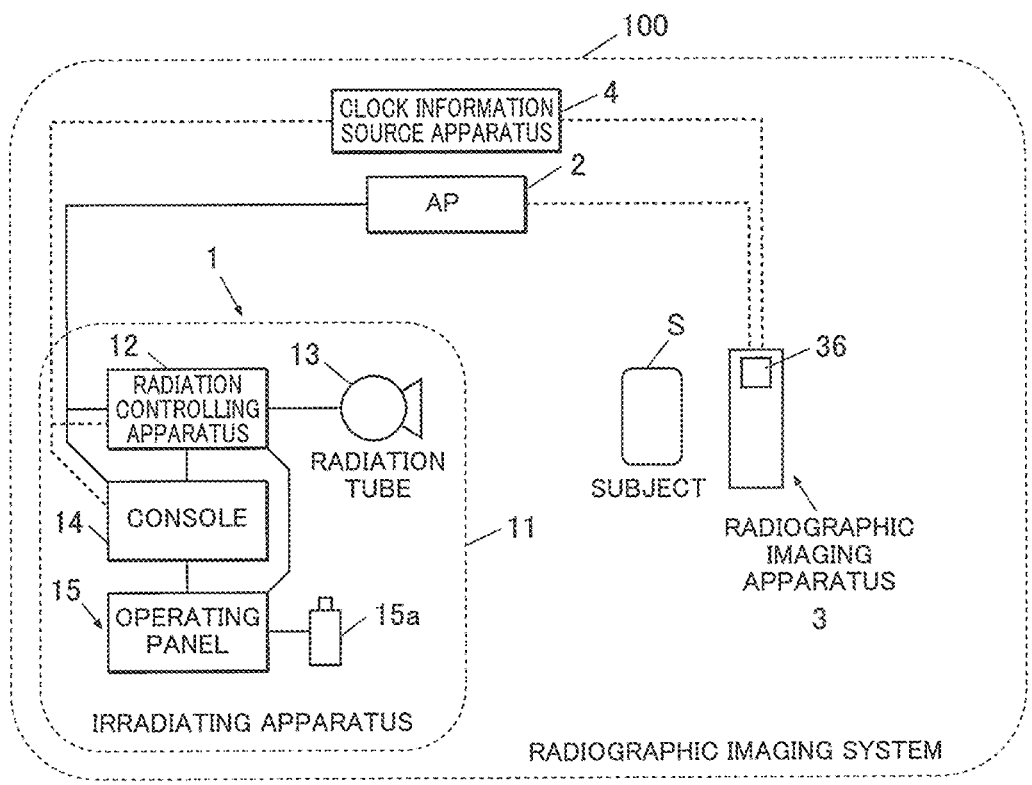
FIG. 7 is a block diagram of the radiographic imaging system according to the embodiment, illustrating another example of the configuration thereof.

Specifically, as illustrated in FIG. 7 for example, the system includes a clock information source apparatus 4 that includes a clock (not shown) and that can communicate clock information with the controlling apparatus 12 and the imaging apparatus 3.

The clock (not shown) is incorporated in the clock information source apparatus 4.

The clock of the clock information source apparatus 4 may output the clock information that is generated independently from the controlling apparatus 12 or the imaging apparatus 3. Alternatively, the TSF timer 22 may output the clock information that is synchronized with the clock information of the controlling apparatus 12 or the imaging apparatus 3.

The clock information source apparatus 4 may output either timing information such as pulses at regular intervals or time information such as year, month, day, hour, minute and second and a number that is counted up at regular intervals from a certain time point.

The clock information source apparatus 4 periodically sends the generated clock information as the first clock information.

In this configuration, the clock information source apparatus 4 serves as the first clock of the present invention.

In the following, the TSF timer 22 of the AP 2 or the clock (not shown) of the clock information source apparatus 4 is also referred to as a reference clock.

Obtainment of Second Clock Information

The controller of the controlling apparatus 12 or the imaging apparatus 3 that receives the first clock information from the clock information source apparatus 2, 4 obtains as the second clock information the clock information of the irradiator clock 125 or the imager clock 37 at the time of receiving (obtaining) the first clock information from the clock information source apparatus 2, 4. That is, in the present embodiment, the time of receiving the first clock information is the predetermined time point of the present invention.

Particularly in the present embodiment, the first clock information and the second clock information are obtained at two or more predetermined time points at least in a part of an imaging period. That is, in the present embodiment, the at least a part of the imaging period is the specific period of the present invention.

The specific period may be set to a desired length according to a user operation.

Figure 8:
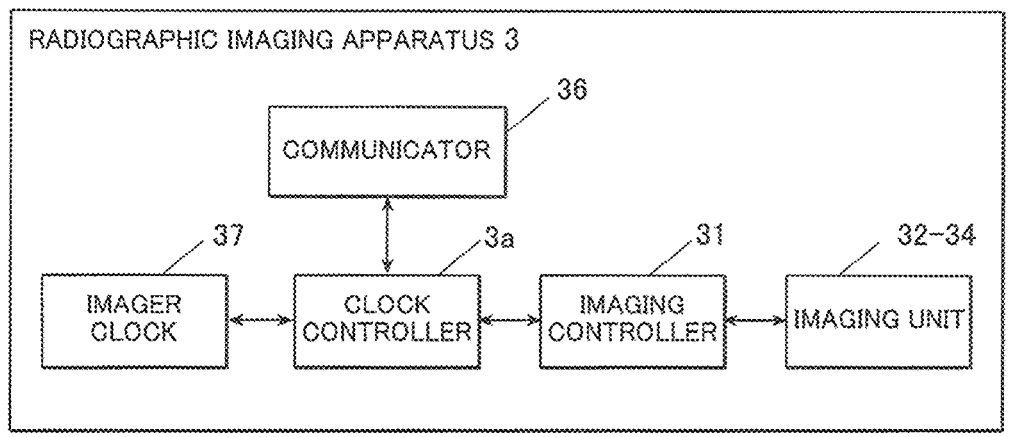
FIG. 8 is a block diagram of a radiographic imaging apparatus in FIG. 3, illustrating the functional configuration thereof.
Figure 9:
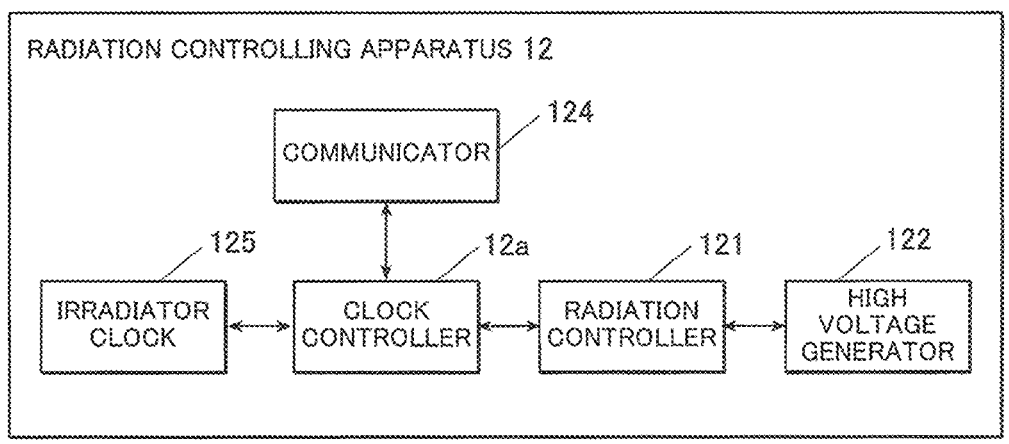
FIG. 9 is a block diagram of the radiation controlling apparatus in FIG. 2, illustrating the functional configuration thereof.

FIG. 8 illustrates a configuration of the imaging apparatus 3 for correcting the clock information of the own clock 37 and outputting it to the imaging controller 31, and FIG. 9 illustrates a configuration of the controlling apparatus 12 for correcting the clock information of the own clock 125 and outputting it to the radiation controller 125.

The imaging apparatus 3 or the controlling apparatus 12 that obtains the first clock information includes a clock controller 3a, 12a. The clock controller 3a, 12a is connected to the own clock 125, 37 to obtain the second clock information (time information or timing information) from the own clock 125, 37.

Further, the clock controller 3a, 12a is connected to the own communicator 124, 36 so as to be able to obtain the first clock information (time information or timing information) from the clock information source apparatus 2, 4.

The clock controller 3a, 12a may be constituted by a dedicated semiconductor, a circuit board or an apparatus or may be incorporated in a general-purpose processor (including the radiation controller 121 or the imaging controller 31) such as a CPU or a FPGA as one of the functions thereof.

In the clock controller 3a, 12a, setting information on the timing information or the time information of the clock information source apparatus 2, 4 may be previously stored.

In the configuration in which the clock information source apparatus 2, 4 outputs timing information as the first clock information, when the interval of outputting the timing information (pulses or the like) from the clock information source apparatus 2, 4 is set to, for example, x seconds, the interval of obtaining the external first clock information can be set to x seconds.

In the configuration in which the clock information source apparatus 2, 4 outputs time information as the first clock information, when the interval of outputting the time information (time, the number of counts that is counted up by the clock information source apparatus 4 from a certain time point, etc.) from the clock information source apparatus 2, 4 is set to x seconds, the interval of obtaining the external clock information can be set to x seconds.

In particular, when the time information is a count-up value counted by the clock information source apparatus 4, the clock controller 3*a*, 12*a* can obtain the counting interval of the clock information source apparatus 4 and store it. For example, when the counting frequency of the clock information source apparatus 2, 4 is y Hz, the clock controller 3*a*, 12*a* can previously obtain a counting interval of 1/y seconds and store it.

Combination of Time Lag Checking Methods

As described above, in the present embodiment, the first clock information generated by the clock information source apparatus 2, 4 is either time information or timing information. Similarly, the second clock information obtained by the irradiator clock 125 or the imager clock 37 is either time information or timing information.

Accordingly, depending on the configuration, the first clock information and the second clock information may be compared by any one of the following four methods to check the time difference.

1. Comparison of timing information with timing information
2. Comparison of timing information with time information
3. Comparison of time information with timing information
4. Comparison of time information with time information In the following, each of the methods for checking the time difference between the first clock information and the second clock information will be described in detail.

Figure 10:
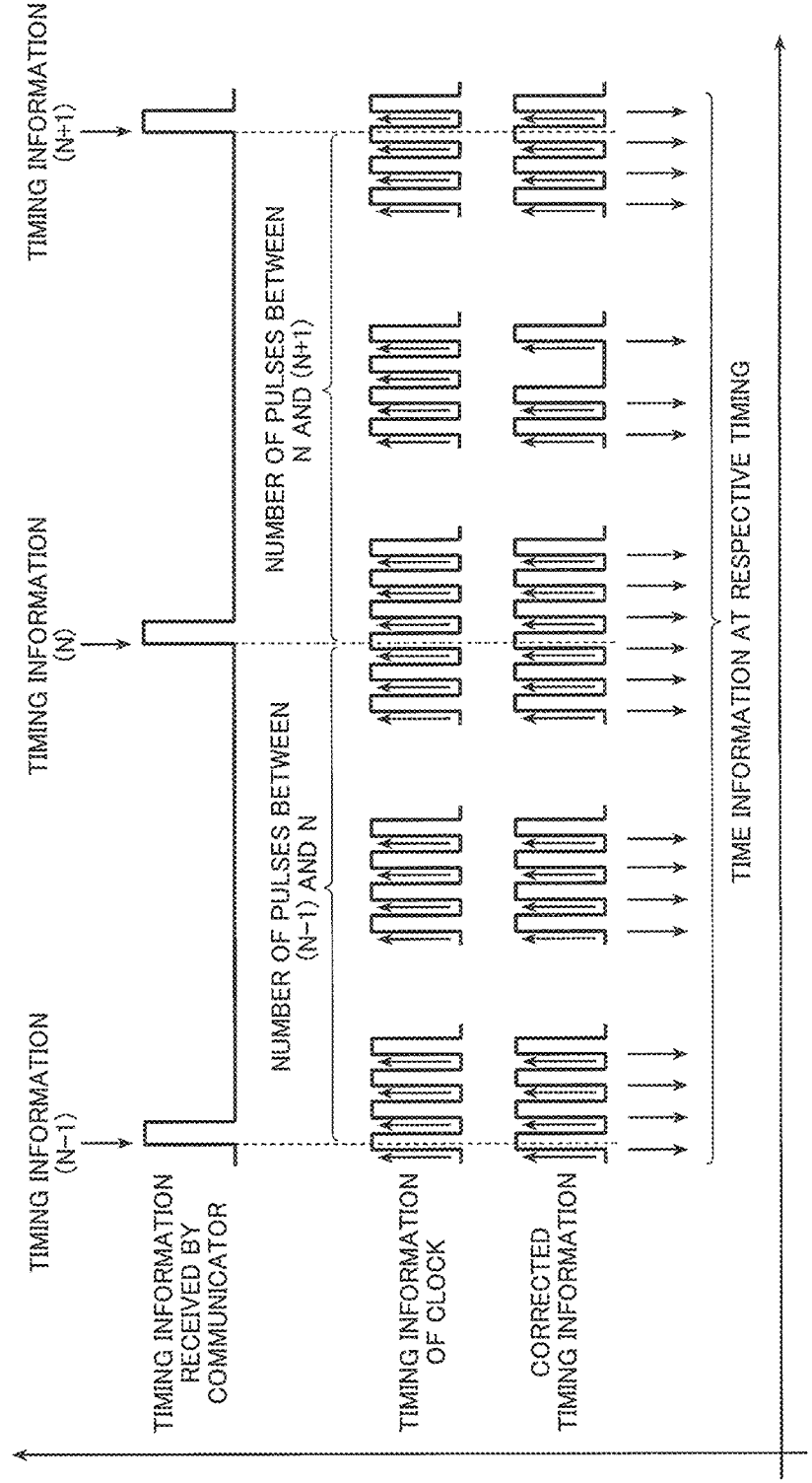
FIG. 10 is a timing chart of an operation of the radiographic imaging apparatus in FIG. 8 or the radiation controlling apparatus in FIG. 9.
Figure 11:
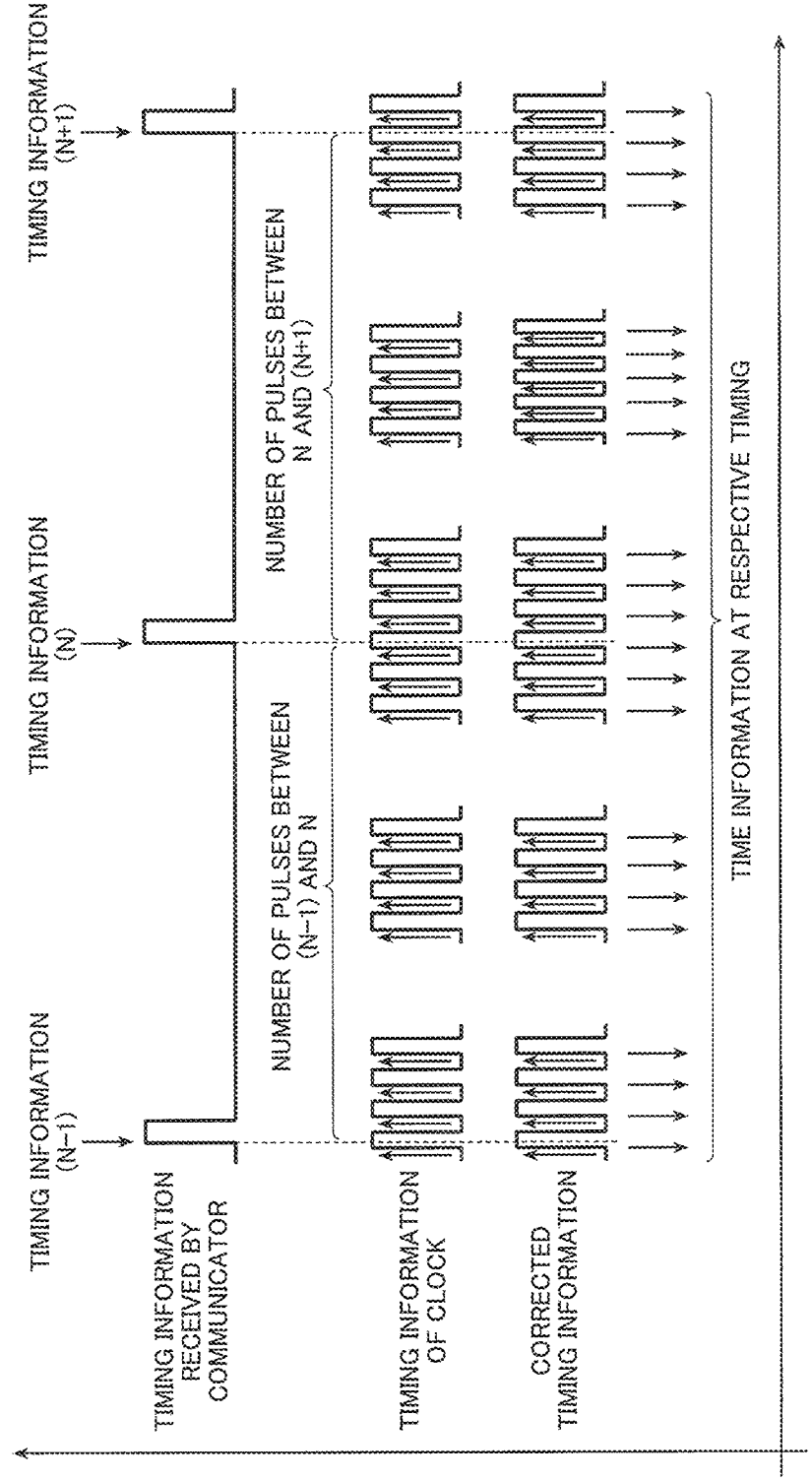
FIG. 11 is a timing chart of an operation of the radiographic imaging apparatus in FIG. 8 or the radiation controlling apparatus in FIG. 9.

Method of Checking Clock Information Lag by Comparing Timing Information with Timing Information FIG. 10 and FIG. 11 illustrate an operation of the controlling apparatus 12 or the imaging apparatus 3 that receives the first clock information.

Assuming that the clock information source apparatus 2, 4 is configured as the first clock to generate timing information while the clock controller 3*a*, 12*a* is configured as the second clock to obtain timing information. In the example illustrated in FIG. 10 and FIG. 11, the clock controller 3*a*, 12*a* counts the number of pulses of the own clock 125, 37 in the period after an input of the timing information from the clock information source apparatus 2, 4 until the next input of the timing information (i.e. the period after the reception of the (N−1)th pulse until the reception of the N-th pulse) and determines the clock rate of the own clock 125, 37 relative to the clock rate of the clock information source apparatus 2, 4.

For example, when the output cycle of the first clock information from the clock information source apparatus 2, 4 is set to 1 second while the frequency of the own clock 125, 37 is set to 10 MHz, 10000000 pulses are counted per second.

However, in practice, the pulse generating rate fluctuates due to the instability of the clock of the clock information source apparatus 2, 4, the insufficient precision of the imager clock 37 or the irradiator clock 125, a change in temperature and the like, and the number of pulses is not exactly equal to 10000000 but is deviated.

The difference is the clocking difference between the clock of the clock information source apparatus 4 and the clock the imaging apparatus 3 or the controlling apparatus 12.

For example, in the example in FIG. 10, assuming that the number of pulses after reception of the (N−1)th pulse until reception of the N-th pulse is 10000010, which is greater than the specified value by 10, it can be understood that the own clock 125, 37 is faster by $10/10000000$ than the clock information source apparatus 4.

For another example, in the example in FIG. 11, assuming that the number of pulses after reception of the (N−1)th pulse until reception of the N-th pulse is 9999990, which is less than the specified value by 10, it can be understood that the own clock 125, 37 is slower by $10/10000000$ than the clock information source apparatus 4.

Method of Checking Clock Information Lag by Comparing Timing Information with Time Information Assuming that the clock information source apparatus 2, 4 is configured as the first clock to generate timing information while the clock controller 3*a*, 12*a* is configured as the second clock to generate time information. In the example illustrated in FIG. 10 and FIG. 11, the clock controller 3*a*, 12*a* generates time information from timing information such as pulses of the own clock 125, 37 in the period after an input of the timing information from the clock information source apparatus 2, 4 until the next input of the timing information (i.e. the period after the reception of the (N−1)th pulse until the reception of the N-th pulse) and determines the clock rate of the own clock 125, 37 relative to the clock rate of the clock information source apparatus 4 from the generated time information.

For example, when the output cycle of the first clock information from the clock information source apparatus 2, 4 is set to 1 second while the frequency of the own clock 125, 37 is set to 10 MHz, 10000000 pulses are generated per second. That is, a pulse is generated in every 0.0000001 second. By correcting the time information by 0.0000001 seconds with respect to each pulse, the time information at each timing can be obtained.

The correction of the time information may be performed with respect to each pulse or each set of pulses. Alternatively, the correction of the time information may be performed when there is a request for the time information.

By repeating the above-described correction of the time information over 1 second, the time information becomes 1 second.

However, in practice, the pulse generating rate fluctuates due to the instability of the clock of the clock information source apparatus 2, 4, the insufficient precision of the imager clock 37 or the irradiator clock 125, a change in temperature and the like, and the time information does not become exactly 1 second but is deviated.

The difference is the clocking difference between the clock of the clock information source apparatus 4, and imager clock 37 or the irradiator clock 125.

For example, in the case in FIG. 10, assuming that the number of pulses after the reception of the (N−1)th pulse until the reception of the N-th pulse is 10000010, which is greater than the specified value by 10, the period of time after the reception of the (N−1)th pulse until the reception of the N-th pulse is 1.000001 second. Accordingly, it can be understood that the clock rate of the own clock 125, 37 is faster by 0.000001 second per 1 second than the clock rate of the clock information source apparatus 4.

For example, in the example in FIG. 11, assuming that the number of pulses after the reception of the (N−1)th pulse until the reception of the N-th pulse is 9999990, which is less than the specified value by 10, the period of time after reception of the (N−1)th pulse until the reception of the N-th pulse is 0.999999 second. Accordingly, it can be understood that the clock rate of the own clock 125, 37 is slower by 0.000001 second per 1 second than the clock rate of the clock information source apparatus 4.

Figure 12:
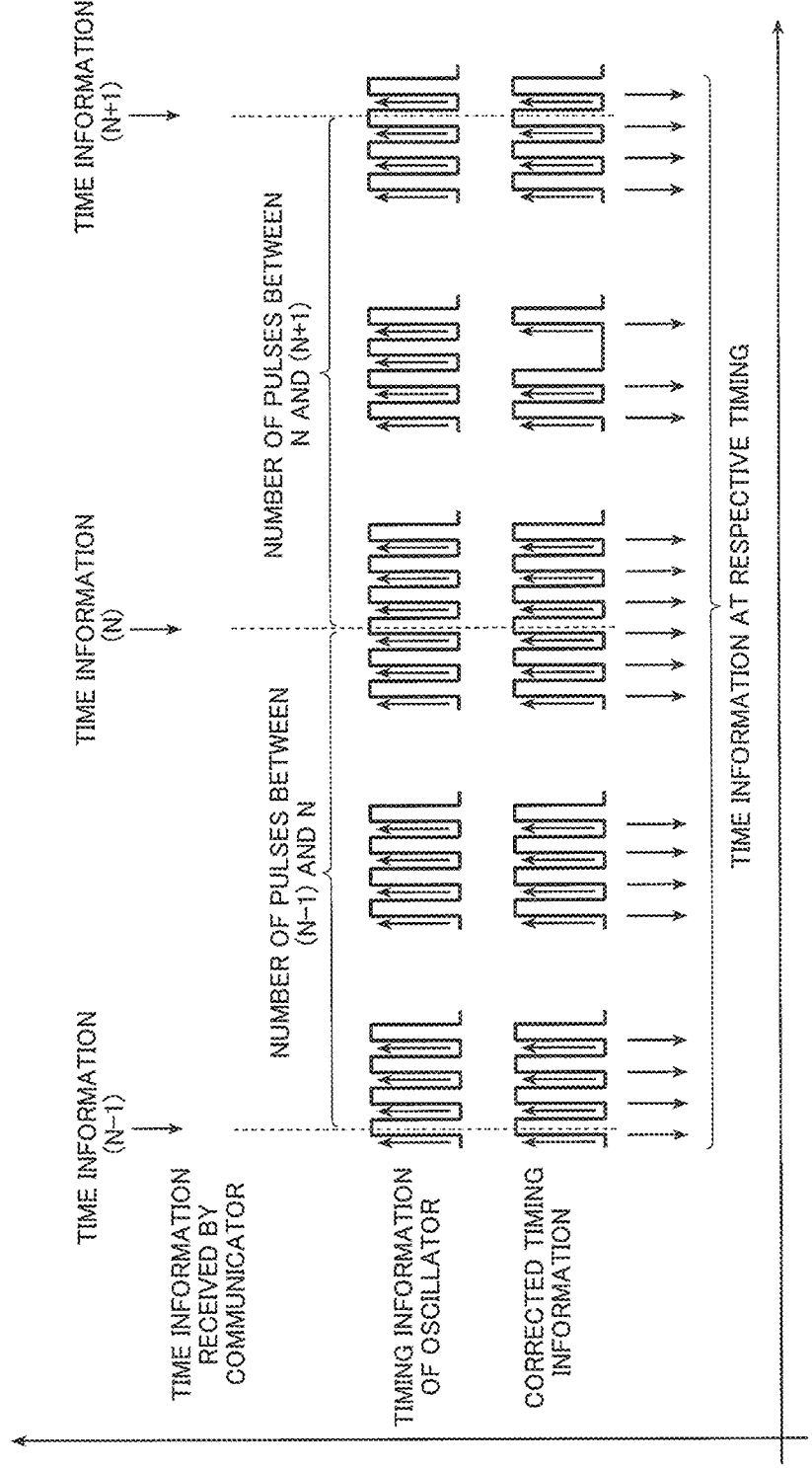
FIG. 12 is a timing chart of an operation of the radiographic imaging apparatus in FIG. 8 or the radiation controlling apparatus in FIG. 9.

Method of Checking Clock Information Lag by Comparing Time Information with Timing Information FIG. 12 illustrates the controlling apparatus 12 or the imaging apparatus 3 that receives the first clock information.

Assuming that the clock information source apparatus 2, 4 is configured as the first clock to generate time information while the clock controller 3a, 12a is configured as the second clock to obtain timing information. In the example illustrated in FIG. 12, the clock controller 3a, 12a counts the number of pulses of the own clock 125, 37 in the period of time after an input of the time information from the clock information source apparatus 2, 4 until the next input of the time information (i.e. the period of time after the reception of the (N−1)th time information until the reception of the N-th time information) and determines the clock rate of the own clock 125, 37 relative to the clock rate of the clock information source apparatus 2, 4.

For example, the clock controller 3a, 12a can obtain the length of time (period) from (N−1) to (N) as the time information from the clock information source apparatus 2, 4 by obtaining the time information at the time point (N−1) and the time information at the time point (N) and calculating the difference between the two time information.

When the clock controller 3a, 12a obtains the clock information at the time point (N−1) and the clock information at the time point (N) as the time information from the own clock 125, 37, the clock controller 3a, 12a can obtain the period of time from the time point (N−1) to the time point (N) by multiplying the counting interval of the clock information source apparatus 4 by the difference between the clock information at the time point (N−1) and the clock information at the time point (N).

Then, the clock controller 3a, 12a compares the period of time from the time point (N−1) to the time point (N) with the product of the number of pulses in the period of time and the pulse interval of the own clock 125, 37 so as to be able to determine the clock rate of the own clock 125, 37 relative to the clock rate of the clock information source apparatus 4.

Method of Checking Clock Information Lag by Comparing Time Information with Time Information Assuming that the clock information source apparatus 2, 4 is configured as the first clock to generate time information while the clock controller 3a, 12a is configured as the second clock to obtain time information. In the example illustrated in FIG. 12, the clock controller 3a, 12a can obtain the length of time (period) from the time point (N−1) to the time point (N) as the time information from the clock information source apparatus 2, 4 by obtaining the time information at the time point (N−1) and the time information at the time point (N) from the clock information source apparatus 2, 4 and calculating the difference between the two time information.

At the same time, the clock controller 3a, 12a can obtain the period of time from the time point (N−1) to the time point (N) as the time information from the own clock 125, 37 by obtaining the time information at the time point (N−1) and the time information at the time point (N) from the own clock 125, 37 and calculating the difference between the two time information.

Then, the clock controller 3a, 12a compares the period of time from the time point (N−1) to the time point N based on the first clock information with the period of time from the time point (N−1) to the time point N based on the second clock information so as to be able to determine the clock rate of the own clock 125, 37 relative to the clock rate of the clock information source apparatus 4.

By comparing the first clock information with the second clock information by any one of the above-described four methods, the clock controller 3a, 12a can determine the clock rate of the own clock 125, 37 relative to the clock rate of the clock information source apparatus 2, 4.

Determination as to Whether Particular Condition is Met

The imaging controller 31 makes a determination as to whether a particular condition is met based on the obtained first clock information and the second clock information.

In the present embodiment, for example, the imaging controller 31 makes a determination as to whether the accuracy of the clocks is sufficient by at least one of the following Determination Method 1 to Determination Method 3. When the clock accuracy is insufficient, the imaging controller 31 determines that the particular condition is met.

Clock Accuracy Determination Method 1 (difference)

When the time difference (time lag) between the first clock information and the second clock information is used for the determination of the clock accuracy, the imaging controller 31 calculates the difference between the obtained first clock information and the second clock information and makes a determination as to whether the difference is greater than a specific value. When the difference is greater than the specific value, the imaging controller 31 determines that the clock accuracy is insufficient, i.e. the particular condition is met.

Clock Accuracy Determination Method 2 (Amount of Change)

When the change of the time difference (time lag) is used for the determination, for example, the imaging controller 31 calculates the difference between the first clock information and the second clock information and stores the difference in the storage 35 every time it obtains the first clock information and the second clock information. Then, the imaging controller 31 calculates the amount of change between the stored previous difference and the latest difference and makes a determination as to whether the calculated amount of change is greater than a previously calculated amount of change. When the latest amount of change is greater than the previous amount of change, the imaging controller 31 determines that the clock accuracy is insufficient, i.e. the particular condition is met.

When a predicted difference is used for the determination, for example, the imaging controller 31 may calculate the difference between the obtained first clock information and the second clock information and the amount of change of the difference and store them in the storage 35. Then, when the difference and the amount of change stored in the storage 35 indicate that the difference changes in a similar manner continuously for a predetermined period of time (e.g. an imaging period), the imaging controller 31 may make a determination as to whether the change is greater than a specific value.

To determine whether the particular condition is met, the difference between the first clock information and the second clock information and the amount of change thereof may be directly used as described above. Instead, the average value may be calculated, or the state of change or a future predicted value may be calculated by linear interpolation, spline interpolation or the like.

To calculate the average, for example, the imaging controller 31 calculates the difference between the obtained first clock information and the second clock information and stores it in the storage 35. Then, the imaging controller 31 calculates the average of stored differences. The amount of change of the difference may sometimes change drastically. By calculating the average, it is possible to cope with such drastic changes.

Parameters required for linear interpolation or spline interpolation can be determined by the least-square method or the like. Regarding such techniques for making the determination, interpolation or extrapolation techniques used in the other fields may be applied to make an advanced determination.

Specific Output

When it is determined that the particular condition is met, the clock controller 3a, 12a performs a specific output.

Examples of the specific output of the present embodiment includes the following outputs.

Specific Output 1 (Correction of Clock Information)

When it is determined that the particular condition is met, the clock controller 3a, 12a corrects the operation of the timer 125, 37 so as to reduce the difference between the first clock information of the clock information source apparatus 2, 4 and the clock information of the own clock 125, 37.

To correct the operation, for example, the timing information or the time information may be corrected as described below.

Correction of Timing Information

In the example in FIG. 10 and FIG. 11, the clock controller 3a, 12a checks the clock rate of the own clock 125, 37 in the period of time after the reception of the (N−1)th clock information until the reception of the N-th clock information by the above-described methods. For example, when the clock controller 3a, 12a determines that the particular condition is met, it may correct the timing information of the own clock 125, 37 in the period of time after the reception of the N-th timing information until the reception of the (N+1)th timing information.

To correct the timing information, for example, a pulse may be removed or added with respect to a certain period of time according to the detected difference of the clock rate as illustrated in FIG. 10.

For example, in the example in FIG. 10, when the number of pulses in the period of time after the reception of the (N−1)th pulse until the reception of the N-th pulse is 10000010, which is greater than the specified value by 10, the clock controller 3a, 12a may remove one pulse in every 1000000 pulses in the period of time after the reception of the N-th pulse until reception of (N+1)th pulse. Alternatively, the clock controller 3a, 12a may slow down the pulse generation to reduce the number of pulses.

For another example, in the example in FIG. 11, when the number of pulses in the period of time after the reception of the (N−1)th pulse until the reception of the N-th pulse is 9999990, which is less than the specified value by 10, the clock controller 3a, 12a may count one pulse in every 1000000 pulses as two pulses in the period of time after reception of the N-th pulse until reception of (N+1)th pulse. Alternatively, the clock controller 3a, 12a may speeds up the pulse generation to increase the number of pulses.

Alternatively, the clock controller 3a, 12a may correct the pulse interval.

For example, when a CR oscillator circuit or an LC oscillator circuit is used as a pulse source, it is possible to readily adjust the pulse interval by changing the property of C (capacitor), R (resistor) and L (coil).

Correction of Time Information

The clock controller 3a, 12a checks the clock rate of the own clock 125, 37 in the period of time after the reception of the (N−1)th clock information until the reception of the N-th clock information by the above-described methods. When the clock controller 3a, 12a determines that the particular condition is met, it may correct the time information of the own clock 125, 37 in the period of time after the reception of the N-th time information until the reception of the (N+1)th time information.

As described above, regardless of whether the clock information that the clock information source apparatus 2, 4 sends is timing information or time information, and regardless of whether the clock information to be corrected by the clock controller 3a, 12a is timing information or time information, it is possible to suitably correct the clock rate of the timer 125, 37 according to the difference relative to the clock rate of the clock information source apparatus 2, 4 by the above-described methods.

Specific Output 2 (Warning of Clock Accuracy Lag and Imaging Permission)

When it is determined that the particular condition is met, for example, the controller 31, 121 performs at least one of the following actions.

Notify to a user that the clock information has not been corrected for a predetermined period of time.

Notify that imaging is disabled.

Prohibit imaging.

Allow a user to select whether to cancel the imaging process.

Cancel the imaging process.

The controller 31, 121 can give the notification by displaying a message or the like on the display or by light, sound, vibration or the like.

To disable imaging or to cancel the imaging process, the radiation controller 121 stop sending a control signal to the high voltage generator 122, sends a signal representing an instruction to cancel the imaging process to the high voltage generator 122, or the like.

To allow a user selection, for example, the controller 31, 121 displays options on the display and follows a user operation that is input on the operation interface.

At least one of the above-described actions such as the notification and the cancellation of the imaging process may be performed at the same time with allowing a user selection.

Alternatively, after cancelling imaging, the controller 31, 121 may also correct the clock information of the imager clock 37 based on the clock information of the clock information source apparatus 2, 4.

Some typical radiographic imaging systems can synchronize an irradiating apparatus with a radiographic imaging apparatus by correcting clock information of a second clock every time clock information is periodically sent to the second clock from a first clock that is synchronized with the irradiating apparatus.

In a serial imaging process, such radiographic imaging apparatuses repeat the steps of accumulating charges in an image receiver, which are mainly generated by radiation, reading and transferring the accumulated charges and initializing the image receiver.

For example, when the clock information of the first or second clock is corrected, the length of time of accumulating charges in pixels in taking a certain frame image may sometimes become different from the length of the accumulation time in taking the other serial frame images. In this case, the amount of charges accumulated in the image receiver is changed according to the difference of the length of time.

For example, when the length of the accumulation time in taking a certain frame image becomes longer than the length of the accumulation time in taking the other serial frame images as a result of correcting the clock information of the clock, the image receiver receives the image for a longer time in taking the certain frame image than in taking the other serial frame images. That is, the image receiver accumulates charges for a longer time than the accumulation time in taking the other serial frame images.

To cope with the problem, for example, the irradiating apparatus may be controlled to emit pulsed radiation only during a part of the accumulation period. With this configuration, it is possible to even out the amount of radiation from the irradiating apparatus in each accumulation time even when the length of accumulation time varies.

However, the image receiver generates and accumulates charges even by scattered radiation emitted from the outside or a subject S in addition to the radiation emitted from the radiation irradiating apparatus. To remove such scattered radiation, a grid may sometimes be provided between the subject S and the image receiver. However, the grid cannot remove scattered radiation completely. That is, even when the irradiating apparatus is controlled to emit radiation only during a part of the accumulation period, reception of scattered radiation, i.e. accumulation of charges, cannot be eliminated. When the time of the clock is changed so that the length of accumulation time in taking a certain frame image becomes different from the length of accumulation time in taking the other serial frame images, only the certain frame image, which is taken when the time of the clock is changed, is affected by the scattered radiation to a different degree from the other serial frame images.

In contrast, the imaging system 100 of the present embodiment is configured such that when the first clock information is sent from the clock information source apparatus 2, 4, the imaging apparatus 3 makes a determination as to whether the particular condition is met. Only if the particular condition is met, the clock information of the imager clock 37 (second clock) is corrected. Therefore, the imaging system can take a suitable measure only at suitable timing, for example, when the difference of the clock information between the clocks is increased to such a level that affects the contents of an image (diagnosis).

Clock Accuracy Determination Method 4

In order that the imaging system 100 according to the embodiment performs the above-described operations, communication is established between the clock information source apparatus 2, 4 and the apparatus (at least one of the controlling apparatus 12 and the imaging apparatus 3) that receives the first clock information. Depending on the environment in which the imaging system 100 is used, the communication cannot be established (the above-described operations are not performed), and an operation lag sometimes occurs between the irradiating apparatus 1 and the imaging apparatus 3.

To cope with the problem, the imaging system 100 of the embodiment may have the following function of detecting such operation lags.

Figure 13:
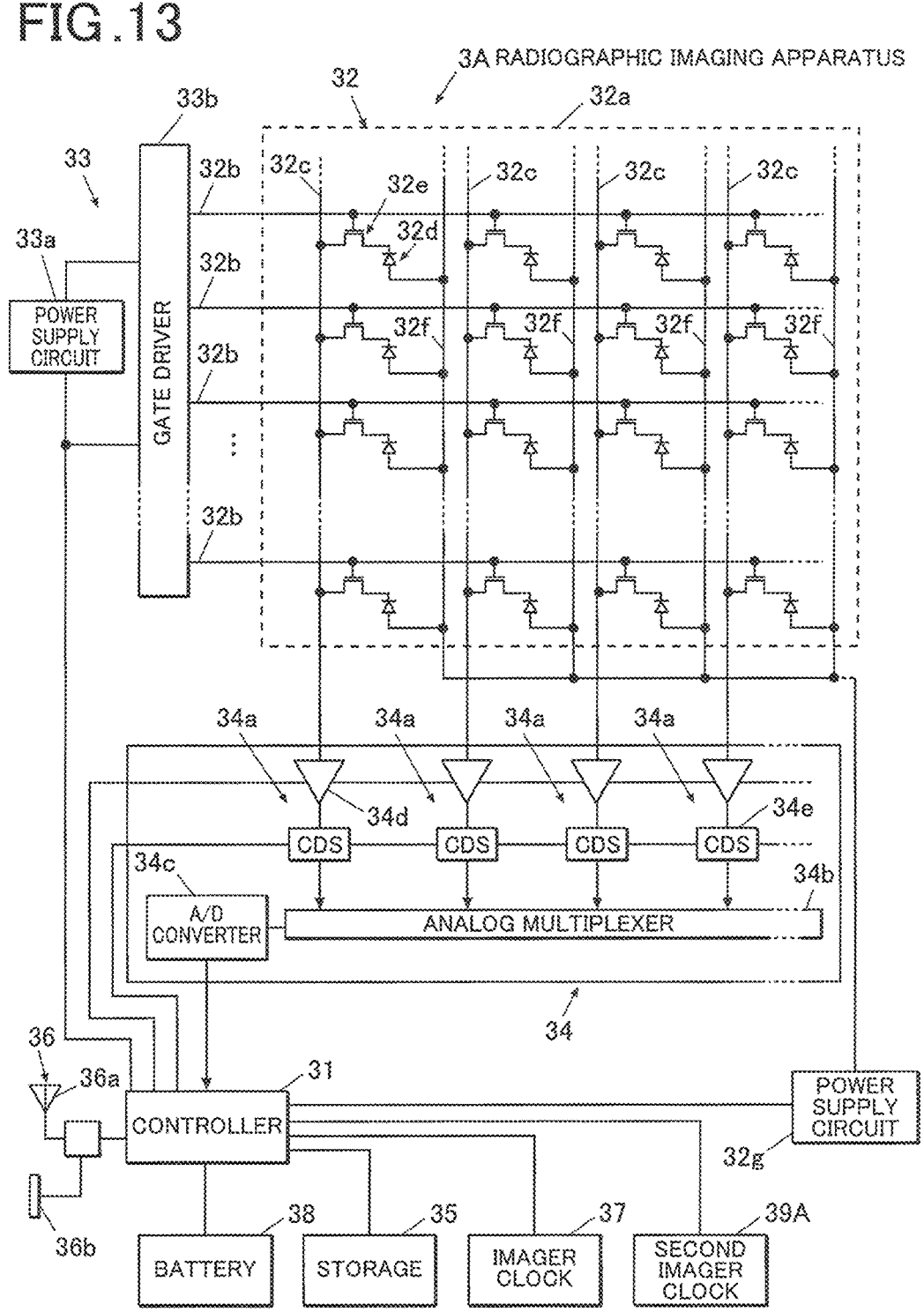
FIG. 13 is a block diagram the radiographic imaging apparatus of the radiographic imaging system according to the embodiment, illustrating another example of the configuration thereof.

Specifically, the controlling apparatus 12 or the imaging apparatus 3 that receives the first clock information includes a second imager clock 39A that performs a counting operation in synchronization with the imaging apparatus 3A as illustrated in FIG. 13 in addition to the imager clock 37.

The clock controller 3a, 12a has a function of resetting the clock information of the second imager clock 39A when the clock controller 3a, 12a receives the first clock information from the clock information source apparatus 2, 4.

When the second imager clock 39A is reset, it starts the counting operation from an initial value again.

The clock controller 3a, 12a has a function of determining as to whether the clock information of the second imager clock 39A is greater than a predetermined threshold.

Figure 14:
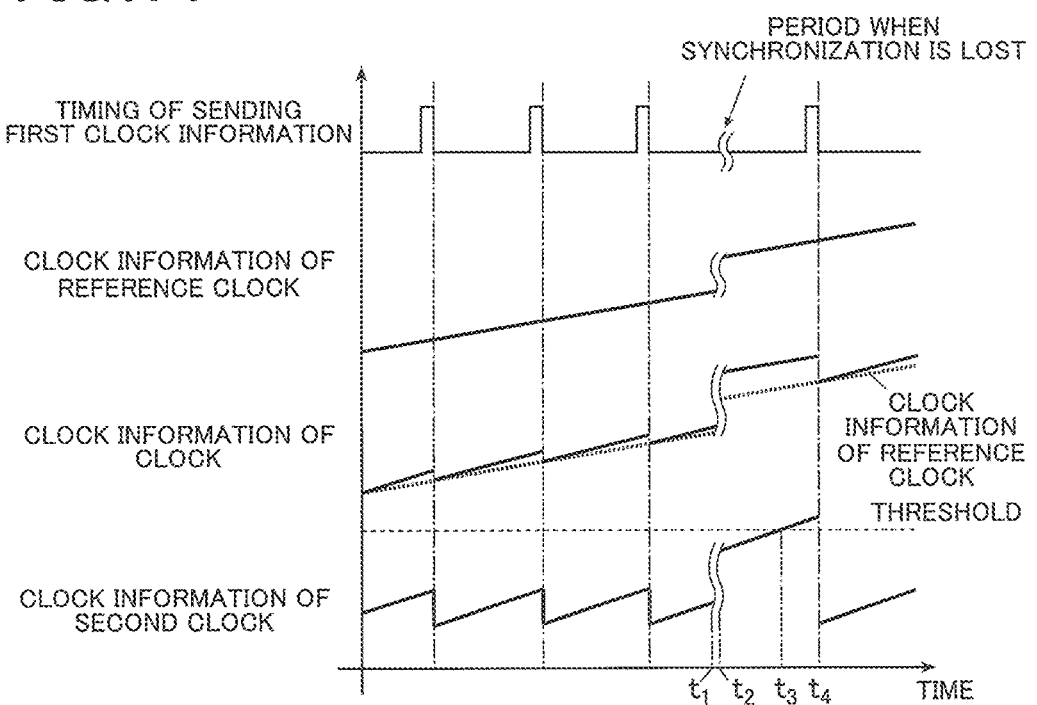
FIG. 14 is a timing chart of an operation of the radiographic imaging system in FIG. 13.

The imaging system 100 of the present embodiment having the above-described configuration operates as follows. While there is no abnormality in the communication between the clock information source apparatus 2, 4 and the imaging apparatus 3A (between t0 and t1), the clock information does not exceed the threshold since the clock information of the second imager clock 39A is repeatedly reset as illustrated in FIG. 14 every time the imaging apparatus 3A receives the first clock information. When an abnormality occurs in the communication between the clock information source apparatus 2, 4 and the imaging apparatus 3A so that the first clock information cannot be received from the clock information source apparatus (between t1 and t2), the imager clock 37 does not correct the clock information, and the second imager clock 39A continues the counting operation without resetting the clock information. Thereafter, when the clock information of the second imager clock 39A exceeds a threshold (t3), the imaging apparatus 3A understands that the clock information of the imager clock has not been corrected by the first clock information of the clock information source apparatus 2, 4 for a predetermined period of time. Then, the imaging apparatus 3A outputs the understanding.

At the same time with outputting the understanding, the imaging apparatus 3A may perform at least one of the following actions, which are the same actions that are performed when the particular condition is met in the above-described embodiment.

Inform a user the clock information has not been corrected for a predetermined period of time.

Notify that imaging is disabled.

Disable imaging.

Allow a user to select whether to cancel the imaging process.

Cancel the imaging process.

Thereafter, when the communication is recovered so that the first clock information is received, the second imager clock 39A resets the clock information (t4), and the imaging system 100 gets back to the normal operation.

In the imaging system 100 according to the embodiment having the above-described configuration, when the clock information of the clock 37, 125 has not been corrected with the first clock information for a certain period of time, it is possible to understand it or to measure the length of time by using the second imager clock 39A.

Further, a determination is made as to whether the time difference between the clock information of the first clock and the clock information of the imager clock falls within an allowable range by comparing the clock information of the second imager clock with the threshold. If the time difference is out of the allowable range, it is possible to take a suitable measure.

Clock Accuracy Determination Method 5

As described above, a failure of establishing communication sometimes cause an operation lag between the irradiating apparatus 1 and the imaging apparatus 3 depending on the environment in which the imaging system 100 is used. To cope with the problem, that the imaging system 100 of the embodiment may have a function of detecting the operation lag in the following way.

Figure 15:
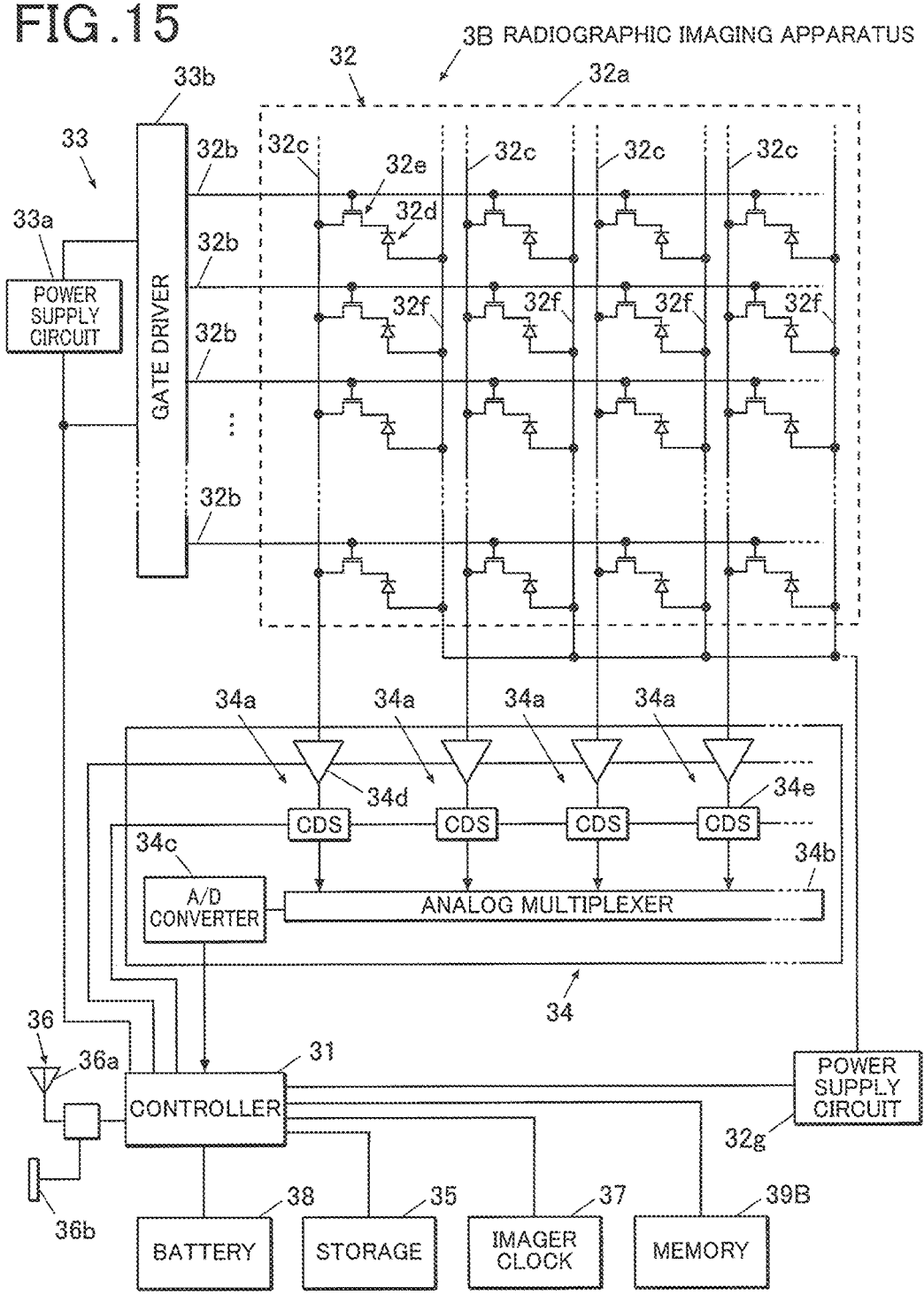
FIG. 15 is a block diagram of the radiographic imaging apparatus of the radiographic imaging system according to the embodiment, illustrating another example of the configuration thereof.

Specifically, the controlling apparatus 12 or the imaging apparatus 3 that receives the first clock information includes a memory 39B as illustrated in FIG. 15 instead of the second imager clock 39A.

When the first clock information is received from the clock information source apparatus 2, 4, the memory 39B stores the received first clock information, i.e. the corrected clock information of the imager clock 37.

Instead of providing the memory 39B, the same function may be imparted to the storage 35.

The clock controller 3a, 12a has a function of making a determination as to whether the difference between the clock information of the imager clock 37 and the value stored in the memory 39B is greater than a predetermined threshold.

Figure 16:
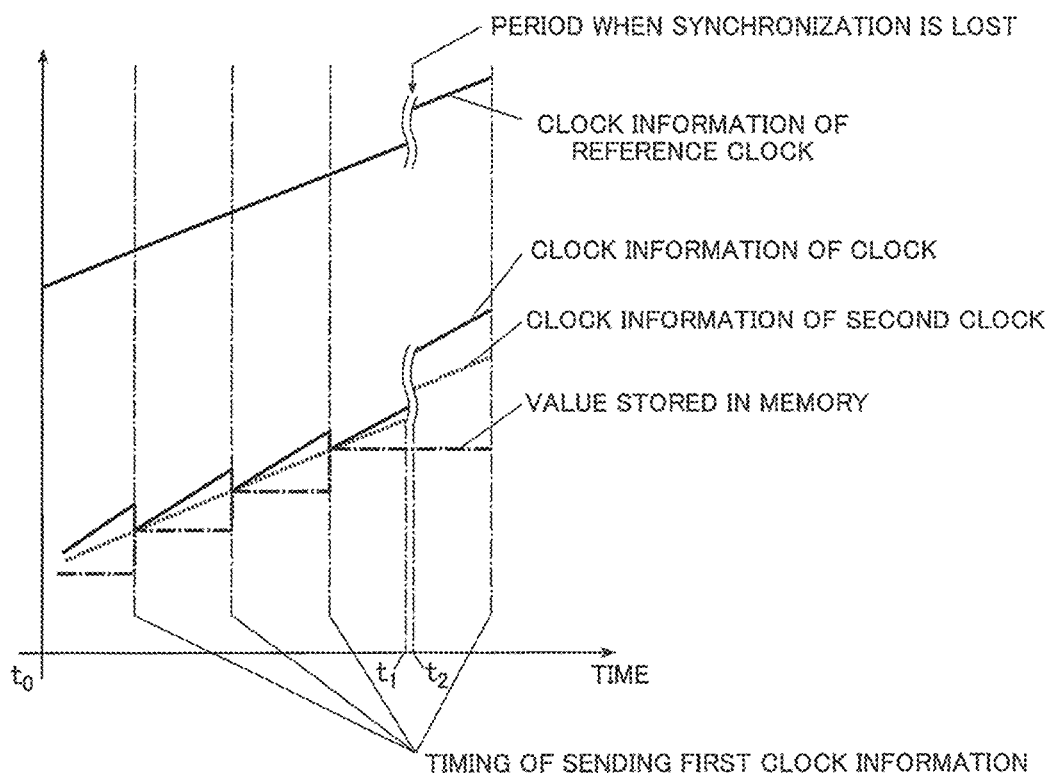
FIG. 16 is a block diagram of the radiographic imaging system in FIG. 15 according to the embodiment, illustrating the configuration thereof.

In the imaging system 100 of the embodiment having the above-described configuration, when there is no abnormality in the communication between the clock information source apparatus 2, 4 and the imaging apparatus 3B (between t0 and t1), the memory 39B stores the first clock information every time the imaging apparatus 3B receives the first clock information as illustrated in FIG. 16. Therefore, the difference between the clock information of the imager clock 37 and the first clock information in the memory 39B does not exceed the threshold. However, when an abnormality occurs in the communication between the clock information source apparatus 2, 4 and the imaging apparatus 3B so that the first clock information cannot be received from the clock information source apparatus 2, 4 (between t1 and t2), the imager clock 37 does not correct the clock information, and the first clock information in the memory 39B is no updated. Thereafter, when the difference between the clock information and the old first clock information in the memory 39B exceeds the threshold, the imaging apparatus 3B understands that the clock information of the imager clock has not been corrected by the first clock information of the clock information source apparatus 2, 4 for a predetermined period of time. Then, the imaging apparatus 3B outputs it as with the imaging apparatus 3 of the present invention.

At the same time with outputting the understanding, the imaging apparatus 3A may perform at least one of the following operations, which are the same actions as those performed when the particular condition is met described in the "clock accuracy determination method 4".

Thereafter, when the communication is recovered so that the first clock information is received, the first clock information the in memory 39B is updated, and the imaging system 100 gets back to the normal operation.

In the imaging system 100 according to the embodiment having the above-described configuration, when the clock information of the clock 37, 125 has not been corrected by the first clock information for a predetermined period of time, it is possible to detect it without using the second imager clock 39A, i.e. with a smaller number of clocks than the first embodiment.

In the foregoing, the imaging system 100 of the embodiment is described. In addition to the configuration in FIG. 1, the imaging system 100 may have a variety of other configurations with regard to the connection of the clock information source apparatus 2, 4, the radiation controlling apparatus 12, the console 14, the operation interface 15 and the exposure switch 15a.

For example, the operation interface 15 may be connected only to the console 14, and signals corresponding to user operations on the operation interface 15 may be inputted to the controlling apparatus 12 via the console 14.

For another example, it is not necessary that the clock information source apparatus 2, 4 is connected to both the controlling apparatus 12 and the console 14. The clock information source apparatus 2, 4 may be connected only to the console 14 to correct information or time with respect to the console 14, and the controlling apparatus 12 may control information or time via the console 14.

For still another example, the exposure switch 15a may be directly connected to the controlling apparatus 12 instead of the operation interface 15.

Similarly, the systems in the following figures may have various configuration with regard to the connection of the components without departing from or impairing the object, the functions and the effects of the present invention.

Supplementary Techniques

Next, another embodiment of the radiographic imaging system to which the present invention is applicable will be described.

The same reference signs are denoted to the same components as those of the above-described embodiment, and the description thereof is omitted.

Configuration of Radiographic Imaging System

First, an overview of a radiographic imaging system (hereinafter referred to as an imaging system 100A) of the present embodiment will be described. FIG. 17 is a block diagram of the imaging system 100A, illustrating the schematic configuration thereof.

As illustrated in FIG. 17, the imaging system 100A of the present embodiment includes a tube 13, a console 14 and a clock information source apparatus 2, 4 that are the same as those of the previously described embodiment and further includes a controlling apparatus 12A, a radiographic imaging apparatus (hereinafter referred to as an imaging apparatus 3C) and the like.

The controlling apparatus 12, the console 14 and the imaging apparatus 3C can communicate with each other via the clock information source apparatus 2, 4.

Details of the controlling apparatus 12 and the imaging apparatus 3C will be described later.

FIG. 17 illustrates an example of the imaging system 100A in which both an irradiating apparatus 1 and the imaging apparatus 3 communicate with the clock information source apparatus 2, 4 in a wireless manner. However, in the imaging system 100A of the present embodiment, it is only necessary that at least one of the irradiating apparatus 1 and the imaging apparatus 3 communicates with the clock information source apparatus 2, 4 in a wireless manner. For example, as illustrated in FIG. 1, the irradiating apparatus 1 may be connected to the clock information source apparatus 2, 4 by wire.

In this configuration, the synchronization accuracy between the controlling apparatus 12 and the clock information source apparatus 2, 4 can be maintained at a sufficiently high level. Since it is not necessary to add a function of switching the operation mode to the controlling apparatus 12, the controlling apparatus 12 can be produced at low cost.

An IF of the imaging apparatus 3C may be changed from wireless communication to wired communication, and the clock information source apparatus 2, 4 may be connected to the imaging apparatus 3C by a dedicated line.

In this configuration, it is not necessary to add a function of switching the operation mode to the imaging apparatus 3C.

Configuration of Radiographic Imaging Apparatus

Figure 18:
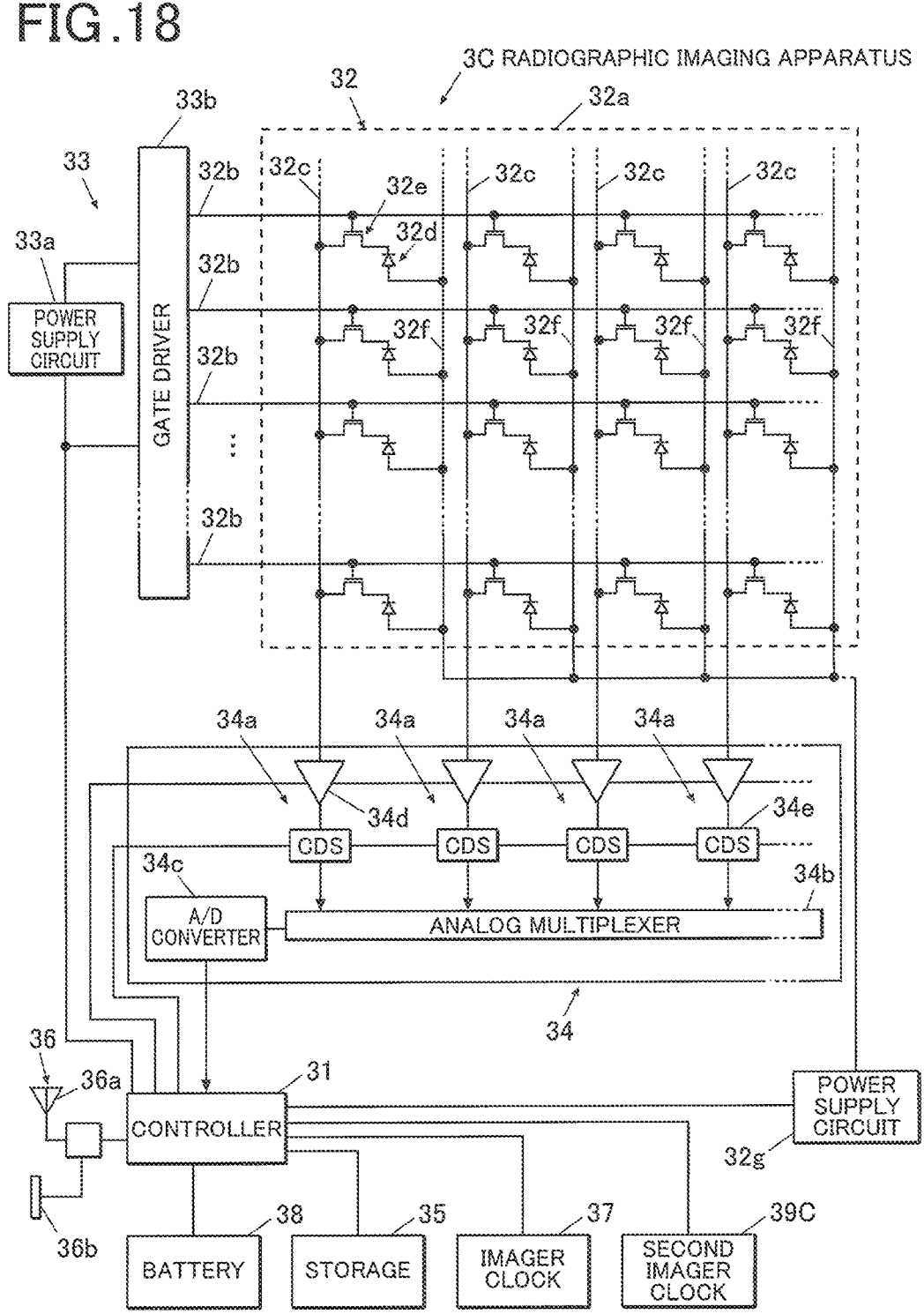
FIG. 18 is a block diagram of the radiographic imaging apparatus of the radiographic imaging system in FIG. 17, illustrating the specific configuration thereof.

Next, the specific configuration of the imaging apparatus 3C of the imaging system 100A will be described. FIG. 18 is a block diagram of the imaging apparatus 3C, illustrating the specific configuration thereof.

The imaging apparatus 3C has a similar configuration as the imaging apparatus 3A of the previously described embodiment. That is, as illustrated in FIG. 18, the imaging apparatus 3C includes a radiation detector 32, a scanner driver 33, a reader 34, a storage 35, a communicator 36, a battery 38 and an imager clock 37A that are the same as those of the previously described embodiment and further includes an imaging controller 31A and a second imager clock 39C.

The second imager clock 39C, which performs a clocking operation in the same manner as the imager clock 37A, starts the clocking operation to generate clock information when the apparatus is powered on or it receives a predetermined external control signal.

The second imager clock 39C may output either timing information such as pulses at regular intervals or time information such as year, month, day, hour, minute and second or the number of counts that is counted up at regular intervals from a certain time point.

In recent years, some LAN chips have such timer function as a default function, which is a timing synchronization function (hereinafter referred to as a TSF) specified in the communication standards of the IEEE 802.11.

This type of a wireless LAN chip can be used as the second imager clock 39C.

However, the operation of the imager clock 37A and the second imager clock 39C of the present embodiment is partly different from the operation of the imager clock 37 and the second imager clock 39A of the previously-described embodiment.

Specifically, in the previously-described embodiment, the imager clock 37A of the imaging controller 31 corrects the clock information only when the particular condition is met. In contrast, in the present embodiment, the imaging controller 31A of the imaging apparatus 3C updates clock information of the imager clock 37 to first clock information every time it receives the first clock information from the clock information source apparatus 2, 4.

Further, the second imager clock 39C of the imaging controller 31 of the previously-described embodiment only resets the clock information every time it receives the first clock information. In contrast, the second imager clock 39C of the present embodiment can switch its own operation mode to a synchronization mode or to a free-running mode in some conditions.

The switching of the operation mode will be described later.

The imaging controller 31A updates the clock information of the second imager clock 39C to the clock information of the imager clock 37A at predetermined timing and then allows the second imager clock 39C to continue the counting operation. As described above, the imager clock 37A performs time synchronization with the clock information source apparatus 2, 4 every time it receives the first clock information from the clock information source apparatus 2, 4. Accordingly, the second imager clock 39C is also repeatedly synchronized with the clock information source apparatus 2, 4 at predetermined intervals while it is in the synchronization mode.

When the second imager clock 39C is in the free-running mode, the imaging controller 31A does not update the clock information of the second imager clock 39C to the clock information of the imager clock 37A but allows the second imager clock 39C to continue its counting operation.

The communicator 36 has the same configuration as that of the previously-described embodiment.

Configuration of Radiation Controlling Apparatus

Next, the specific configuration of the controlling apparatus 12A of the imaging system 100A will be described. FIG. 19 is a block diagram of the controlling apparatus 12A, illustrating the specific configuration thereof.

As illustrated in FIG. 19, the controlling apparatus 12A of the present embodiment includes a radiation controller 121, a high voltage generator 122, a storage 123, a communicator 124, an irradiator clock 125 that are the same as those of the previously-described embodiment and further includes a second irradiator clock 126, a display 127, an operation interface 15 and the like.

As with the previously-described embodiment (as illustrated in FIG. 1), the operation interface 15 may be configured as an operating panel 15 separately from the controlling apparatus 12A.

The second irradiator clock 126, which performs a clocking operation in the same manner as the irradiator clock 125, starts the clocking operation to generate clock information when the apparatus is powered on or it receives a predetermined external control signal.

The second irradiator clock 126 may output either timing information such as pulses at regular intervals or time information such as year, month, day, hour, minute and second or the number of counts that is counted up at regular intervals from a certain time point.

In recent years, some LAN chips have such timer function as a default function, which is a timing synchronization function (hereinafter referred to as a TSF) specified in the communication standards of the IEEE 802.11.

This type of a wireless LAN chip can be used as the second imager clock 125.

The display 127 is constituted by a monitor such as an LCD (Liquid Crystal Display) or a CRT (Cathode Ray Tube). According to a display signal from the radiation controller 121, the display 127 displays an input on the operation interface 15, irradiation result information (e.g. the tube voltage, the tube current, the irradiation time, the tube current-irradiation time product, the number of images taken, the received dose, the area dose and the like), a radiographic image based on image data, and the like.

The operation interface 15 includes a two-button exposure switch 12h.

The exposure switch 12h is connected to a main body of the operating panel 15 by wire.

However, the exposure switch 12h may be connected to the main body of the operation interface 15 in a wireless manner.

In response to a user operation on the exposure switch 12h, the operation interface sends an imaging start signal to the tube 13 and the imaging apparatus 3.

The radiation controller 121 having the above-described configuration updates the clock information of the irradiator clock 125 to the first clock information every time it receives the first clock information from the clock information source apparatus 2, 4.

Further, the radiation controller 121 can switch the operation mode of the second irradiator clock 126 to the synchronization mode or to the free-running mode in some conditions.

The switching of the operation mode will be described later.

The radiation controller 121 updates the clock information of the second irradiator clock 126 to the clock information of the irradiator clock 125 at the predetermined timing and then allows the second irradiator clock 126 to continue its counting operation. As described above, the irradiator clock 125 performs the time synchronization with the clock information source apparatus 2, 4 every time it receives the first clock information from the clock information source apparatus 2, 4. Accordingly, the second irradiator clock 126 is repeatedly synchronized with the clock information source apparatus 2, 4 at predetermined intervals while it is in the synchronization mode.

While the second irradiator clock 126 is in the synchronization mode, the irradiation controller 121 does not update the clock information of the second irradiator clock 126 to the clock information of the irradiator clock 125 but allows the second irradiator clock 126 to continue its counting operation.

Mode Switching

Next, the switching of the operation mode of the second irradiator clock 126 and the second imager clock 39A will be described in detail, which is performed respectively by the radiation controller 121 and the imaging controller 31C (hereinafter also referred to as controllers 121, 31A).

For example, the clock information source apparatus 2, 4 have a trouble to erroneously reset the first clock information of the clock information source apparatus 2, 4. Then, the clock information of the imager clock 37A and the irradiator clock 125 (hereinafter also referred to as clocks 37A, 125), which are synchronized with the clock information source apparatus 2, 4, and the second imager clock 39C and the second irradiator clock 126 (hereinafter also referred to as second clocks 39C, 126), which correct their own clock information based on the clock information of the clocks 37A, 125, are erroneously updated accordingly. When such an abnormality occurs in the course of a serial imaging process which repeats irradiation and accumulation of charges multiple times, the image immediately after the update of the clock information is taken at different timing.

In order that the imaging cycle is not disrupted in the course of the serial imaging process even in such cases, the controllers 121, 31A of the present embodiment switch the operation mode of the second irradiator clock 126 and the second imager clock 39C according to need.

The controllers 121, 31A make a determination as to whether a predetermined condition is met.

In the present embodiment, the predetermined condition being met refers to an abnormality that can negatively affect the timing of taking images being detected. Specifically, for example, it is determined that the predetermined condition is met when: a predetermined event is detected during an imaging period; a period of time after the last synchronization until the next synchronization (an interval of receiving the first clock information) exceeds a predetermined threshold during an imaging period; the change of the clock information of the second imager clock 39C and the second irradiator clock 126 by synchronization exceeds a predetermined threshold during an imaging period; the clock information is drastically changed by restart of the clock information source apparatus 2, 4 or the like during an imaging period; the first clock information has not been received for a long time during an imaging period; or the like.

In addition, it can be determined that the predetermined condition is met when a certain event such as the following events (1) to (3) occur. The certain event may be one of the following events (1) to (3) or a combination thereof.

(1) The number of receptions of the first clock information in an imaging period is counted, and the counted number of receptions is less than a predetermined threshold.

(2) The reception interval of the first clock information is repeatedly measured during an imaging period, and at least one of the measured reception intervals of the first clock information is greater than a predetermined threshold.

(3) The amount of change of the clock information of the second imager clock 39C and the second irradiator clock 126 by synchronization is repeatedly measured during an imaging period, and at least one of the measured amounts of change is greater than a predetermined threshold.

In particular, by using the events (2) and (3), it is possible to immediately detect a failure of synchronization.

When the controllers 121, 31A determine that the predetermined condition is met, they switch the operation mode of the second irradiator clock 126 and the second imager clock 39C to the free-running mode.

After the power is turned on, the controllers 121, 31A keep the operation mode in the synchronization mode until they determine that the predetermined condition is met, i.e. during a default state.

When the predetermined condition is no longer met after an image is taken in the free-running mode, the controllers 121, 31A switch (returns) the operation mode to the synchronization mode.

Not only when the predetermined condition is met, the controllers 121, 31A may keep the operation mode in the free-running mode while there is a possibility that the predetermined condition will be met.

Figure 20:
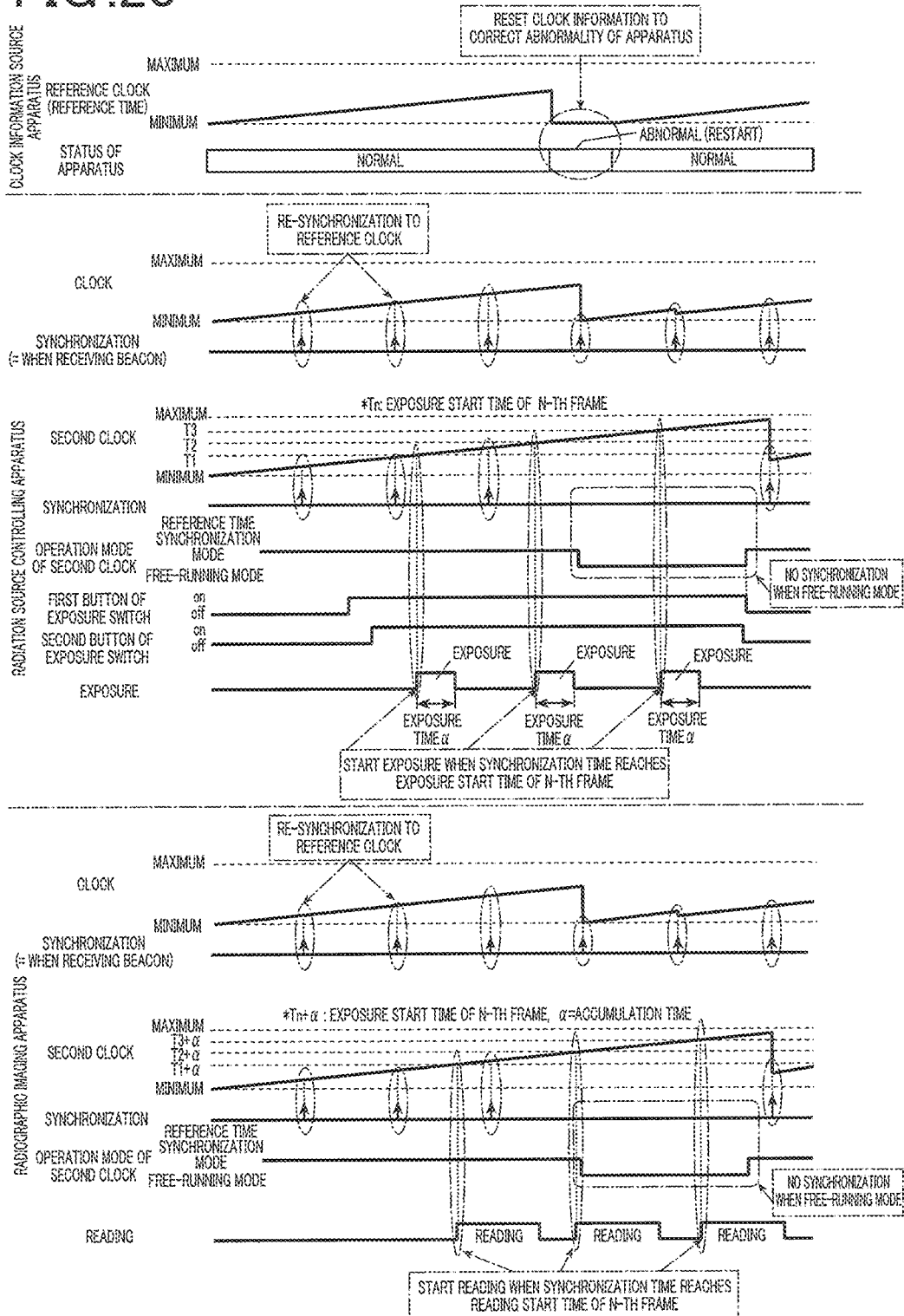
FIG. 20 is a timing chart of an example operation of the radiographic imaging system in FIG. 10.
Figure 21:
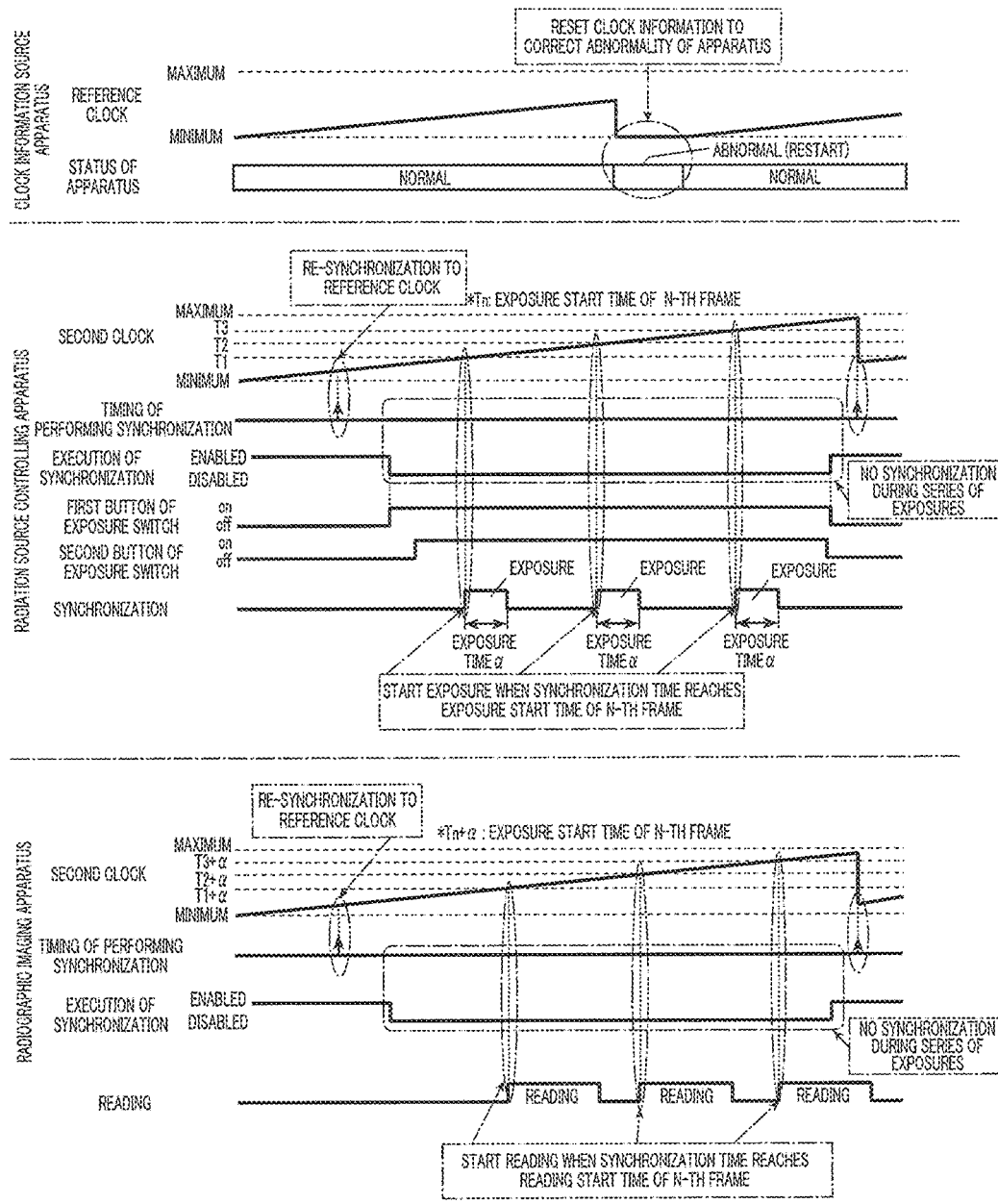
FIG. 21 is a timing chart of another example operation of the radiographic imaging system in FIG. 10.

For example, the controllers 121, 31A may keep the operation mode in the free-running mode from start to finish of an imaging process as illustrated in FIG. 20.

Examples of imaging start triggers that start an imaging process include the following events of Start-1 to Start-8. The imaging start trigger may be a combination of the following events.

Start-1: A user input of an instruction is received on a user interface (hereinafter referred to as a UI) such as the console 14, the imaging apparatus 3, the controlling apparatus 12, the operation interface 15 or the exposure switch 15a.

Start-2: An imaging order is selected on the console 14.

Start-3: The imaging apparatus 3 has become ready for receiving radiation.

Start-4: The first button of the exposure switch 15a is pressed down.

Start-5: The controlling apparatus 12 receives from the tube 13 a signal representing the tube 13 is ready for irradiation, or the controller 121 receives from the high voltage generator 122 a signal representing the high voltage controller 122 is ready for irradiation.

Start-6: The second button of the exposure switch 15a is pressed down.

Start-7: The controlling apparatus 12 receives from the tube 13 a signal representing it has started irradiation for taking the first frame, or the controller 121 receives from the high voltage generator 122 a signal representing it has started irradiation for taking the first frame.

Start-8: A predetermined period of time has elapsed since any of the above-described imaging start trigger events Start-1 to Start-7 occurs.

Examples of imaging end triggers that end an imaging process include the following events of End-1 to End-9. The imaging end trigger may be a combination of the following events.

End-1: A user input of an instruction is received on the UI such as the console 14, the imaging apparatus 3, the controlling apparatus 12, the operation interface 15 or the exposure switch 15a.

End-2: The controlling apparatus 12 receives from the tube 13 a signal representing it has completed irradiation for taking the last frame, or the controller 121 receives from the high voltage generator 122 a signal representing it has completed irradiation for taking the last frame.

End-3: The imaging apparatus 3 or the controlling apparatus 12 has finished processing the last frame.

End-4: The imaging apparatus 3 has finished reading the last frame.

End-5: The second button of the exposure switch 15a is released.

End-6: The first button of the exposure switch 15a is released.

End-7: An error occurs so that the imaging process can be no longer continued.

End-8: The next imaging order is selected on the console 14.

End-9: A predetermined period of time has elapsed since any of the above-described imaging end trigger events End-1 to End-8 occurs.

In a short-time serial imaging process or a still imaging process, even when the operation mode is switched to the free-running mode during the imaging period before the predetermined condition is met, the time lag between exposure and accumulation due to the frequency error of the oscillator of the imaging apparatus 3 or the controlling apparatus 12 may sometimes fall within a required accuracy. When the imaging system 100 is intended only for only short-time serial imaging or still imaging, this allows simplifying the operation of the controller 121, 31 and thereby reducing the time and cost to develop the imaging system 100.

However, the shorter the period of time of the free-running mode, the smaller the operation lag between the imaging apparatus 3 and the controlling apparatus 12. Therefore, it is preferred that the operation mode is switched to the free-running mode at a time point as close as possible to the start of irradiation. For example, when the above-described event Start-4 that the first button of the exposure switch is pressed down is selected as the imaging start trigger to start an imaging process, the period of time of the free-running mode is longer as it takes more time for the user to press down the second button after he/she presses down the first button. To avoid this, it is preferred to select the above-described Start-5 to Start-7 as the trigger than Start-4.

However, depending on the configuration of the tube 13 and the high voltage generator 122 and the system configuration, modification of the apparatuses or wiring is required to use a preferred event as the imaging start trigger. In terms of reducing the development cost, it is desired that the imaging start trigger is selected according to the apparatuses and the system configuration.

When the period of time of the free-running mode is long due to a limited selection of the imaging start trigger events, Start-8 can be selected as the imaging start trigger in order to bring the timing of switching the operation mode to the free-running mode closer to the start of irradiation.

The user may be allowed to switch the operation mode as in Start-1 and End-1. When the user knows that the poor radio wave condition due to the position of the imaging apparatus 3 or radio wave interference with other devices can deteriorate the accuracy of synchronization with the reference time, he/she can manually switch the operation mode to avoid deterioration of the synchronization accuracy.

In this configuration, the current operation mode may be displayed on the display 127, the console 14, the operation interface 15 or a display (not shown) of the imaging apparatus 3. This can improve the usability of the system 100 and avoid an unnecessary switching operation by the user.

When the imaging system 100 includes two or more clock information source apparatuses 2, 4, the imaging system 100 may be configured to switch the connection from the current clock information source apparatus 2, 4 (n) to another clock information source apparatus 2, 4 (n+1) (i.e. to perform wireless LAN loaming) when the imaging apparatus 3 and the controlling apparatus 12 are moved so that the connecting condition with another clock information source apparatus 2, 4 becomes better that the connecting condition with the current clock information source apparatus 2, 4. In this configuration, when the system 100 switches the connection during an imaging period, the reference time is changed. This may cause loss of synchronization between exposure and reading and result in an imaging failure. To avoid this, the operation mode may be switched to the free-running mode when the connection of the clock information source apparatus 2, 4 is changed during an imaging period. The operation mode is then returned to the synchronization mode after the imaging process ends.

The above-described imaging system 100 is an example in which both the controlling apparatus 12 and the imaging apparatus 3 have the function of switching the operation mode. However, it is only necessary that at least one of the controlling apparatus 12 and the imaging apparatus 3 has the function.

Flow of Serial Imaging

Next, the flow of a serial imaging process in the imaging system 100 of the embodiment that can switch the operation mode as described above will be described. FIG. 7 is a timing chart illustrating the operation of the imaging system 100 of the embodiment.

The imaging conditions in the illustrated example is as follows. The connection to the imaging apparatus 3 is wireless, the imaging mode is a serial imaging mode, and the frame rate is 15 fps. The flow is the same regardless of the imaging conditions.

In response to a user input of selecting the imaging conditions on the console 14, the console 14 sends the above-described imaging conditions to the imaging apparatus 3 via a wired communication network, the clock information source apparatus 2, 4 and wireless communication. The console 14 also sends the imaging conditions and irradiating conditions (a tube current, a tube voltage and an irradiation time) to the controlling apparatus 12. As used herein, the irradiation time refers to the irradiation time of each pulse of a pulsed irradiation. When the imaging apparatus 3 and the controlling apparatus 12 receive the imaging conditions and the irradiating conditions, they store the received conditions in the respective storage 35, 123 and start a process of wireless serial imaging.

Step 1

Then, the controlling apparatus 12 sets up the high voltage generator 122 with the received irradiating conditions via the controller 121. The system may be configured such that the user can input irradiating conditions on the operation interface 15. In this configuration, the controlling apparatus 12 sets up the high voltage generator 122 with the irradiating conditions input on the operation interface 15 via the controller 121. Until the first or second button of the exposure switch 15a is pressed down, the controlling apparatus 12 sets up the high voltage generator 122 via the controller 121 every time it receives new irradiating conditions from the console 14. This also applies to the system configuration in which the user can input irradiating conditions on the operation interface 15. Since the irradiating conditions are normally finely adjusted according to the body type of a patient, this configuration can improve the flexibility of the operation sequence and the usability of the system.

Step 2

Then, the imaging controller 31 and the radiation controller 121 sets the operation mode of the respective second clocks 39, 126 to the synchronization mode.

Step 3

The clock information source apparatus 2, 4 sends the first clock information to the imaging apparatus 3 and the controlling apparatus 12 periodically (normally every 100 ms). Specifically, the first clock information sent from the clock information source apparatus 2, 4 to the imaging apparatus 3 and the controlling apparatus 12 represents time or timing at the time of the sending.

When wireless communication is established between the clock information source apparatus 2, 4, and the imaging apparatus 3 and the controlling apparatus 12, the imaging apparatus 3 and the controlling apparatus 12 receive the first clock information from the clock information source apparatus 2, 4 to update their own respective clocks 37, 125 and then allow them to continue the counting operation.

Step 4

The imaging apparatus 3 and the controlling apparatus 12 constantly makes a determination as to whether the predetermined condition is met, i.e. whether their own respective clocks 37, 125 are in synchronization with the clock information source apparatus 2, 4 with required accuracy. The determination of the synchronization is made previously because when the synchronization accuracy is deteriorated during an imaging period, a time lag occurs between emission of radiation and reading of image data to cause an imaging failure.

Step 5

The imaging apparatus 3 and the controlling apparatus 12 share their respective determination results by sending them to each other. This allows the imaging apparatus 3 and the controlling apparatus 12 to detect the occurrence of an abnormality immediately, for example, when the first clock information has not been received from the clock information source apparatus 2, 4 for a long time, or when the first clock information of the clock information source apparatus 2, 4 is largely changed due to restart of the clock information source apparatus 2, 4 or the like.

Step 6

When the controller 121 of the controlling apparatus 12 detects a user operation of pressing down the second button of the exposure switch 15a (the controlling apparatus 12 receives the imaging start signal), it sends a corresponding signal to the high voltage generator 122 and shifts into a stand-by state to wait for the ready signal from the high voltage generator 122, representing the high voltage generator 122 is ready for irradiation.

When the high voltage generator 122 receives the imaging start signal, it starts preparation for irradiation. Specifically, the high voltage generator 122 prepares a voltage and a current to be output to the tube 13 and instructs the tube 13 to start rotation of a rotating anode.

When the rotation of the rotating anode reaches a predetermined speed, the tube 13 sends the ready signal to the high voltage generator 122. When the high voltage generator 122 has become ready for irradiation, it sends to the controller 121 a ready signal representing the high voltage generator 122 is ready for irradiation.

When the controller 121 receives the irradiation-ready signal, it sends to the imaging apparatus 3 via the communicator 124 a command representing the irradiating apparatus 1 is ready for irradiation.

Step 7

When the imaging apparatus 3 receives the command, it shifts into an imaging-ready state.

Then, the imaging apparatus 3 and the controlling apparatus 12 wait for the second clocks 39, 126 to update their own clock information to the clock information of the clocks 37, 125.

If the update of the clock information is not completed in a predetermined time, the console 14 may be informed of failure of the synchronization. The console 14 may then display a message or the like on a display (not shown) to inform the failure of the synchronization, to prompt the user to perform troubleshooting such as restart of the clock information source apparatus 2, 4 and checking the network configuration, or to recommend using a wired connection to take an image. This can speed up recovery from an abnormality.

When the update of the clock information of the second clocks 39, 126 is completed, the imaging apparatus 3 calculates an imaging sequence start time by adding an imaging sequence waiting time stored in the storage 35 to the clock information of the second clock 39 at the time of the completion. The imaging apparatus 3 stores the calculated imaging sequence start time in the storage 35 and sends it to the controlling apparatus 12.

The imaging sequence waiting time is predefined based on the expected delay time of the communication. Specifically, the imaging sequence waiting time is set to a time length of longer than the maximum probable delay time. This can prevent an imaging failure that occurs when the controlling apparatus 12 receives the imaging sequence start time after the time point specified by the imaging sequence start time due to a delay in sending the imaging sequence start time.

In the embodiment, the imaging apparatus 3 sends the imaging sequence start time to the controlling apparatus 12. Instead, the controlling apparatus 12 may calculates the imaging sequence start time by adding an imaging sequence waiting time stored in the storage 123 to the clock information of the second clock 126 at the time of completion of the update. In this case, the controlling apparatus 12 stores the calculated imaging sequence start time in the storage 126 and sends it to the imaging apparatus 3.

Step 8

Even after the synchronization with each other is completed, the imaging apparatus 3 and the controlling apparatus 12 continue to make a determination as to whether they are in synchronization with each other.

After the irradiation-ready signal is sent from the high voltage generator 122 to the controller 121, the imaging apparatus 3 and the controlling apparatus 12 may sometimes detect a failure of the synchronization in the period of time after the completion of the synchronization between the imaging apparatus 3 and the controlling apparatus 12 until the start of reading the last frame of the serial imaging process. In this case, the imaging apparatus 3 and the controlling apparatus 12 operate the second clocks 39, 126 in the free-running mode in the period of time after the detection until the start of reading the last frame of the serial imaging process, and then returns the operation mode to the synchronization mode. When the imaging apparatus 3 and the controlling apparatus 12 detects a failure of the synchronization, they switch the operation mode to the free-running mode before updating the clock information of the second clocks 39, 126 to the clock information of the clocks 37, 125. This can prevent the clock information of the second clocks 39, 126 from being set to an abnormal value.

Step 9

The controlling apparatus 12 which receives the imaging sequence start time from the imaging apparatus 3 stores it in the storage 123. Then, the controlling apparatus 12 generates exposure start times of the respective frames from the stored imaging sequence start time and the frame rate (e.g. 15 fps).

Specifically, the exposure start times are generated as follows. For example, the exposure start time of the first frame is set to the same time as the imaging sequence start time, and the imaging cycle time (=1/frame rate) is cumulatively added thereto to obtain the exposure start times of the second and later frames. That is, the exposure start time of the N-th frame=the imaging sequence start time+(frame number N−1)× the imaging cycle time.

The exposure start times may be generated beforehand and stored in the storage 123 so that they can be referenced every time an instruction to start exposure for each frame is received. Alternatively, the exposure start times may be generated one by one by adding the imaging cycle time to the exposure start time of a previous frame every time an instruction to start exposure for each frame is received. The latter configuration allows reduction of the capacity of the storage 123 and facilitates adapting the system when the number of frames in each imaging process varies.

Step 10

The controller 121 sends to the high voltage generator 122 a signal representing an instruction to start exposure for each frame image every time the clock information of the second irradiator clock 126 reaches any one of the exposure start times of the respective frame images.

The high voltage generator 122 controls the tube 13 to emit the radiation R for a preset irradiation time every time it receives the signal representing the instruction to start exposure. That is, the controlling apparatus 12 controls the tube 13 to emit the radiation R when the clock information of the second irradiator clock 126 reaches a first predetermined value.

Step 11

When the controller 121 detects the occurrence of an event indicating the end of the imaging process, e.g. the second button of the exposure switch 15a is released, the number of frame images taken reaches the maximum frame number stored in the storage 123, or the controller 121 receives a shut-down notification from the high voltage generator 122 or the imaging apparatus 3, it sends a command to notify the completion of the imaging process to the imaging apparatus 3 via the communicator 124 and does not send any further instruction to start exposure to the high voltage generator 122 during the current imaging process. That is, the imaging process ends.

The maximum frame number may be a fixed value stored in the storage 123. Alternatively, the maximum frame number may be a value that is input on the console 14 by the user, which is sent to the controlling apparatus 12 and stored in the storage 123.

Step 12

The imaging apparatus 3 generates reading start times of the respective frames based on the imaging sequence start time stored in the storage 123, the frame rate and the accumulation time of each frame.

In order to avoid exposure in a reading step, the accumulation time is longer than the irradiation time of each frame.

Specifically, the reading start times are generated as follows. For example, the reading start time of the first frame is set to the imaging sequence start time+ the accumulation time of each frame, and the imaging cycle time (=1/frame rate) is cumulatively added thereto to calculate the reading start times of the second and later frames. That is, the reading start time of the N-th frame=the imaging sequence start time+ the accumulation time of each frame+(frame number N−1)× the imaging cycle time.

The reading start times may be generated beforehand and stored in the storage 123 so that they can be referenced every time a frame is read. Alternatively, the reading start times may be generated one by one by adding the imaging cycle time to the reading start time of a previous frame every time a frame is read. The latter configuration allows reduction of the capacity of the storage 123 and facilitates adapting the system when the number of frames in each imaging process varies.

As described above, the imaging apparatus 3 generates the reading start times from the imaging sequence start time and the frame rate by itself while the controlling apparatus 12 generates the exposure start times similarly by itself. That is, the imaging sequence start time and the frame rate are only information that has to be shared between the imaging apparatus 3 and the controlling apparatus 12. This can reduce the risk of an imaging failure caused by communication delay between the imaging apparatus 3 and the controlling apparatus 12 due to a packet loss or the like. Such an imaging failure occurs when a reading start time is received after the time point specified by the reading start time, or when an exposure start time is received after the time point specified by the exposure start time.

Step 13

The imaging apparatus 3 starts reading charges accumulated in the radiation detector 32 to generate image data of a frame image every time the clock information of the second imager clock 39 reaches any one of the reading start times of the respective frames. That is, the imaging apparatus 3 reads image data of a radiographic image from the charges generated in the radiation detector 32 when the clock information of the second imager clock 39 reaches a second predetermined value.

Step 14

Then, the imaging apparatus 3 terminates the imaging process when it detects the occurrence of an event indicating the end of the imaging process, e.g. the imaging apparatus 3 receives a command to notify the completion of the imaging process from the controlling apparatus 12, or the number of frame images taken reaches the maximum frame number stored in the storage 35.

When the imaging apparatus 3 detects the occurrence of an event indicating the end of imaging process during a reading step, it preferably terminates the imaging process after completion of the reading step. This can prevent an abnormality that the frame image of the last frame is partly missing.

The above-described supplementary techniques include the following techniques.

1. A radiographic imaging system, comprising:
   a reference time apparatus comprising: a first clock which keeps time;
   a second clock and a third clock which respectively keep time;

a radiographic controlling apparatus which emits radiation from a radiation tube when a clock value of the second clock reaches a first predetermined value; and a radiographic imaging apparatus comprising: a radiation detector which generates charges when receiving radiation; and a reader which reads image data of a radiographic image based on the charges generated by the radiation detector when a clock value of the third clock reaches a second predetermined value, wherein the second clock and the third clock are capable of changing an own operation mode to a synchronization mode to perform synchronization to the first clock at predetermined timing, and wherein at least one of the second clock and the third clock
makes a determination as to whether a predetermined condition is satisfied, and
in response to determining that the predetermined condition is satisfied, switches the operation mode to a free-running mode to keep time without performing the synchronization to the first clock.

2. The radiographic imaging system according to claim 1, wherein at least one of the second clock and the third clock determines that the predetermined condition is satisfied when a predetermined event is detected during an imaging process.

3. The radiographic imaging system according to claim 2, wherein while the second clock and the third clock operate in the synchronization mode, the second clock and the third clock repeatedly perform synchronization to the first clock at predetermined intervals, and wherein at least one of the second clock and the third clock determines that the predetermined condition is satisfied when a length of time from a previous synchronization to a current synchronization exceeds each of the predetermined intervals.

4. The radiographic imaging system according to claim 2, wherein at least one of the second clock and the third clock determines that the predetermined condition is satisfied when an amount of change of a count value of said at least one of the second clock or the third clock by synchronization exceeds a predetermined threshold during an imaging process.

5. The radiographic imaging system according to claim 1, wherein at least one of the second clock and the third clock which operates in the free-running mode in an imaging process switches the own operation mode to the synchronization mode when the imaging process ends.

6. The radiographic imaging system according to claim 1, wherein the radiation controlling apparatus or the radiographic imaging apparatus which makes the determination as to whether the predetermined condition is satisfied and which switches the operation mode comprises a communicator which is capable of communicating with the reference time apparatus in a wireless manner.

7. The radiographic imaging system according to claim 6, wherein the communicator communicates with the reference time apparatus in a wireless manner according to an IEEE 802.11 standard, and wherein the second clock or the third clock which is provided in an apparatus comprising the communicator performs synchronization to the first clock by using a time synchronization function specified in the standard when the second clock or the third clock operates in the synchronization mode.

The above-described techniques can be used to stably perform a wireless serial imaging process.

EXAMPLES

Next, problems that can occur in the imaging systems 100, 100A, 100B of the above-described embodiments and specific examples for solving the problems will be described.

Example 1-1

The console 14 monitors the overall control of the imaging system 100, i.e. the operational state (which indicates whether a device is in a normal state or an abnormal state, whether a device is in a running state or a shutdown state, and the like) of the devices of the imaging system 100 or a device that mediates sending and receiving information to and from another system other than the imaging system 100. Further, the console 14 synchronizes the devices of the imaging system 100 and the device that mediates sending and receiving information to and from another system other than the imaging system 100. However, in the above-described embodiments, the clock information source apparatus 2, 4 is not connected to the console 14 but to the controlling apparatus 12. Accordingly, the console 14 has to perform processing such as synchronization check via the controlling apparatus 12, which results in the low efficiency of the processing.

Figure 22:
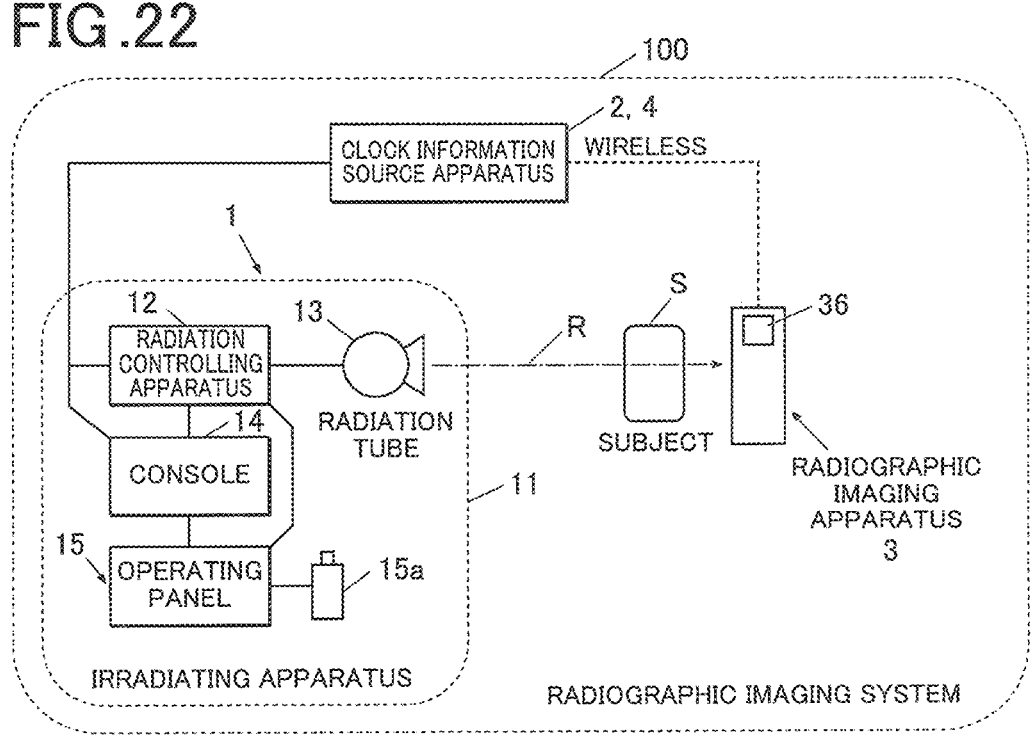
FIG. 22 is a block diagram of the radiographic imaging system according to Example 1-1, illustrating the configuration thereof.

To cope with the problem, for example, the clock information source apparatus 2, 4 may be connected to the console 14 as illustrated in FIG. 22. Since the clock information source apparatus 2, 4 is directly connected to the console 14, the console 14 can perform processing such as synchronization check with high efficiency.

While the clock information source apparatus 2, 4 is connected to the console 14, the clock information source apparatus 2, 4 may also be connected to the controlling apparatus 12. In this configuration, not only the console 14 but also the controlling apparatus 12 can be synchronized with the clock information source apparatus 2, 4. That is, the controlling apparatus 12 and the console 14 can individually be synchronized with the imaging apparatus 3.

Further, in this configuration, it may be checked as to whether there is a time lag between the operation of the controlling apparatus 12 and the operation of the console 14. When the synchronization cannot be performed between the clock information source apparatus 2, 4 and the controlling apparatus 12 or between the clock information source apparatus 2, 4 and the console 14 due to a communication failure or the like, the time lag between the operation of the controlling apparatus 12 and the operation of the console 14 is gradually increased. By detecting the time lag, it is possible to suspend the imaging process or to display a warning message.

Example 1-2

In the above-described embodiments, when the clock information source apparatus 2, 4 is connected to the controlling apparatus 12 or the console 14 in a wired manner, it is necessary to use a dedicated line since it is also necessary in order to synchronize them with each other.

Figure 23:
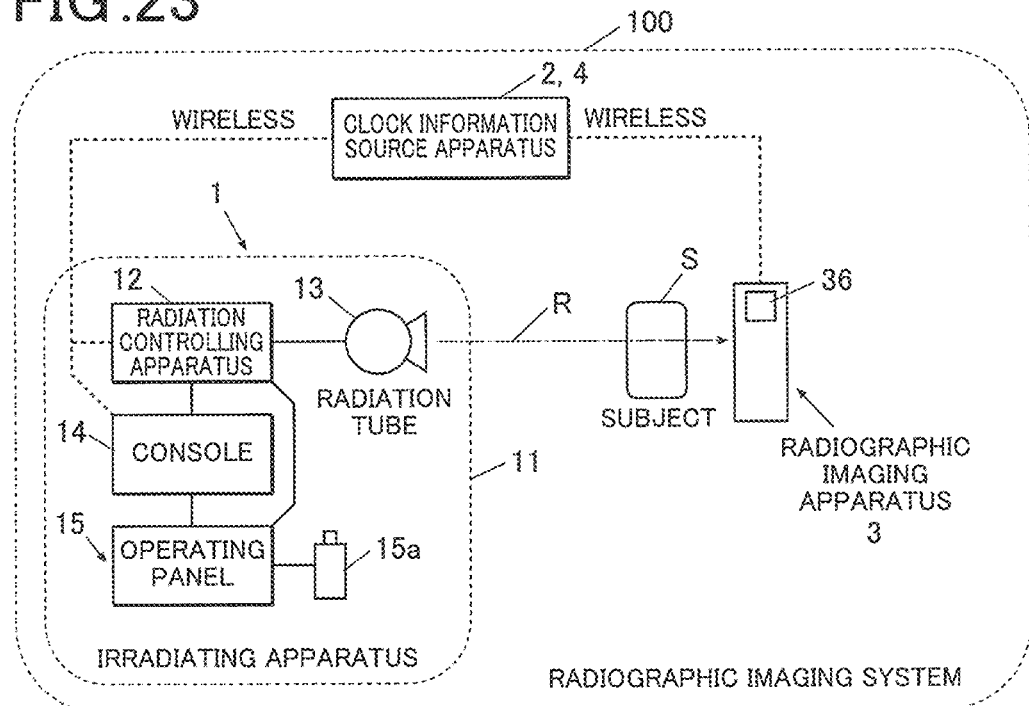
FIG. 23 is a block diagram of the radiographic imaging system according to Example 1-2, illustrating the configuration thereof.

To cope with the problem, in the above-described embodiments, the clock information source apparatus 2, 4 may be connected to the imaging apparatus 3 in a wireless manner, and the clock information source apparatus 2, 4 may also be connected to the controlling apparatus 12 in a wireless manner as illustrated in FIG. 23.

In this regard, the TSF specified in the communication standard IEEE 802.11 may be used to update the clock information of imager clock 37 of the imaging apparatus 3 to the clock information of the clock information source apparatus 2, 4 so as to perform synchronization of the clock information.

In this configuration, the same clock information can be used for synchronization between the clock information source apparatus 2, 4 and the imaging apparatus 3 and synchronization between the clock information source apparatus 2, 4 and the controlling apparatus 12. As a result, it is possible to perform the time synchronization without laying a cable around the subject S. Further, the same first clock information is used to update the clock information. This can reduce the operation lag between the controlling apparatus 12 and the imaging apparatus 3 and eliminate the necessity of an additional component for compensating asynchronization with other apparatuses. Further, the same radio wave is used to update the clock information. This can reduce the operation lag.

Instead between the clock information source apparatus 2, 4 and the controlling apparatus 12, the clock information source apparatus 2, 4 may be connected to the console 14 in a wireless manner for the synchronization.

Alternatively, the clock information source apparatus 2, 4 may be connected to the controlling apparatus 12 in a wireless manner while the clock information source apparatus 2, 4 may also be connected to the console 14 in wireless manner for the synchronization.

Example 1-3

In the above-described embodiments, the clock information source apparatus 2, 4 may be directly connected to the controlling apparatus 12. A problem in this configuration is that the arrangement of the clock information source apparatus 2, 4, the controlling apparatus 12 and the cable connecting them is sometimes limited.

Further, when the clock information source apparatus 2, 4 is directly connected to the controlling apparatus 12, the long distance of the wired connection may increase the occurrence of a communication failure between the clock information source apparatus 2, 4 and the controlling apparatus 12.

Figure 24:
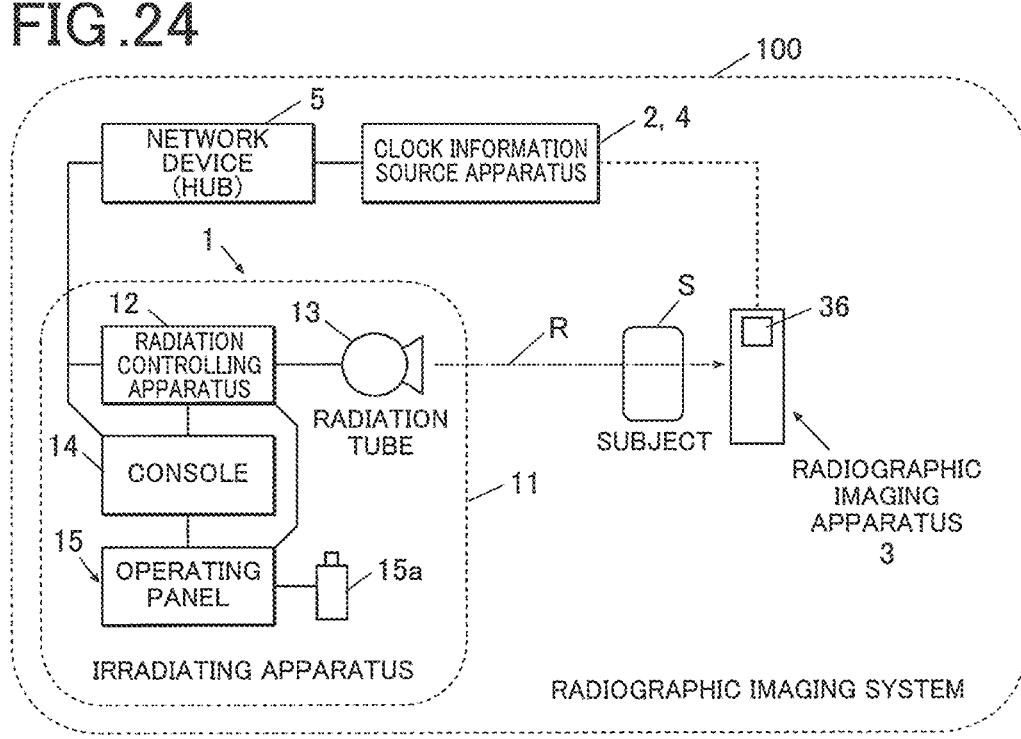
FIG. 24 is a block diagram the radiographic imaging system according to Example 1-3, illustrating the configuration thereof.

To cope with the problem, in the above-described embodiments, the radiation controlling apparatus may be connected to the clock information source apparatus 2, 4 via a network device 5 as illustrated in FIG. 24. For example, the network device 5 may be constituted by a hub.

In this regard, it is preferred to use a low-latency dedicated line for the connection between the clock information source apparatus 2, 4 and the network device 5 and between the network device 5 and the controlling apparatus 12, and to use the time synchronization of wired communication specified in IEEE 1588 for the synchronization between them.

This can reduce the limitation of the arrangement of the clock information source apparatus 2, 4, the controlling apparatus 12 and the cable.

Further, the connection via the network device 5 allows long-distance wired connection without intervention of any other device between the apparatuses. This can prevent degradation of communication signals and improve the reliability of the communication.

Example 1-4

In the above-described embodiments, the synchronization may be performed based on the clock information by using an external signal. A problem in this configuration is that it is impossible to make a determination as to whether the imaging apparatus 3 is in synchronization. Specifically, once wireless communication is lost due to radio wave interference or the like, the imaging apparatus 3 cannot inform the controlling apparatus 12 of the possibility of asynchronization in order to stop irradiation.

Figure 25:
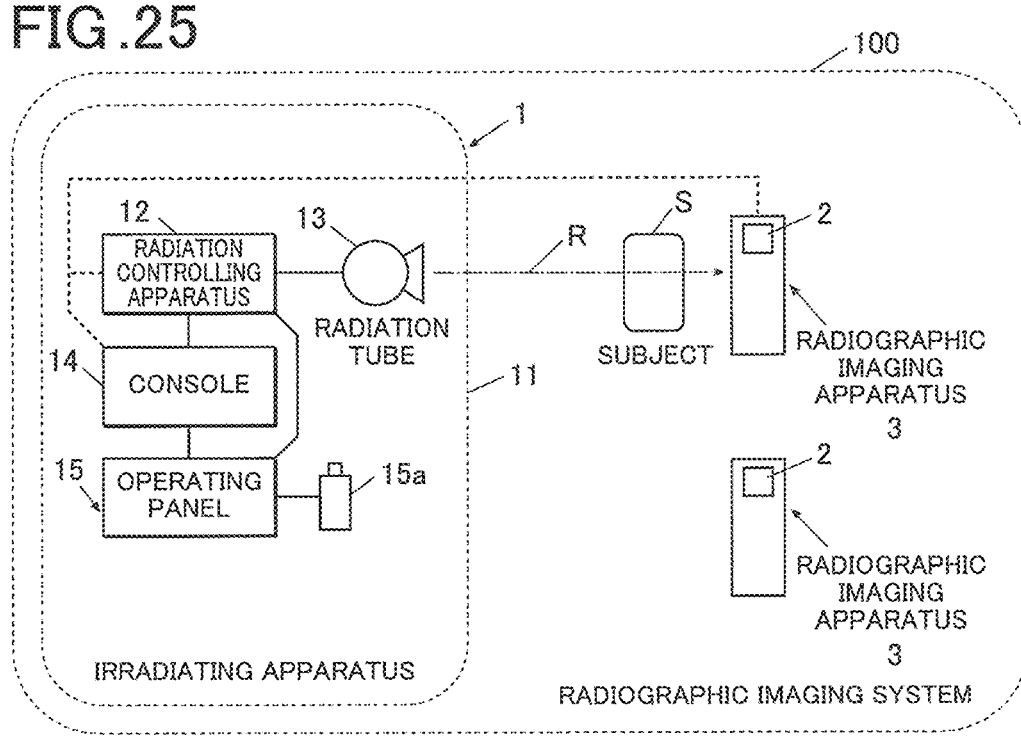
FIG. 25 is a block diagram of the radiographic imaging system according to Example 1-4, illustrating the configuration thereof.

To cope with the problem, in the above-described embodiments, the clock information source apparatus 2, 4 may be incorporated in the imaging apparatus 3, and the imaging apparatus 3 sends the first clock information to the controlling apparatus 12 for the synchronization as illustrated in FIG. 25.

Further, it is preferred that the controlling apparatus 12 includes a clock and performs the synchronization.

In this configuration, when the synchronization has not been performed for a certain period of time, the controlling apparatus 12 can understand the possible occurrence of an operation lag. Therefore, the controlling apparatus 12 can stop irradiation even when it cannot communicate with the imaging apparatus 3 in a wireless manner.

Further, it is not necessary to provide the intervening clock information source apparatus 2, 4. This can reduce the risk of communication delay due to a trouble of the clock information source apparatus 2, 4.

Example 1-5

In the above-described embodiments, the radiographic apparatus 12 may not support wireless communication. A problem in this configuration is that the time synchronization cannot be performed in wireless manner.

Figure 26:
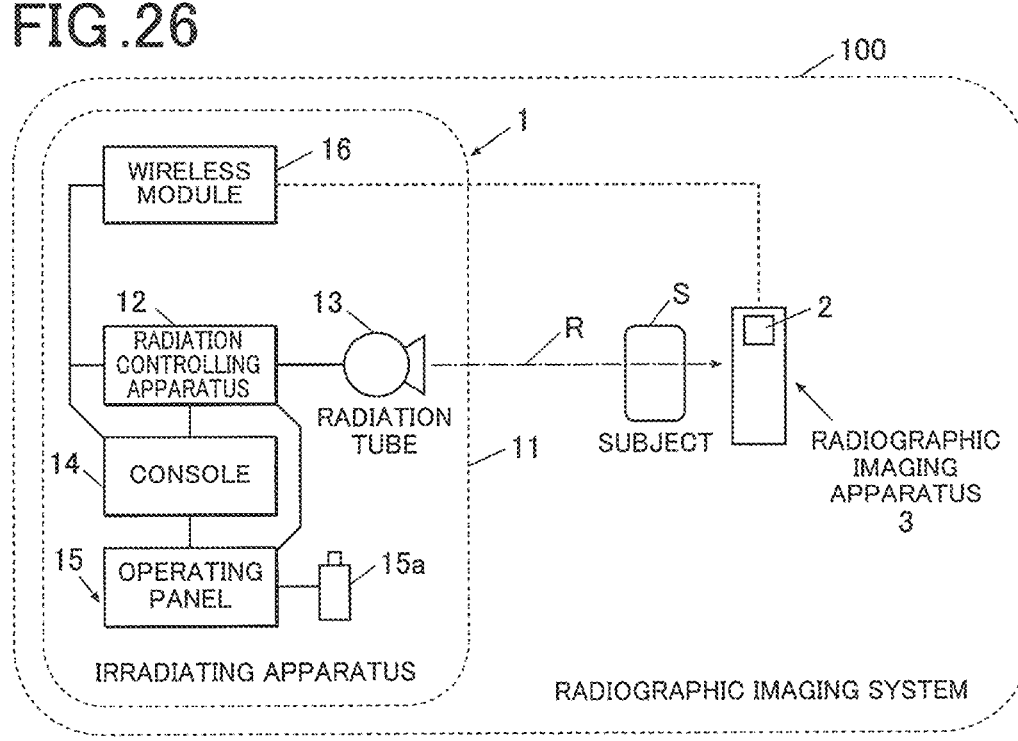
FIG. 26 is a block diagram of the radiographic imaging system according to Example 1-5, illustrating the configuration thereof.

To cope with the problem, in the above-described embodiments, a communication module 16 that can receive a radio wave from the clock information source apparatus 2, 4 may be connected to the controlling apparatus 12 as illustrated in FIG. 26. Then, the controlling apparatus 12 can receive the reference time from the clock information source apparatus 2, 4 via the communication module 16.

It is preferred to use a low-latency dedicated line for the connection between the communication module 16 and the controlling apparatus 12 and to use the time synchronization of wired communication specified in IEEE 1588.

This configuration enables wireless time synchronization even when the radiation controlling apparatus does not support wireless communication.

The communication module 16 only receives signals, and no radio signal is output from the communication module 16 or the irradiating apparatus 1. This can reduce the occurrence of a trouble relating to output of radio signals.

When it is not necessary to consider problems related to output of radio signals from the communication module 16 or the irradiating apparatus 1, the communication module can have a transmission function.

Example 1-6

In the above-described embodiments, when the user wants to compare a still image or a dynamic image obtained by the system with a measurement result or an output image obtained by an external apparatus, it is necessary to synchronize the imaging system 100 with the external apparatus in order to confirm that they are taken at the same timing. For example, when an image is taken in synchronization with heartbeats, it is necessary to take an image at the same timing of heartbeats, to extract an image taken at a certain time point in a heartbeat from serial images or to link serial images to heartbeat data. Accordingly, it is necessary to synchronize the time.

Figure 27:
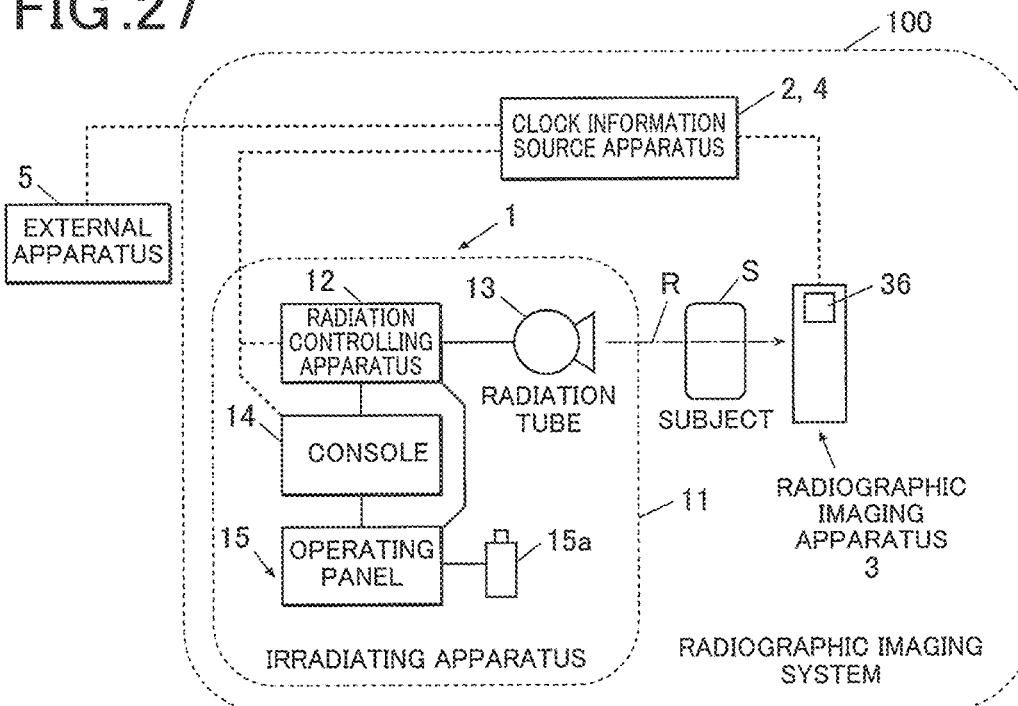
FIG. 27 is a block diagram of the radiographic imaging system according to Example 1-6, illustrating the configuration thereof.

To achieve this, in the present embodiments, the imaging system 100 may be connected to an external apparatus 6 by the same communicator as that between the clock information source apparatus 2, 4 and the controlling apparatus 12 or the imaging apparatus 3 as illustrated in FIG. 27, and the imaging system 100 may be synchronized with the external apparatus 6 based on the first clock information of the clock information source apparatus 2, 4.

This allows synchronized imaging with the external apparatus 5. For example, a heart rate monitor may be connected as the external apparatus 5. In this case, it is possible to take an image in synchronization with heartbeats by suitably controlling, storing and displaying the timing. It is also possible to know the timing of an obtained dynamic image with respect to heartbeats in order to make a diagnosis.

In addition to a heart rate monitor, a variety of devices may be used as the external apparatus 5 according to a subject to be radiographed, examples of which include a device for measuring a respiratory state such as a spirometer, a displacement sensor and an acceleration sensor for measuring a movement, and the like.

Any one of the external apparatus 5, the controlling apparatus 12 and the imaging apparatus 3 or all of them may include a storage for storing clock information.

By storing the clock information, it is possible to organize or extract an image and a measurement result obtained at the same time based on the clock information.

Example 1-7

In the above-described embodiments, the communicators send and receive data as well as the clock information for the synchronization. Problems in this configuration are the limited amount or speed of data communication, possible delay of data communication, and possible loss of data during communication.

Figure 28:
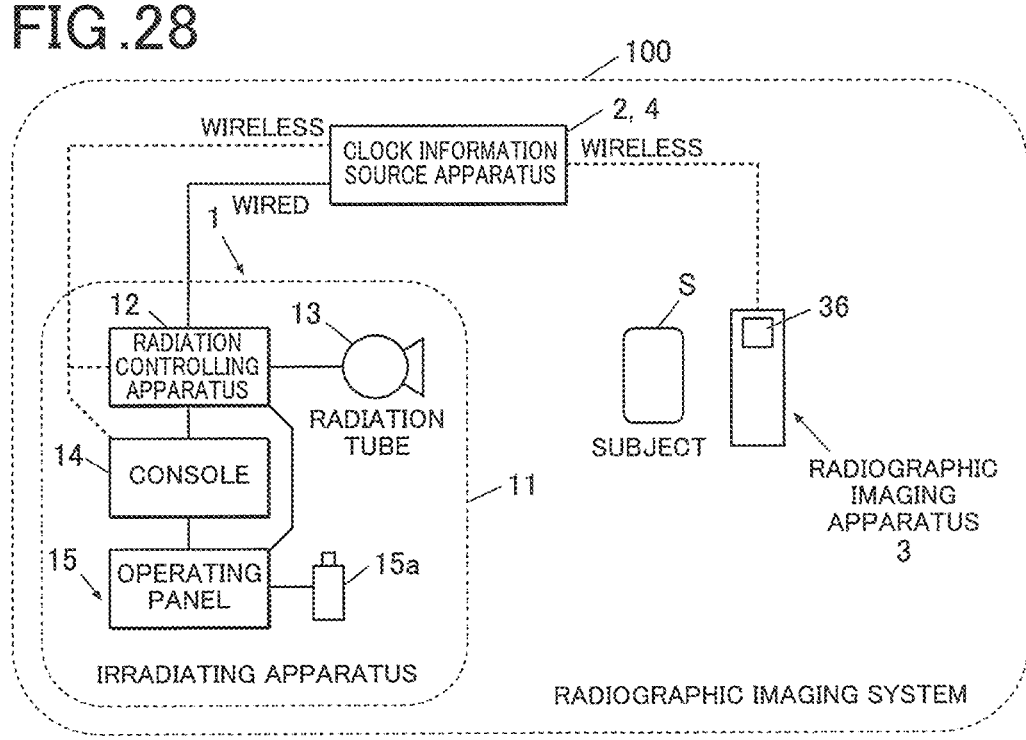
FIG. 28 is a block diagram of the radiographic imaging system according to Example 1-7, illustrating the configuration thereof.

To cope with the problems, in the above-described embodiments, the clock information source apparatus 2, 4 may be connected to the controlling apparatus 12 by two or more different communicator as illustrated in FIG. 28.

For example, the clock information source apparatus 2, 4 may be connected to the controlling apparatus 12 in a wireless manner to send and receive the clock information for synchronizing the time of the respective clock in a wireless manner. Furthermore, the clock information source apparatus 2, 4 is connected to the controlling apparatus 12 also in a wired manner (e.g. by Ethernet) to send and receive information other than the clock information for the time synchronization (e.g. irradiating conditions, irradiation time, etc.)

In this configuration, the communicator for the time synchronization can be separated from the communicator for sending and receiving information. As a result, a delay or loss of information does not occur, and it is possible to send and receive information at the same time with performing the time synchronization.

Further, it is possible to select suitable communicator respectively for the time synchronization and the sending and receiving of information.

Example 1-8

Figure 29:
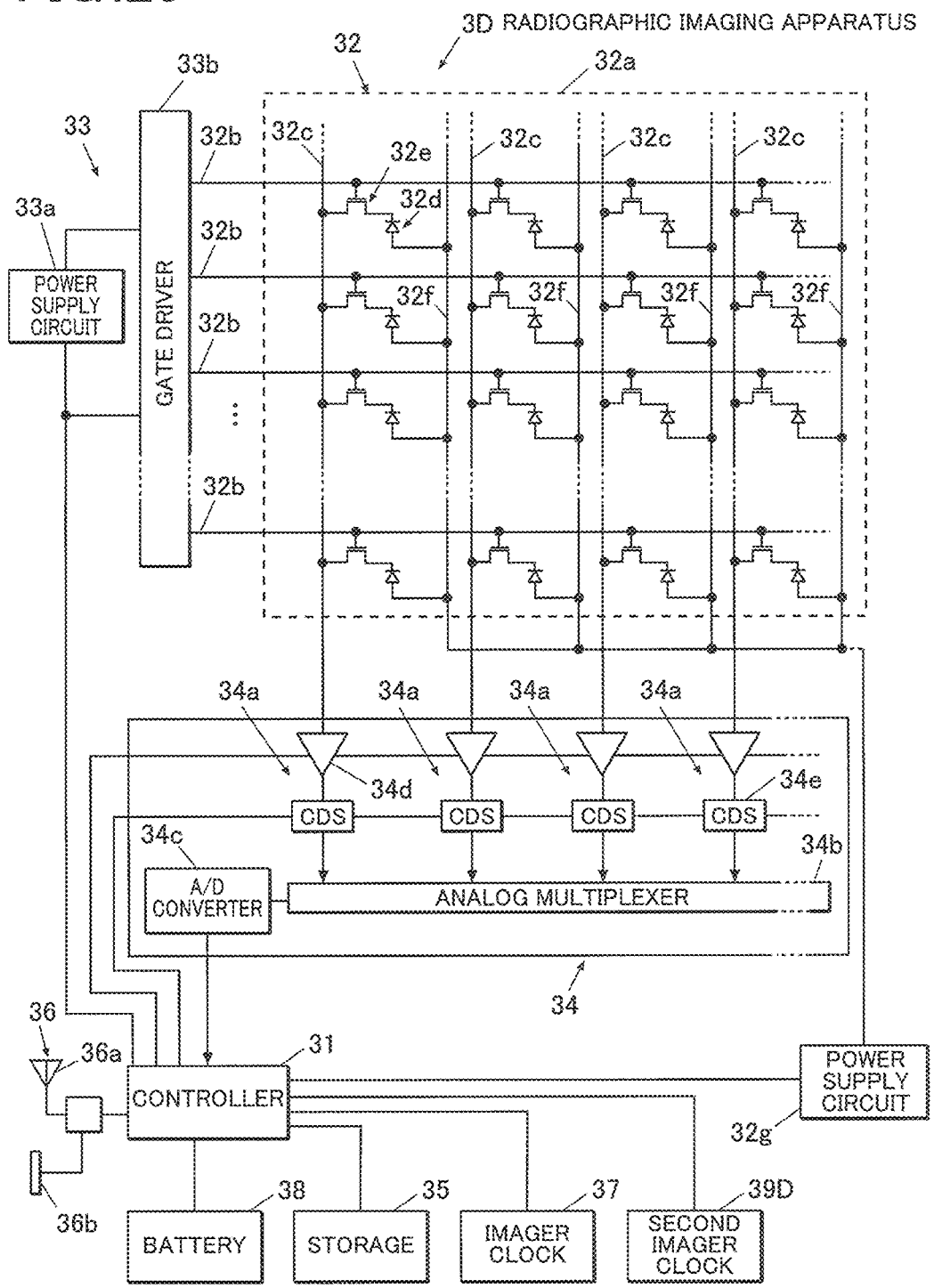
FIG. 29 is a block diagram of the radiographic imaging apparatus of the radiographic imaging system according to Example 1-8, illustrating the specific configuration thereof.

In the above-described embodiments, the imaging apparatus 3D may include another second imager clock 39D that is different from that in the above-described embodiments as illustrated in FIG. 29. For example, the second imager clock 39D may use an atomic clock, the GPS, an NTP or the like.

When an atomic clock or the GPS is used, the second imager clock 39D may include an antenna for receiving a radio wave.

By comparing the clock information of the imager clock 37 with the clock information of the second imager clock 39D at suitable timing, the system detects the time difference between the clock information of the imager clock 37 and the second imager clock 39D.

Figure 30:
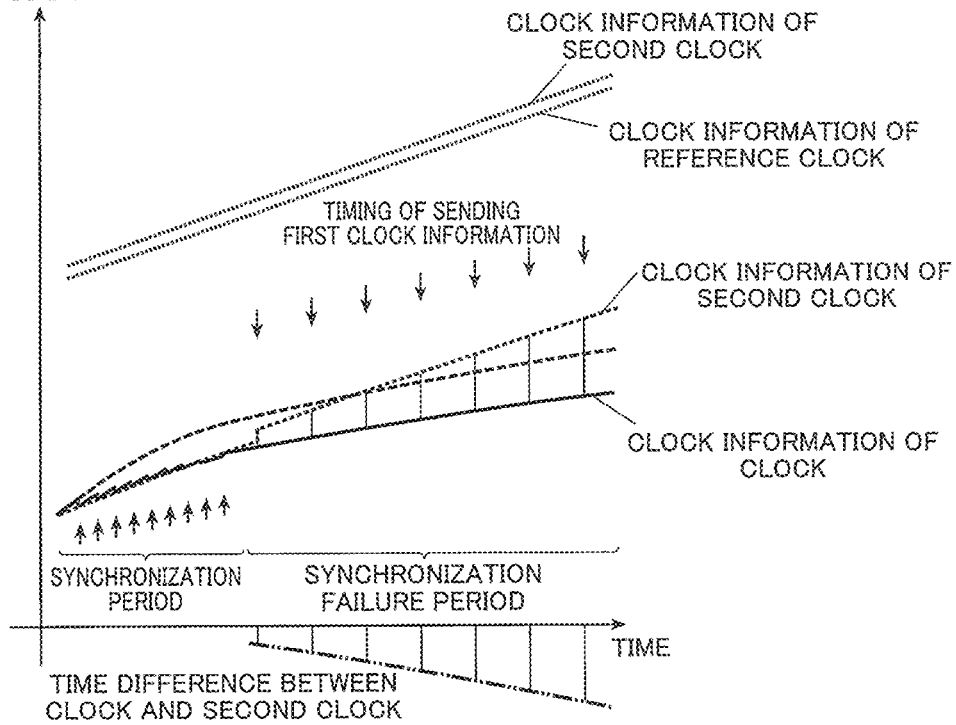
FIG. 30 is a timing chart of an operation of the radiographic imaging system that includes the radiographic imaging apparatus in FIG. 23.

In this configuration, even when the time difference between the first clock information of the clock information source apparatus 2, 4 and the second clock information of the imager clock 37 is gradually increased after the communication between the clock information source apparatus 2, 4 and the imaging apparatus 3 is lost as illustrated in FIG. 30, the imaging apparatus 3 can detect the occurrence of a time difference by comparing the clock information of the imager clock 37 with the clock information of the second imager clock 39D.

The imaging apparatus 3 may calculate the time difference (time lag) between the clock information of the respective clocks and make a determination as to whether the calculated difference is greater than a predetermined value. With this configuration, the imaging apparatus 3 can understand whether the accuracy of the time synchronization is sufficient. If the time difference is greater than the predetermined value, the system may perform the same output as in the above-described embodiment, such as giving a notification that the time difference is greater than the predetermined value, giving a notification that imaging is prohibi, or cancelling the imaging process.

FIG. 30 illustrates an example in which the second imager clock 39D is used to detect the time difference only in a synchronization failure period in which the synchronization between the imaging apparatus 3 and the clock information source apparatus 2, 4 cannot be performed. However, the second imager clock 39D may also be used to detect the time difference even in a synchronized period in which the synchronization with the clock information source apparatus 2, 4 is successfully performed.

Example 1-9

In Example 1-8, the imaging controller 31 may update the clock information of the imager clock 37 to the clock information of the second imager clock 39D or update the clock information of the second imager clock 39D to the clock information of the imager clock 37.

Figure 31:
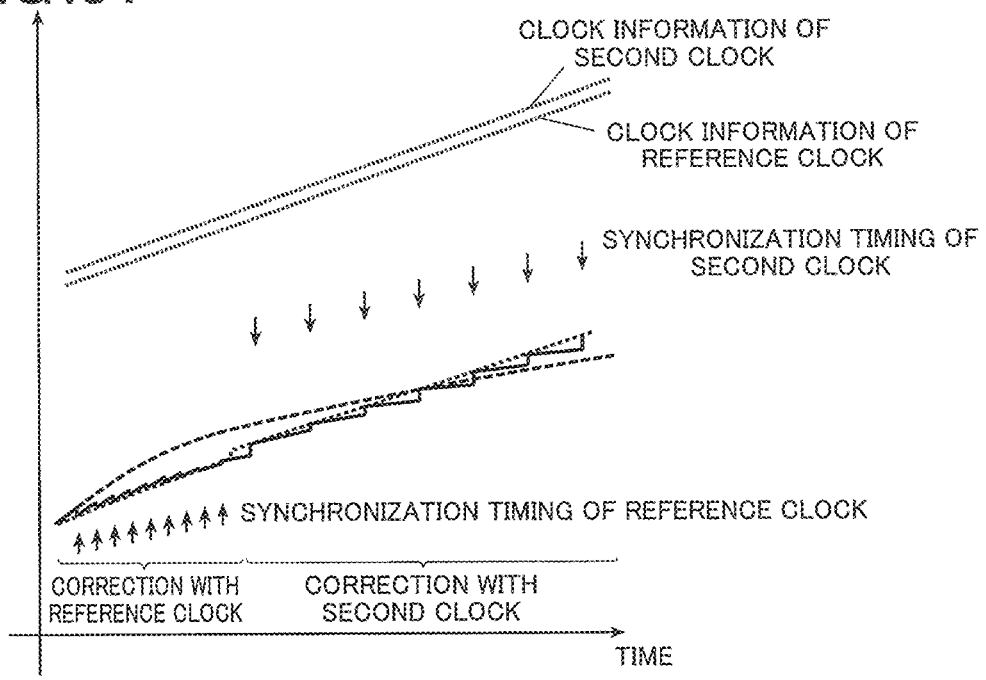
FIG. 31 is a timing chart of an operation of the radiographic imaging system according to Example 1-9.

As illustrated in FIG. 31, while communication is established between the clock information source apparatus 2, 4 and the imaging apparatus 3, the imaging apparatus 3 periodically update the clock information of the imager clock 37 by using the first clock information of the clock information source apparatus 2, 4. When it becomes impossible to perform the synchronization between the clock information source apparatus 2, 4 and the imaging apparatus 3, the imaging apparatus 3 periodically update the clock information of the imager clock 37 by using the clock information of the second imager clock 39D.

That is, even when the communication between the clock information source apparatus 2, 4 and the imaging apparatus 3 is lost, the imaging apparatus 3 can continue the time synchronization with the clock information source apparatus 2, 4 to continue the imaging process.

FIG. 31 illustrates an example in which the second imager clock 39D is used to update the clock information of the imager clock 37 only while the communication between the clock information source apparatus 2, 4 and the imaging apparatus 3 is lost. However, the second imager clock 39D may also be used to update the clock information of the imager clock 37 even while the synchronization with the clock information source apparatus 2, 4 is successfully performed.

Example 1-10

In Example 1-8 and Example 1-9, a measuring unit may be provided to measure the reliability of communication between the second imager clock 39D and the outside.

For example, when the second imager clock 39D uses a radio wave, e.g. uses an atomic clock or the GPS, a device that measures the intensity of the radio wave may be provided as the measuring unit.

The imaging controller 31 periodically compares the measurement value of the device with a predetermined value. When the measurement value is less than the predetermined value, the imaging controller 31 determines that the reliability of the communication is insufficient. Then, the imaging controller 31 performs an output such as giving a notification to the user that the reliability of the second imager clock 39D is low, giving a notification that imaging is disabled, or cancelling the imaging process.

This can prevent an image from being erroneously taken when the reliability of the communication of the second imager clock 39D is low. The subject S can thus be prevented from being exposed to unnecessary radiation.

Example 1-11

Figure 32:
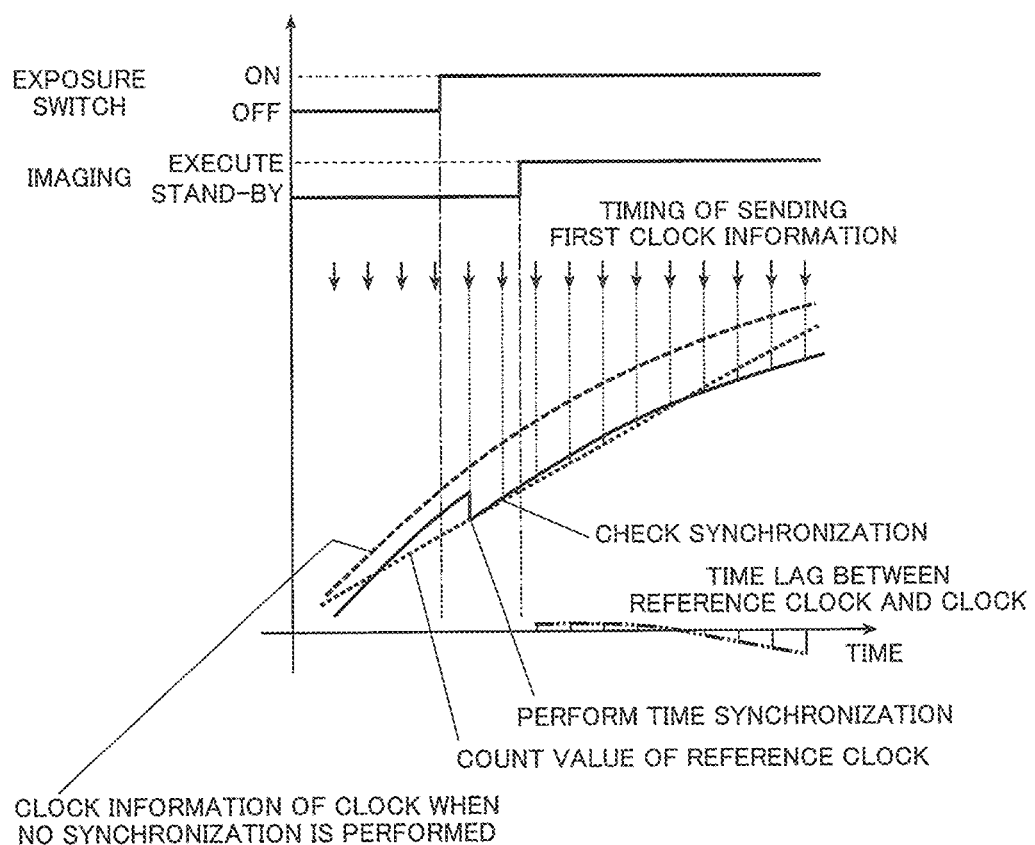
FIG. 32 is a timing chart of an operation of the radiographic imaging system according to Example 1-11.

In the above-described embodiments, the clock information may be updated only before the start of an imaging period (before the state changes from a stand-by state to an operational state). During the imaging period, the clock information may not be updated, but the time difference (time lag) between the first clock information of the clock information source apparatus 2, 4 and the clock information of the imager clock 37 may only be monitored, for example, as illustrated in FIG. 32.

The difference may be monitored at the timing of the time synchronization between the clock information source apparatus 2, 4 and the imaging apparatus 3 (the timing of sending the first clock information of the clock information source apparatus 2, 4) or at predetermined timing of the imager clock 37.

The difference may be monitored at both the timing of the time synchronization of the clock information source apparatus 2, 4 and the predetermined timing of the imaging apparatus 3. In this configuration, the time difference can be monitored even when any of the clock information source apparatus 2, 4 and the imager clock 37 have a trouble.

When the second imager clock 39D as described in Example 1-9 to Example 1-11 is provided, the difference between the clock information of the imager clock 37 and the clock information of the second imager clock 39D may be monitored instead. In this configuration, the time difference may be monitored at predetermined timing of the second imager clock 39D.

Example 1-12

In the above-described embodiments, the communicator 36 or the imaging controller 31 of the imaging apparatus 3 may have a monitoring function of monitoring whether the communication is maintained in a normal condition.

When the imaging controller 31 or the communicator 36 having the monitoring function detects loss of the communication, it determines that the communication is not maintained in a normal condition. Then, the imaging controller 31 or the communicator 36 performs an output such as giving a notification to the user that the communication is lost, giving a notification that imaging is disabled, or cancelling the imaging process.

This can prevent an image from being erroneously taken when the communication is not maintained in a normal condition. The subject S can thus be prevented from being exposed to unnecessary radiation.

Example 2-1

Another problem in the above-described embodiments is that a desired result is not obtained and imaging fails when the system starts taking an image without checking whether the apparatuses are in synchronization with each other. An imaging failure requires another imaging, and the subject S is exposed to unnecessary radiation.

Figure 33:
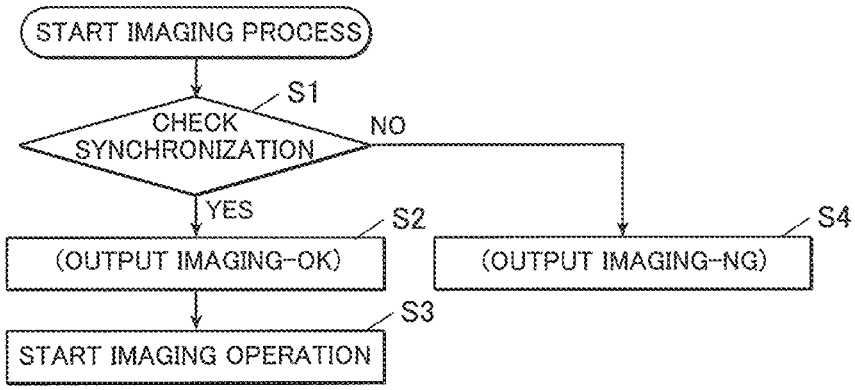
FIG. 33 is a flowchart of an operation of the radiographic imaging system according to Example 2-1.

To cope with the problem, in the above-described embodiments, the time synchronization may be checked at the start of taking an image as illustrated in FIG. 33, e.g. when the user presses down the exposure switch (Step 1). If the accuracy of the time synchronization is at a desired level or more (Step S1, Yes), imaging is enabled (Step S2) and the imaging process starts (Step S3). If the accuracy of the time synchronization is insufficient (Step S1, No), the system takes a measure such as giving to the user a notification that the apparatuses are out of synchronization, giving a notification that imaging is disabled, or cancelling the imaging process (Step S4).

It is preferred that whether to give the notification to the user or to give the notification that imaging is disabled is selected according to the amount of time difference.

This can prevent an image from being erroneously taken when the apparatuses are not in synchronization. The subject S can thus be prevented from being exposed to unnecessary radiation.

Example 2-2

Figure 34:
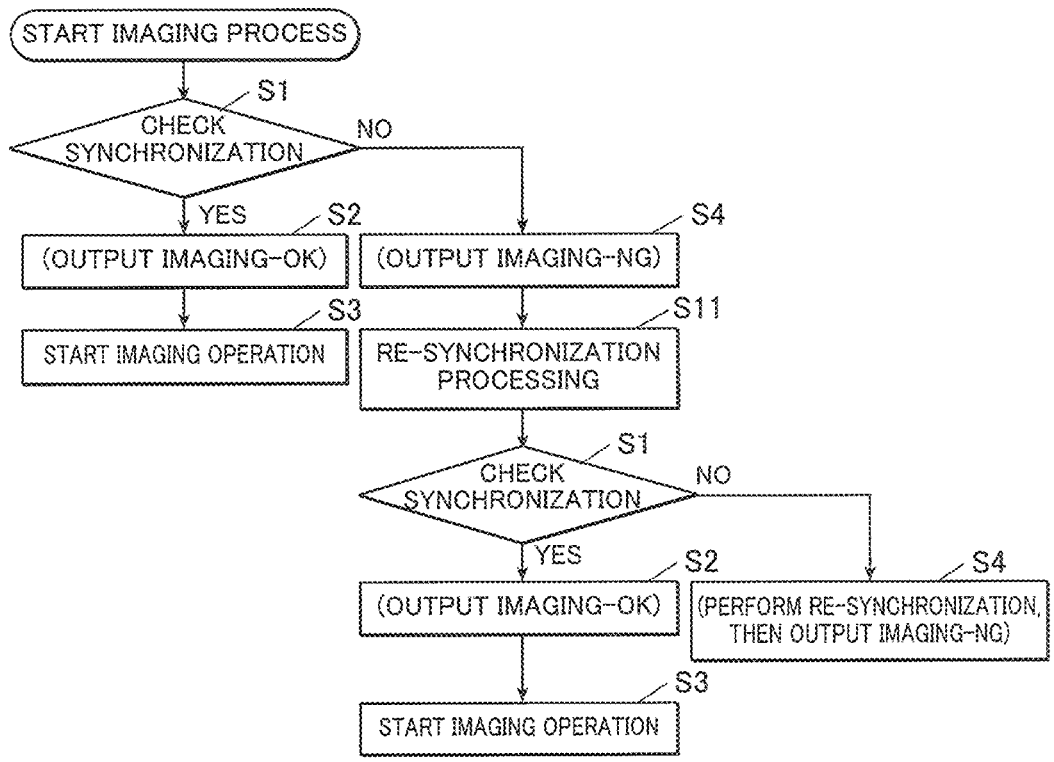
FIG. 34 is a flowchart of an operation of the radiographic imaging system according to Example 2-2.

In Example 2-1, the synchronization (Step S11) may be performed after Step S4, and thereafter the processing of Step S1 to Step S4 is repeated as illustrated in FIG. 34.

When the synchronization is performed again, a notification may be given or the imaging process may be canceled.

It is preferred that whether to give the notification to the user or to give the notification that imaging is disabled is selected according to the amount of time difference.

This can prevent an image from being erroneously taken when the apparatuses are not synchronized. The subject S can thus be prevented from being exposed to unnecessary radiation.

Example 2-3

Figure 35:
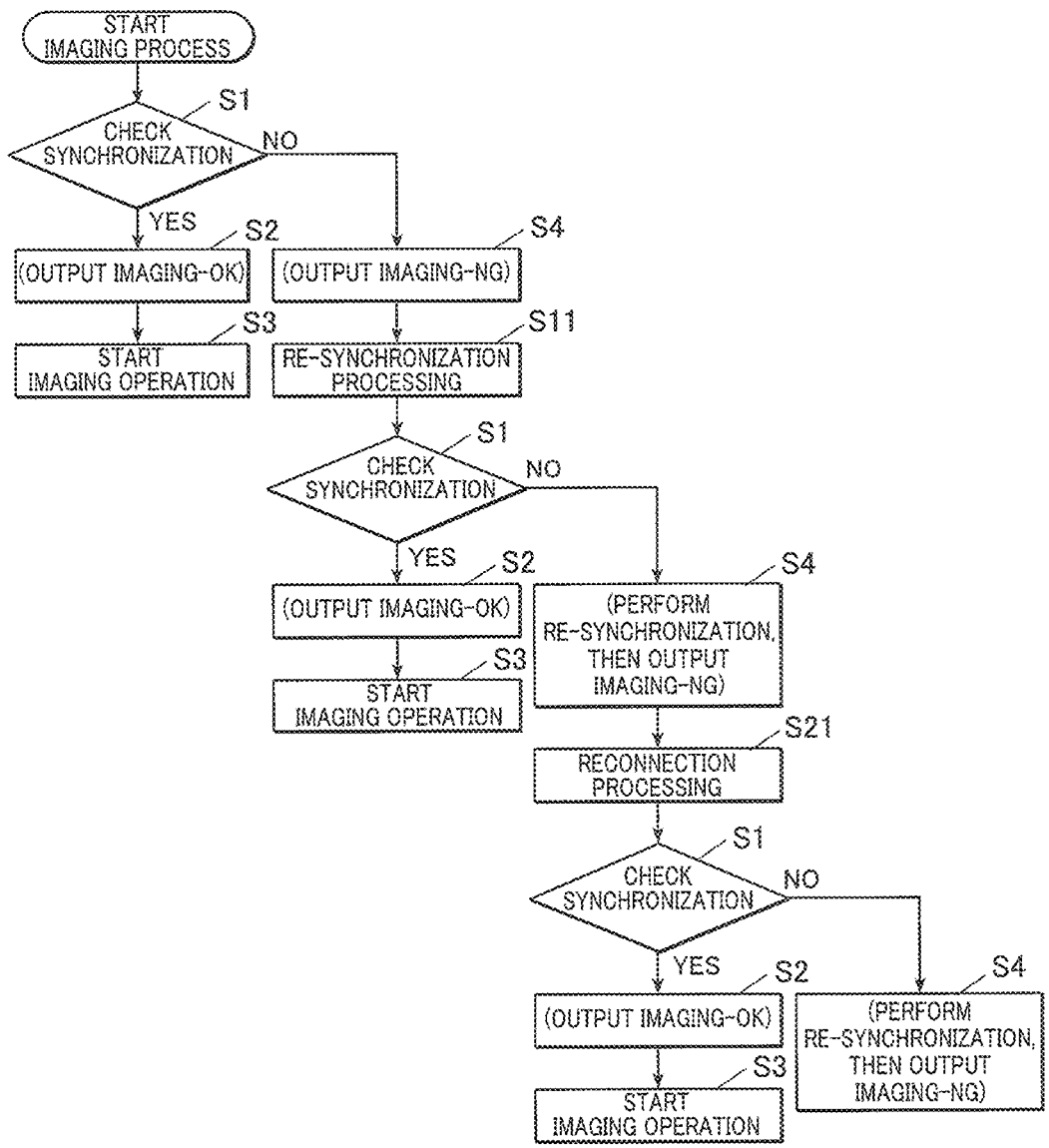
FIG. 35 is a flowchart of an operation of the radiographic imaging system according to Example 2-3.

In Example 2-2, the clock information source apparatus 2, 4 may be reconnected to the controlling apparatus 12 and the imaging apparatus 3 (Step S21) after the second Step S4, and thereafter the processing of Step S1 to S4 may be repeated again as illustrated in FIG. 35.

When the accuracy of the time synchronization is insufficient even after the communication is disconnected and then reconnected, it is preferred that the system takes measures such as giving to the user a notification that the apparatuses are not synchronized, giving a notification that imaging is disabled, or cancelling the imaging process.

It is preferred that the determination as to whether to give the notification to the user or the determination as to whether to give the notification that imaging is disabled is made based on the amount of time difference.

This can prevent an image from being erroneously taken when the apparatuses are not synchronized. The subject S can thus be prevented from being exposed to unnecessary radiation.

Example 2-4

Figure 36:
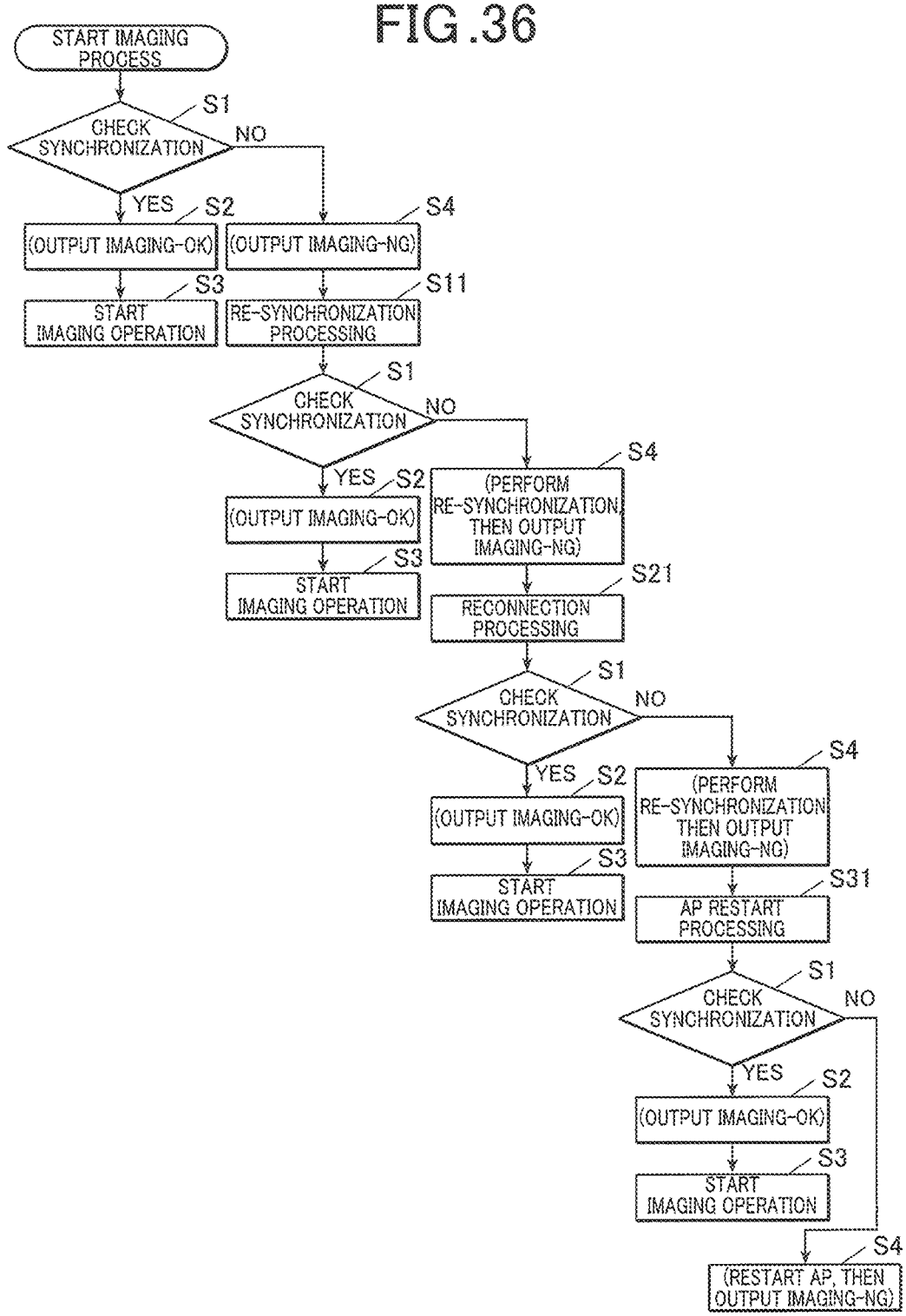
FIG. 36 is a flowchart of an operation of the radiographic imaging system according to Example 2-4.

In Example 2-3, the clock information source apparatus 2, 4 may be restarted (Step S31) after the third Step S4, and thereafter the processing of Step S1 to Step S4 is repeated again as illustrated in FIG. 36.

When the accuracy of the time synchronization is insufficient even after the clock information source apparatus 2, 4 is turned off and is then restarted and reconnected, it is preferred that the system takes measures such as giving to the user a notification that the apparatuses are not synchronized, giving a notification that imaging is disabled, or cancelling the imaging process.

It is preferred that whether to give the notification to the user or to give the notification that imaging is disabled is selected according to the amount of time difference.

This can prevent an image from being erroneously taken when the apparatuses are not synchronized. The subject S can thus be prevented from being exposed to unnecessary radiation.

Example 2-5

Another problem in the above-described embodiments is that even when the user wants the system to perform the synchronization at desired timing, there is no way for the user to input the instruction.

Figure 37:
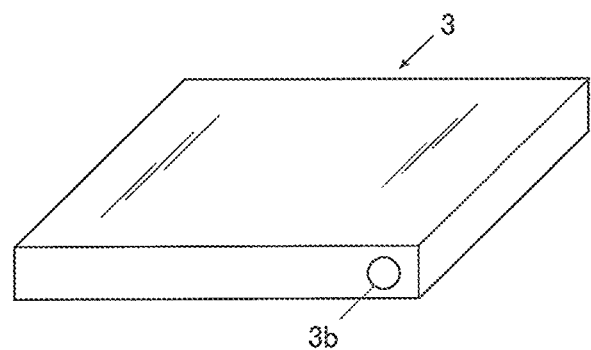
FIG. 37 is a perspective view of the radiographic imaging apparatus of the radiographic imaging system according to Example 2-5.

To cope with the problem, in the above-described embodiments, the imaging apparatus 3 may be provided with a specific operation button 3b as illustrated in FIG. 37. In response to a user operation of pressing down the operation button 3b, the system performs the synchronization processing.

In this configuration, the time synchronization between the imaging apparatus 3 and the clock information source apparatus 2, 4 can be performed at the timing desired by the user.

The system may be configured to perform the time synchronization in response to a specific user operation such as holding down the operation button 3b for a long time or pressing the operation button 3b multiple times.

In this configuration, another button that is originally installed for a different purpose can also be used as the operation button 3b, and it is not necessary to excessively increase the number of buttons of the imaging apparatus 3.

Example 3-1

Another problem in the above-described embodiments is that the system continues an imaging process even when a large time lag occurs between the operation of the irradiating apparatus 1 and the operation of the imaging apparatus 3. This results in an imaging failure, and the subject S is exposed to unnecessary radiation.

To cope with the problem, in the above-described embodiments, the system may give a notification or cancel the imaging process according to the difference (the amount of time difference) between the first clock information of the clock information source apparatus 2, 4 and the second clock information of the imager clock 37 of the imaging apparatus 3.

Specifically, the imaging controller 31 or the like may have a function of comparing the amount of time difference with a predetermined threshold. When the time difference exceeds the threshold, the system displays a warning to the user or stops irradiation to cancel the imaging process.

This can prevent an image from being taken when the apparatuses are not synchronized. The subject S can thus be prevented from being exposed to unnecessary radiation.

Figure 38:
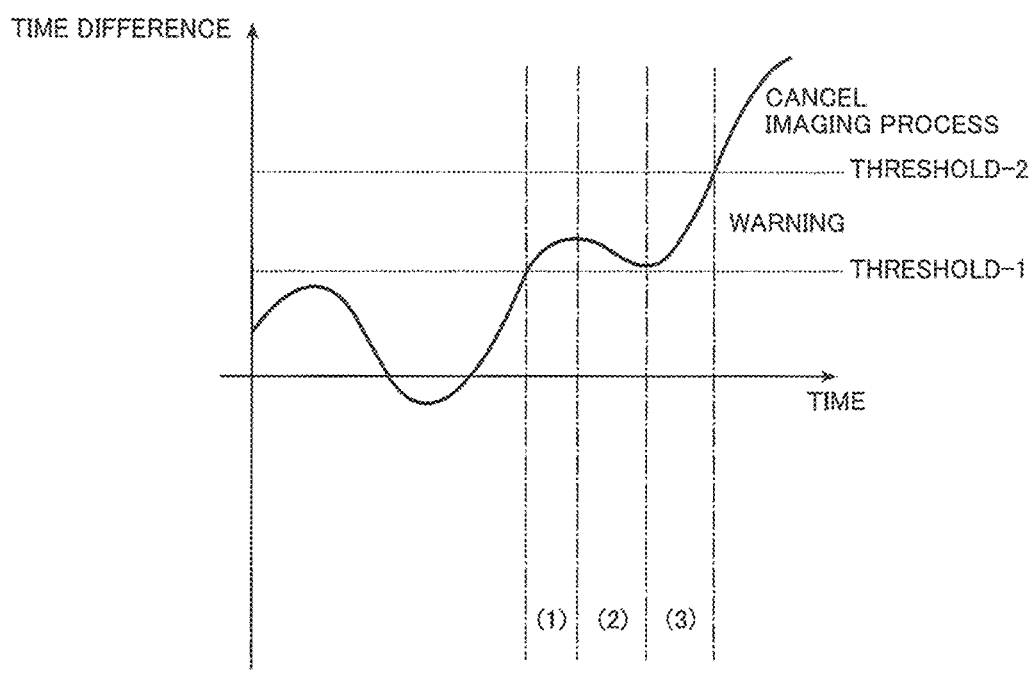
FIG. 38 is a graph illustrating an operation of the radiographic imaging system according to Example 3-1.

Two (higher and lower) thresholds may be set as illustrated in FIG. 38. When the time difference exceeds the first (lower) threshold, the system gives a warning. Then, when the time difference exceeds the second (higher) threshold, the system cancels the imaging process.

The system may be configured not to display the warning when the time difference is greater than the first threshold but is on a decreasing trend as in the time range (2).

Example 3-2

As described in Example 3-1, there is a problem that the system continues an imaging process even when a large time lag occurs between the operation of the irradiating apparatus 1 and the operation of the imaging apparatus 3 in the above-described embodiments. To cope with the problem, in Example 3-1, the system gives the notification to the user or cancels the imaging process according to the amount of actual time difference. Instead, the system may predict a future time difference and give a notification to the user or cancel imaging process according to the amount of predicted future time difference.

Specifically, the relationship between the imaging time (the number of images taken) in a past imaging process and the difference (the amount of time difference) between the first clock information of the clock information source apparatus 2, 4 and the second clock information of the imager clock 37 is stored in the storage 31.

The imaging controller 31 has a function of predicting the amount of time difference when the number of images taken reaches the preset number of the current imaging process based on the stored relationship between the imaging time and the amount of time difference in the past, a function of comparing the predicted time difference with a predetermined threshold, and a function of performing an output when it is determined that the predicted amount of time difference is greater than the threshold, such as giving a notification that there is a possibility of imaging failure due to loss of synchronization when the imaging process is continued to the last, giving a notification that imaging is disabled, or cancelling the imaging process.

This can prevent an image from being taken when the apparatuses are not synchronized and thereby reduce the risk that the subject S is exposed to unnecessary radiation.

Figure 39:
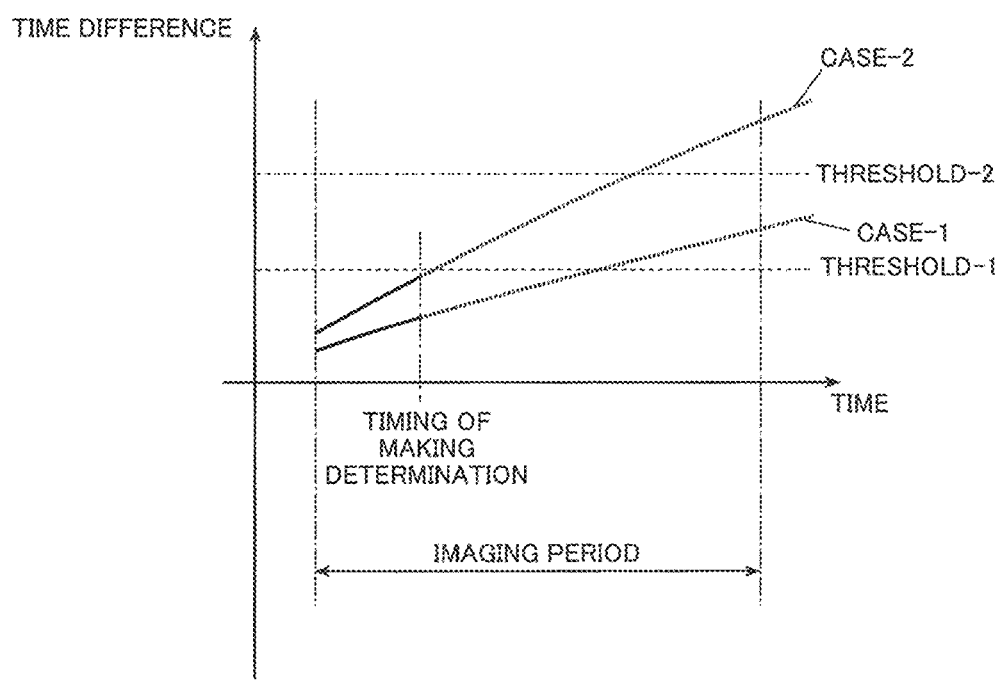
FIG. 39 is a graph illustrating an operation of the radiographic imaging system according to Example 3-2.

As illustrated in FIG. 39, two (lower and higher) thresholds may be set. When the predicted time difference is greater than the first (lower) threshold but lower than the second (higher) threshold as in Case 1, i.e. it is determined that the time difference does not largely affect the imaging process, the system may give a warning. When the predicted time difference is clearly greater than the second threshold, i.e. the imaging will certainly fail if the imaging process is continued to the last, the system may give to the radiographer a notification that there is a possibility that the time difference will be increased to such a level that affects the image by the end of the imaging period or the system may cancel the imaging process.

Example 3-3

Even when the time difference (time lag) between the first clock information of the clock information source apparatus 2, 4 and the second clock information of the imager clock 37 is greater than a certain threshold, it is sometimes possible to obtain an image that can be used for diagnosis. In the above-described embodiments, the system automatically cancels the imaging process or gives a notification to prompt the user to cancel the imaging process when the time difference exceeds the threshold. A problem in this configuration is that once the time difference exceeds the threshold, the images that have been already taken become useless. As a result, the subject S may be exposed to unnecessary radiation.

To cope with the problem, in the above-described embodiment, the system may continue an imaging process until a preset number of images are taken even when the time difference exceeds a threshold. After the completion of the imaging process, the system may give a notification that the time difference exceeded a threshold.

Specifically, the imaging controller 31 has a function of comparing the time difference (time lag) between the first clock information of the clock information source apparatus 2, 4 and the second clock information of the imager clock 37 with a predetermined threshold.

Further, the imaging controller 31 has the following function. When the imaging controller 31 determines that the time difference has exceeded the threshold, it stores the determination result and notifies it to the user during or after the imaging period.

In this configuration, it is possible to obtain an image that can be used for diagnosis even when the time difference reaches a certain level. This can reduce the risk that the subject S is exposed to unnecessary radiation.

When the time difference exceeds the threshold, the imaging controller may store the period of time in which the time difference is greater than the threshold and associate specific information (flag or the like) with the image data of an image that is taken in the period of time in which the time difference is greater than the threshold. When the images are checked afterwards, this enables specifying which image was taken while the time difference was greater than the threshold.

Figure 40:
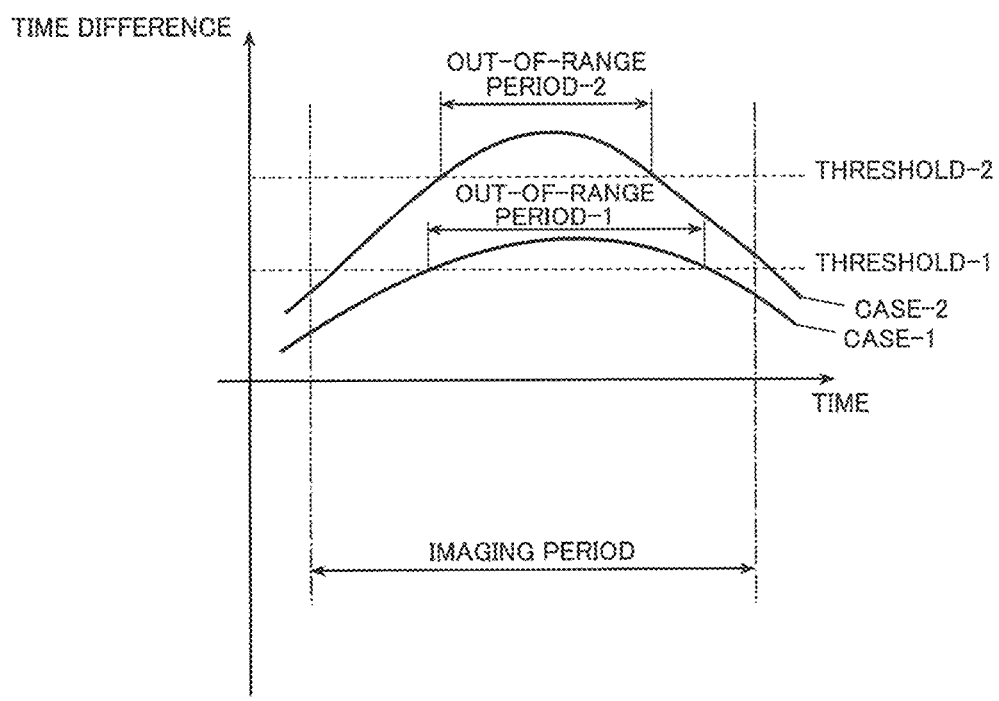
FIG. 40 is a graph illustrating an operation of the radiographic imaging system according to Example 3-3.

Two (lower and higher) thresholds may be set as illustrated in FIG. 40. The imaging controller 31 may store the period of time in which the time difference is greater than the first (lower) threshold as in Case 1, i.e. the time difference is at a warning level, and the period of time in which the time difference is greater than the second (higher) threshold as in Case 2, i.e. the time difference is at such a high level that requires cancelling the imaging process.

Example 4-1

Another problem in the above-described embodiments is that since the alignment between the first clock information of the clock information source apparatus 2, 4 and the clock information of the imager clock 37 is performed at a moment, the clock information is sometimes changed greatly by the update to cause a trouble.

For example, when the clock information is changed greatly to pass through the timing of two or more events, operations such as irradiation, accumulation of charges, reading and transfer are performed at the same time, which causes a trouble such as an imaging failure.

To cope with the problem, in the above-described embodiments, when it is necessary to update the clock information in an imaging period, the clock information may be aligned and synchronized not at a moment but gradually.

Specifically, every time the first clock information is sent or received, the first clock information of the clock information source apparatus 2, 4 or the second clock information of the imager clock 37 is updated such that the time difference (time lag) between them is reduced little by little.

Figure 41:
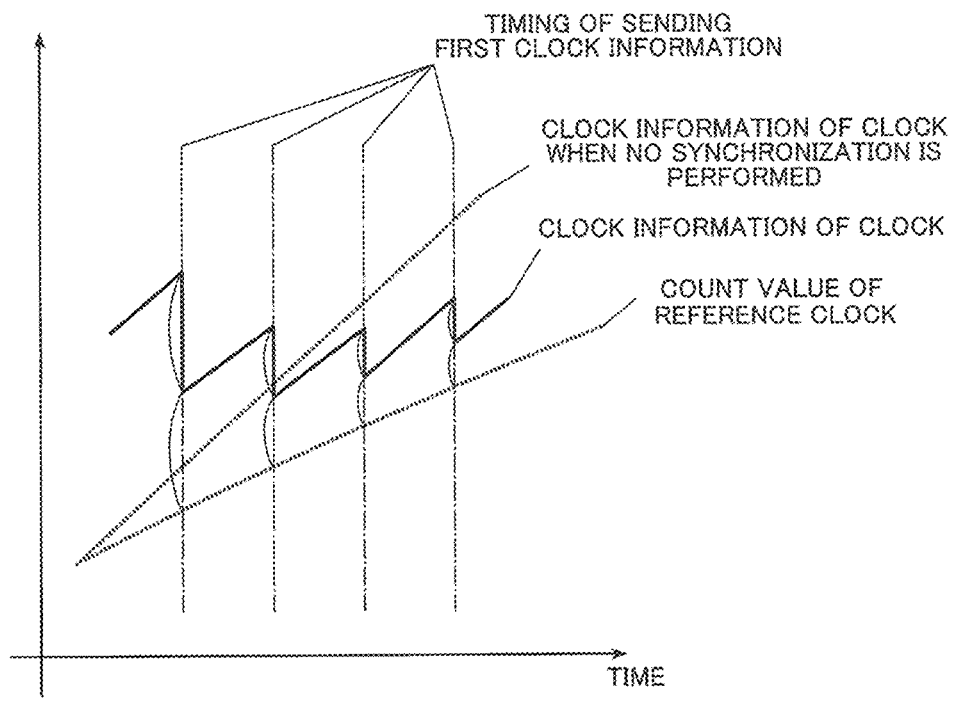
FIG. 41 is a graph illustrating an operation of the radiographic imaging system according to Example 4-1.

For example, the term "little by little" means a predetermined percentage (e.g. x %) of the time difference or a predetermined fraction (e.g. a fraction of x) of the time difference as illustrated in FIG. 41.

This configuration can prevent problems related to a large change of the clock information.

However, when the time difference is large, such gradual reduction of the time difference may sometimes require a lot of time until the time difference is reduced to such a level that does not affect output images.

To avoid this, the amount of change of the clock information per correction may be increased according to the amount of time difference.

Example 4-2

Another problem in the above-described embodiments is that since the alignment between the first clock information of the clock information source apparatus 2, 4 and the clock information of the imager clock 37 is performed at a moment, the clock information is sometimes decreased (the time represented by the clock information goes back) by the update to cause a trouble.

Figure 42A:
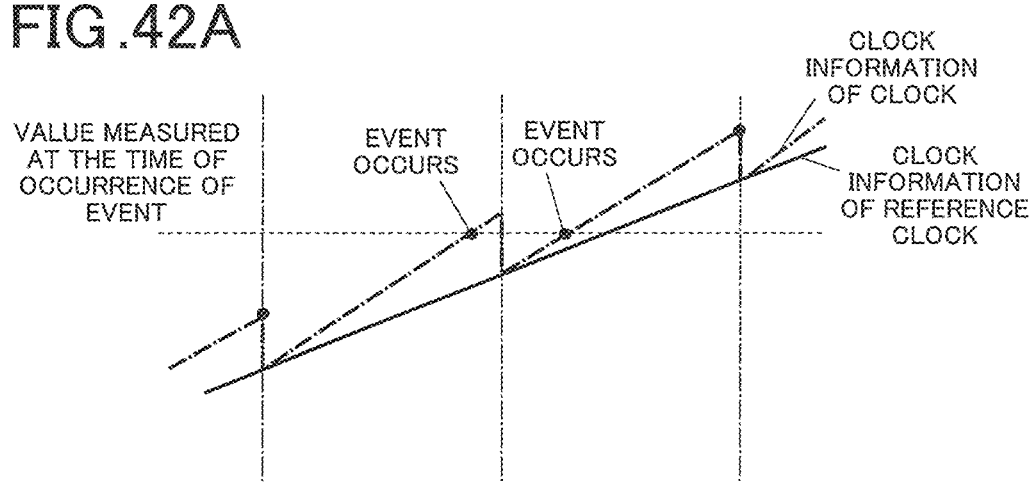
FIG. 42A is a graph illustrating an operation of the radiographic imaging system that does not have the configuration of Example 4-2.

For example, as illustrated in FIG. 42A, when the clock information is rewound across the time point of a certain event by the update after passing the time point of the event, the same event is erroneously performed twice. When the event is irradiation, the subject S is exposed to unnecessarily repeated radiation. Further, the frame that is taken when the irradiation is repeated is exposed to the radiation R twice and has a different image quality than the other frames.

To cope with the problem, in the above-described embodiments, when the occurrence of a time difference between the clock information of the clocks is detected, the clock rate of at least one of the clocks may be adjusted.

Figure 42B:
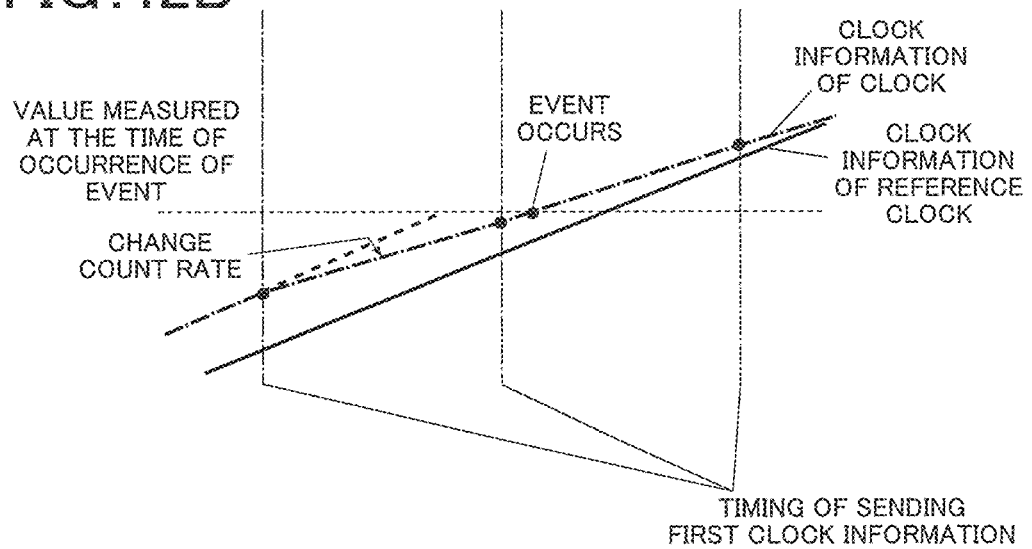
FIG. 42B is a graph illustrating an operation of the radiographic imaging system according to Example 4-2.

Specifically, when the first clock information is sent or received, the clock information is not updated. Instead, the clock rate of the earlier clock may be decreased or the clock rate of the later clock may be increased as illustrated in FIG. 42B so that the time difference is reduced to a level that does not require an update of the clock information by the time the next first clock information is sent or received.

This can prevent problems relating to rewind of the clock information.

Example 4-3

Figure 43:
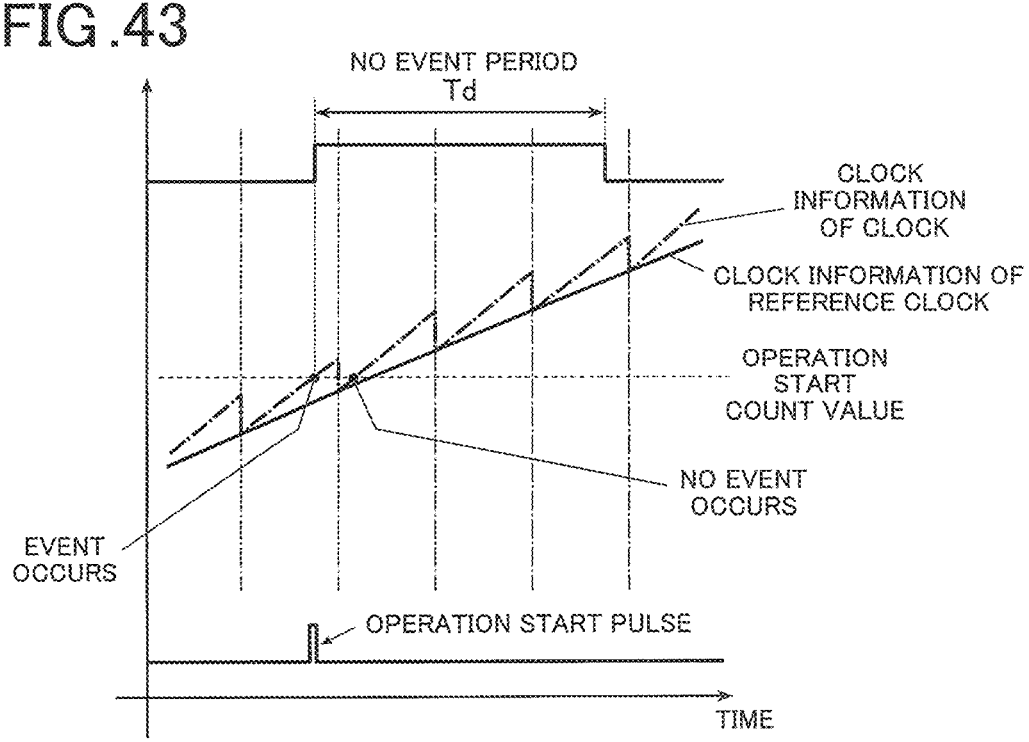
FIG. 43 is a flowchart illustrating an operation of the radiographic imaging system according to Example 4-3.

As described in Example 4-2, there is a problem that an update that rewinds the clock information may sometimes cause repetition of the same event. To cope with the problem, in Example 4-2, the clock rate of the clocks is changed. Instead, as illustrated in FIG. 43, a no event period Td in which execution of the same event is prohibited may be set immediately after an event is performed.

Without changing the clock rate of the clocks, this can prevent a trouble that the same event is repeated.

Example 5-1

In the above-described embodiments, when the communication between the clock information source apparatus 2, 4 (irradiating apparatus 1) and the imaging apparatus 3 is lost, an imaging process has to be canceled regardless of whether it is possible to further continue the imaging process. This is because it is uncertain how long the imaging process can be continued.

To cope with the problem, in the above-described embodiments, the number of images that can be further taken may be calculated from the clock rate and the accuracy of the clock information source apparatus 2, 4 and the imager clock 37, and the imaging process may be continued until the number of images taken reaches the calculated number.

Specifically, the relationship between factors that affect the accuracy of the oscillation cycle of the oscillators of the irradiating apparatus 1 and the imaging apparatus 3, and the oscillation cycle is stored in the storage 35 beforehand.

Figure 44:
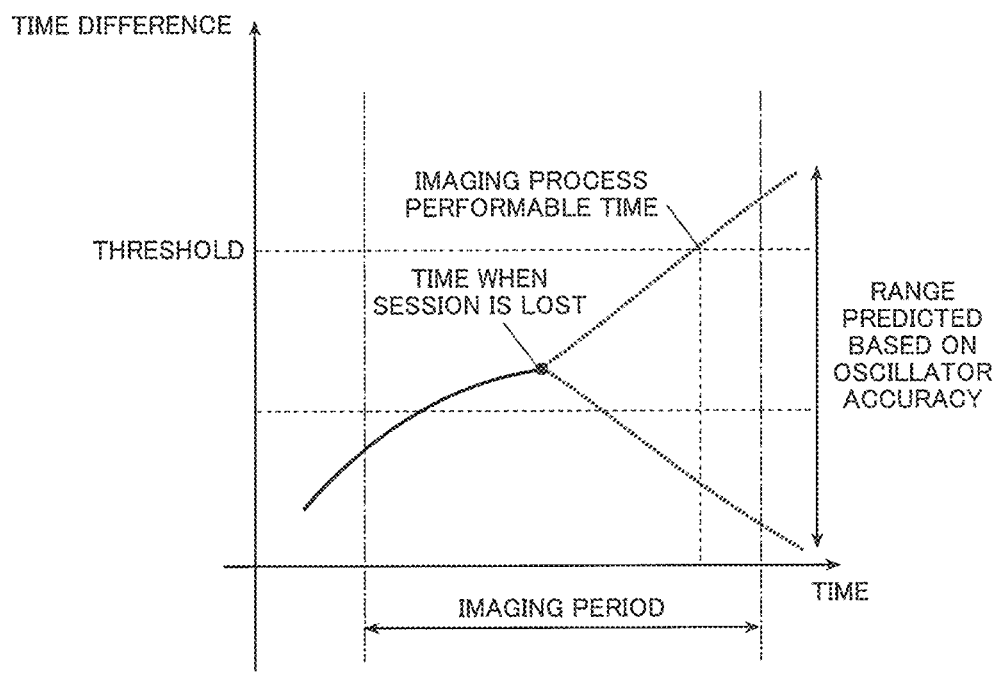
FIG. 44 is a graph illustrating an operation of the radiographic imaging system according to Example 5-1.

Further, the imaging controller 31 has a function of predicting the change of the time difference (time lag) between the first clock information of the clock information source apparatus 2, 4 and the second clock information of the imager clock 37 based on the time difference immediately after the loss of the connection, the clock rate of the clock information source apparatus 2, 4 and the imager clock 37 and the relationship between the factors and the accuracy stored in the storage 35. As illustrated in FIG. 44, the change of the time difference may have an increasing or decreasing trend depending on the accuracy.

Further, from the predicted change of the time difference, the imaging controller 31 has a function of calculating an imaging operable period until the time difference exceeds a predetermined threshold (an upper limit of the time difference for emitting the radiation in the accumulating period).

Further, the imaging controller 31 has a function of calculating the number of images that can be further taken from the calculated imaging operable period and the frame rate.

With this configuration, it is possible to continue the imaging process until the number of images taken reaches the calculated number even after the communication between the clock information source apparatus 2, 4 and the imaging apparatus 3 is lost.

Example 5-2

As described in Example 5-1, there is a problem that an imaging process has to be canceled when the communication is lost. To cope with the problem, in Example 5-1, the number of images that can be further taken is calculated, and the imaging process is continued until the number of images taken reaches the calculated number. Instead, a determination may be made as to whether to continue the imaging process based on the required number of images (the number of images that has not be taken yet) and the accuracy of the oscillators of the irradiating apparatus 1 and the imaging apparatus 3.

Specifically, the same parameter as in Example 5-1 is stored in the storage 35 beforehand.

The imaging controller 31 of Example 5-1 (which has the function of calculating the number of images that can be further taken) further has a function of comparing the calculated number of images that can be further taken with the number of images that have not been taken yet.

The imaging controller 31 further has the following function. When the number of images that can be further taken is equal to or greater than the number of images that have not been taken yet, the imaging controller 31 continues the imaging process. When the number of images that can be further taken is less than the number of images that have not been taken yet, the imaging controller 31 performs an output such as giving a notification that the imaging process cannot be continued to the last, giving a notification that imaging is disabled, or cancelling the imaging process.

In this configuration, the imaging process can be continued when the communication between the clock information source apparatus 2, 4 and the imaging apparatus 3 is lost but the imaging process can be continued until the preset number of images are taken.

When the imaging process is continued, a notification may be given to the user that the connection is lost but the imaging process can and will be continued to the last.

When the imaging process is continued after loss of the communication, the image data of images that are taken while the communication is lost may be associated with specific information (flag or the like).

Example 5-3

In Example 5-1, temperature may be further used to calculate the number of images that can be further taken. That is, temperature may be used as one of the factors that affect the accuracy of the oscillation cycle of the oscillators.

Figure 45A:
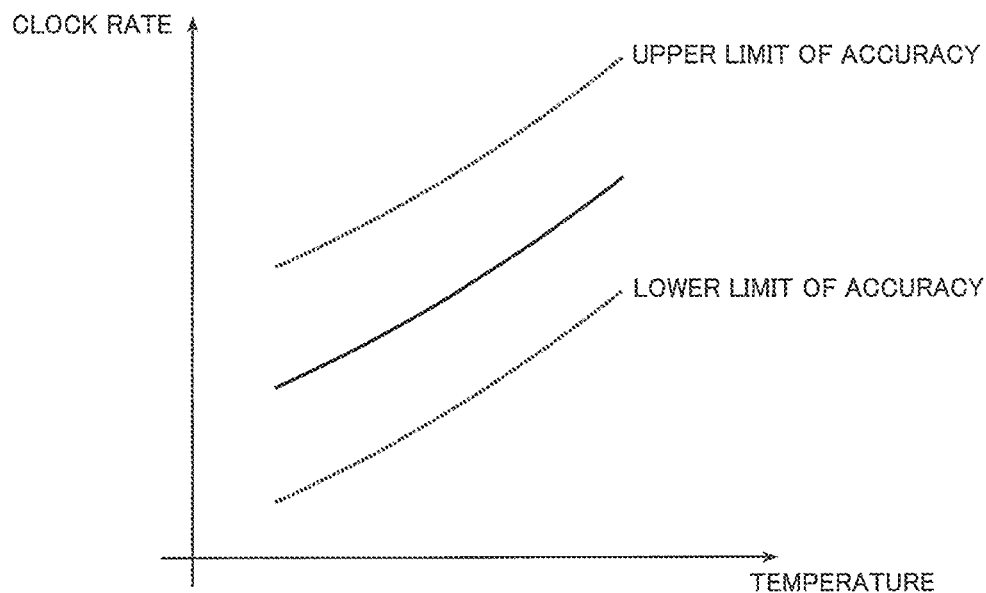
FIG. 45A is a graph illustrating the relationship between temperature and clock rate.

Specifically, the relationship between the temperature and the oscillation cycle of the oscillators of the irradiating apparatus 1 and the imaging apparatus 3 is stored in the storage 35 beforehand as illustrated in FIG. 45A. In the figure, the solid line represents a theoretical value, and the upper and lower dashed lines represent respectively the upper and lower limits based on the accuracy.

The imaging controller 31 has a function of predicting the change of the time difference (time lag) between the first clock information of the clock information source apparatus 2, 4 and the second clock information of the imager clock 37 from the time difference immediately after loss of the connection, the clock rate of the clock information source apparatus 2, 4 and the imager clock 37 and the relationship between the factors and the accuracy stored in the storage 35.

The imaging controller 31 also has the same functions as in Example 5-1.

Figure 45B:
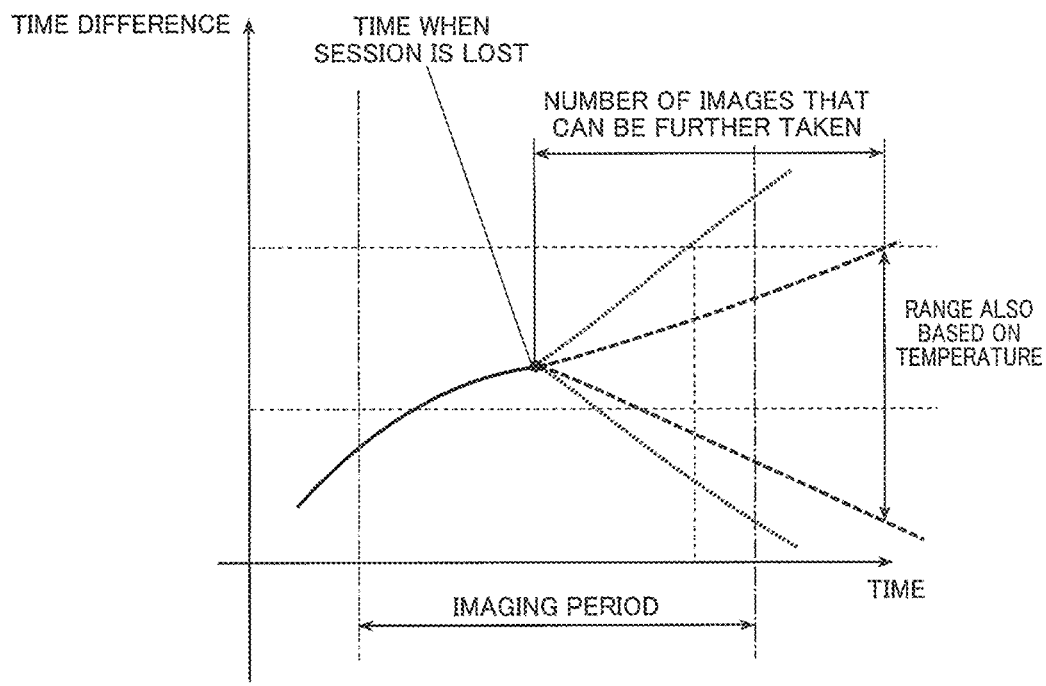
FIG. 45B is a graph illustrating an operation of the radiographic imaging system according to Example 5-3 of first and second inventions.

Since the temperature of the oscillators largely affects the accuracy of the oscillation cycle of the oscillators compared to the other factors, this configuration allows predicting the change of the time difference with higher accuracy as illustrated in FIG. 45B. As a result, the number of images that can be further taken can be calculated with higher accuracy.

As with Example 5-2, a determination as to whether the imaging process can be continued to the last may be made. If so, the imaging process may be continued. If not, the imaging process may be cancelled.

Example 6-1

In the above-described embodiments, once the synchronization is performed, further synchronization may not be performed any more.

Specifically, the imaging controller 31 has a function of performing the time synchronization when the first clock information is sent for the first time after the user presses down the exposure switch.

Further, the imaging controller 31 has a function of not updating the clock information of the imager clock 37 while the exposure switch is pressed down after the synchronization is checked.

This prevents the operation timing of the imaging apparatus 3 from being changed during the imaging period. Therefore, the imaging process can be stably performed.

The imaging controller 31 may measure the difference between the first clock information and the second clock information when the first clock information is sent for the first time after the time synchronization, so as to check whether the time synchronization has been successfully performed or whether the time difference after the time synchronization is equal to or less than a predetermined value.

This can prevent an image from being taken when the apparatuses are actually not synchronized with each other. The subject S can thus be prevented from being exposed to unnecessary radiation.

Example 6-2

Another problem in the above-described embodiments is that when the synchronization is performed irregularly, the change of the operation timing of the irradiating apparatus 1 or the imaging apparatus 3 affects the output images, which may lead to a misdiagnosis.

Figure 46:
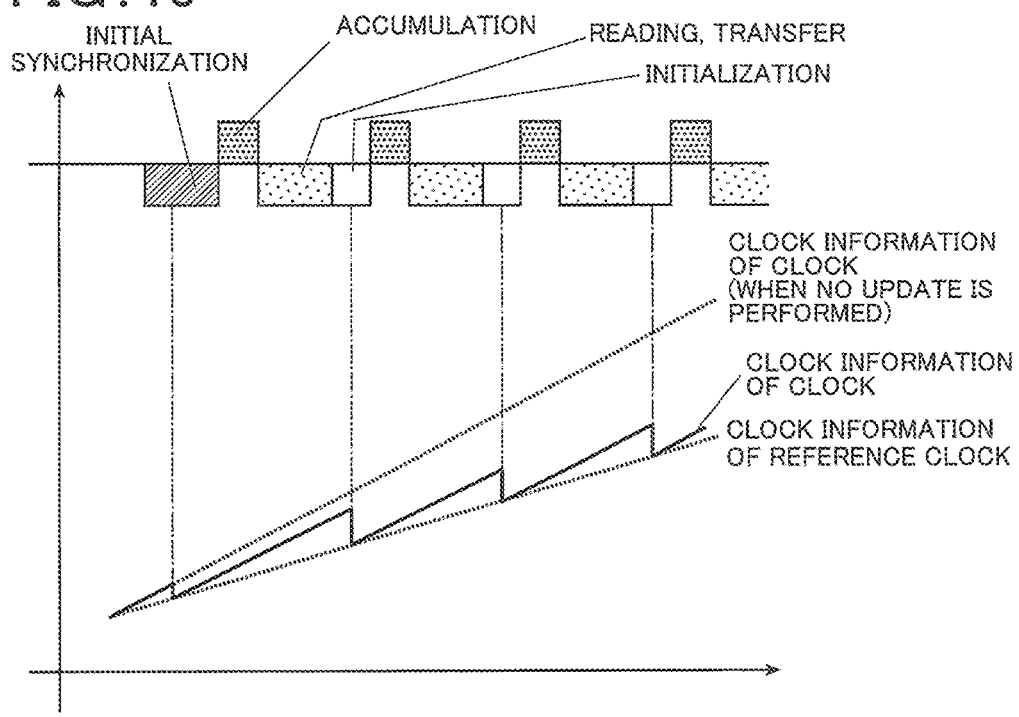
FIG. 46 is a flowchart of an operation of the radiographic imaging system according to Example 6-2.

To cope with the problem, in the above-described embodiments, the synchronization may be performed at the timing of the imaging cycle (i.e. every time a frame is taken) during the imaging period as illustrated in FIG. 46.

In this configuration, the synchronization is performed at the timing of taking each frame image. This can prevent only a certain frame image from being affected by the synchronization of the operation timing.

This influence of the change of the operation timing on the image tends to become noticeable when the difference of a feature value between adjacent frame images is used for an analysis. However, the above-described configuration can also eliminate such influence on an analysis that uses the difference of a feature value.

The cycle of sending the first clock information from the clock information source apparatus 2, 4 may be equal to the imaging cycle or a value obtained by dividing the imaging cycle by an integer.

In this case, the timing of the synchronization may be shifted by a predetermined phase with respect to the timing of sending the first clock information.

Example 6-3

Figure 47:
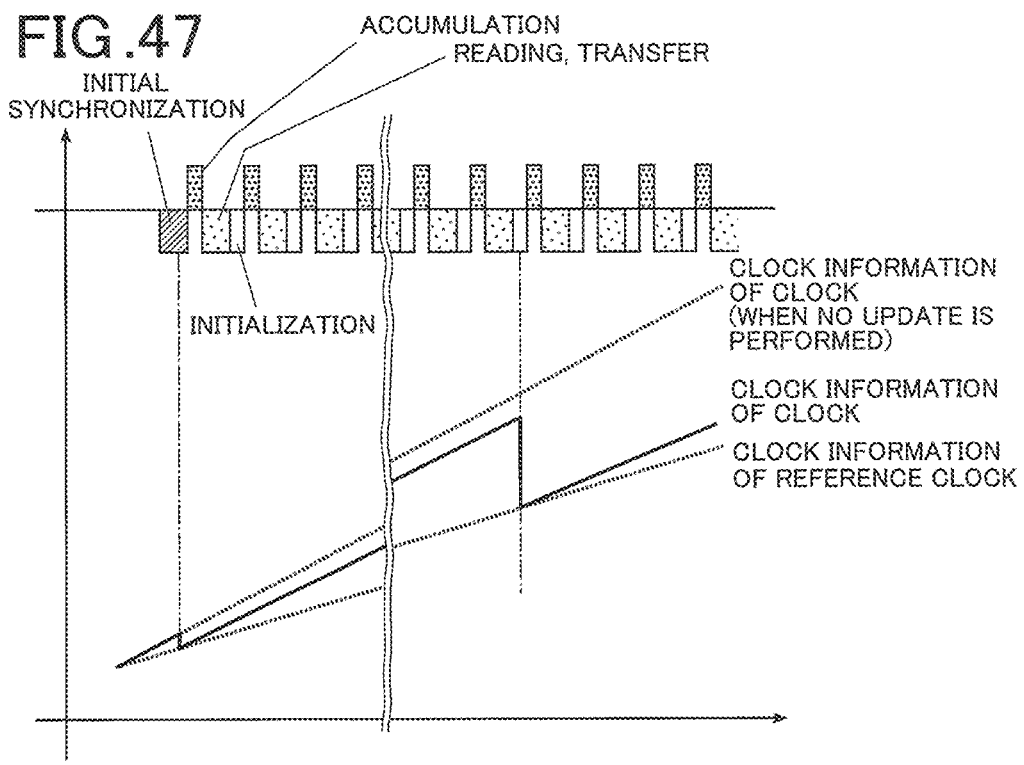
FIG. 47 is a flowchart of an operation of the radiographic imaging system according to Example 6-3.

As described in Example 5-1, there is a problem that irregular synchronization may affects output images. To cope with the problem, in Example 5-1, the synchronization is performed every time a frame image is taken. Instead, the synchronization may be performed every time tens of frame images are taken, for example, as illustrated in FIG. 47.

This can reduce the influence on frame images even in a lengthy serial imaging process.

In this configuration, it is preferred that the synchronization is performed at a time point in the imaging period at which the synchronization is less likely to affect the images.

For example, when serial images of a lung field are taken, the synchronization is performed not in the course of taking a breath in or out (when the movement of the lung is significant), which is important for making a diagnosis, but at the completion of taking a breath in or out (when the movement of the lung is small) or the like.

This can prevent an image taken at the timing important for a diagnosis from being affected by the change of the operation timing.

Example 6-4

Figure 48:
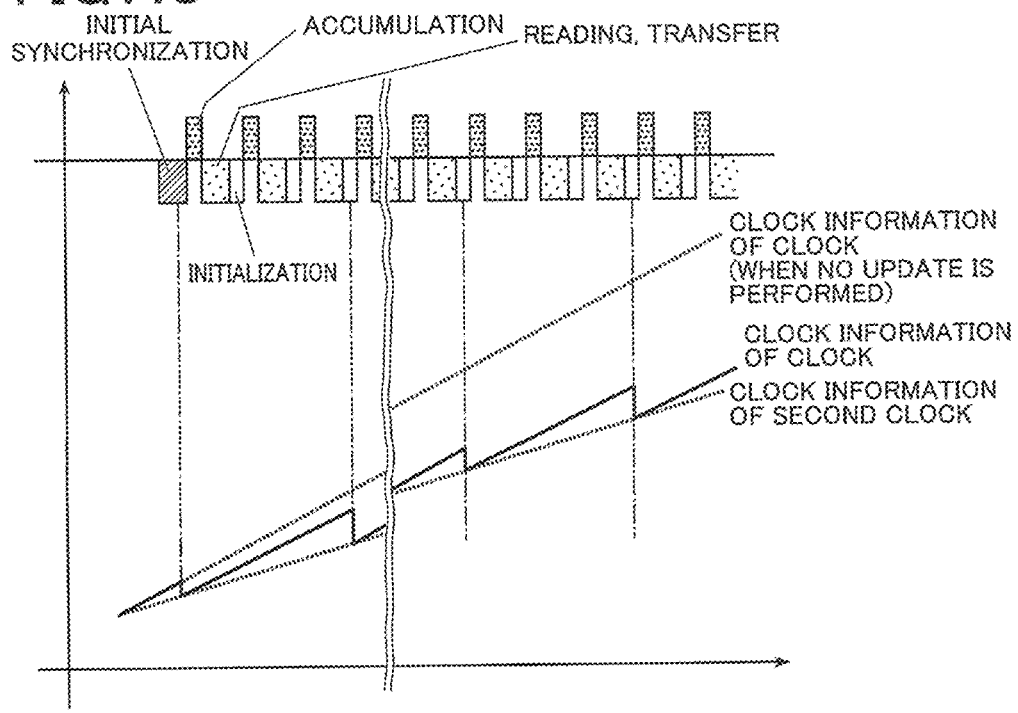
FIG. 48 is a flowchart of an operation of the radiographic imaging system according to Example 6-4.

As described in Example 5-1, there is a problem that irregular synchronization may affect output images. To cope with the problem, in Example 5-1, the synchronization is performed every time a frame image is taken. Instead, the synchronization may be performed every time several frame images are taken, for example, as illustrated in FIG. 48.

When the synchronization is performed in every frame as described in Example 6-1, the lengthy processing of the synchronization cannot sometimes be completed within the time of taking a frame image. This may affect the next frame image. On the other hand, when the synchronization is performed in every tens of frames as described in Example 6-2, the time lag of the operation timing may sometimes become too large. In contrast, in this configuration, the synchronization is performed at suitable intervals. This can eliminate the influence of the synchronization processing on the next frame as well as reduce the amount of change of the operation timing by the synchronization. Therefore, the influence of the synchronization on output images can be reduced.

After the clock information of the clocks is changed in a certain frame, relevant processing may be performed in the next or later frame.

This can spread the update of the clock information and the other processing to two or more frames. Even when the other processing is a considerable burden, the clock information can be certainly updated at predetermined timing.

Example 6-5

Figure 49:
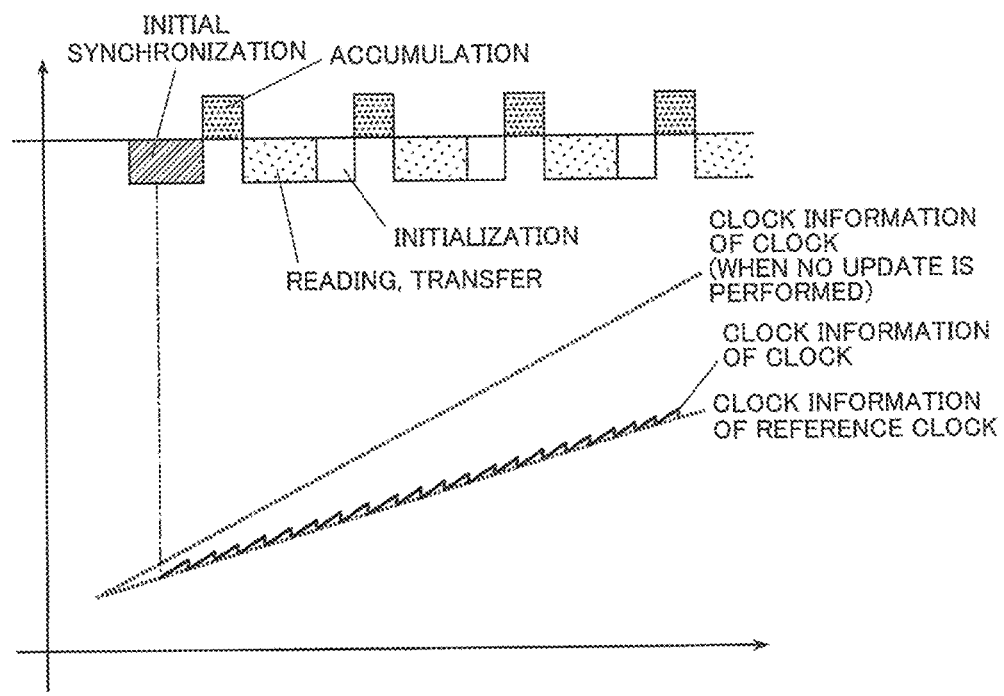
FIG. 49 is a flowchart of an operation of the radiographic imaging system according to Example 6-5.

As described in Example 5-1, there is a problem that irregular synchronization may affects output images. To cope with the problem, in Example 5-1, the synchronization is performed every time a frame image is taken. Instead, the synchronization may be performed at intervals that are shorter than the imaging cycle (i.e. the synchronization may be performed twice or more while one frame image is taken) as illustrated in FIG. 49.

This can reduce the amount of change of the operation timing by the synchronization and thus reduce the influence on output images.

Although not shown in the figure, the synchronization may be suspended during a specific step in the process of taking each frame image.

For example, the specific step may be accumulation of charges, reading and transfer of image data, initialization or the like that is performed by the imaging apparatus 3.

Since the synchronization during such specific steps is more likely to affect output images, this configuration can reduce the influence on output images. Specifically, suspension of the synchronization during accumulation can reduce the influence on the image contrast of each frame image. Further, suspension of the synchronization during reading and transfer can reduce the influence of the noise.

Example 6-6

In the above-described embodiments, the synchronization may affect output images. To avoid this, it is sometimes desired not to perform the synchronization depending on an imaging technique or an analyzing method used as long as the time lag of the operation is within a predetermined range.

Figure 50:
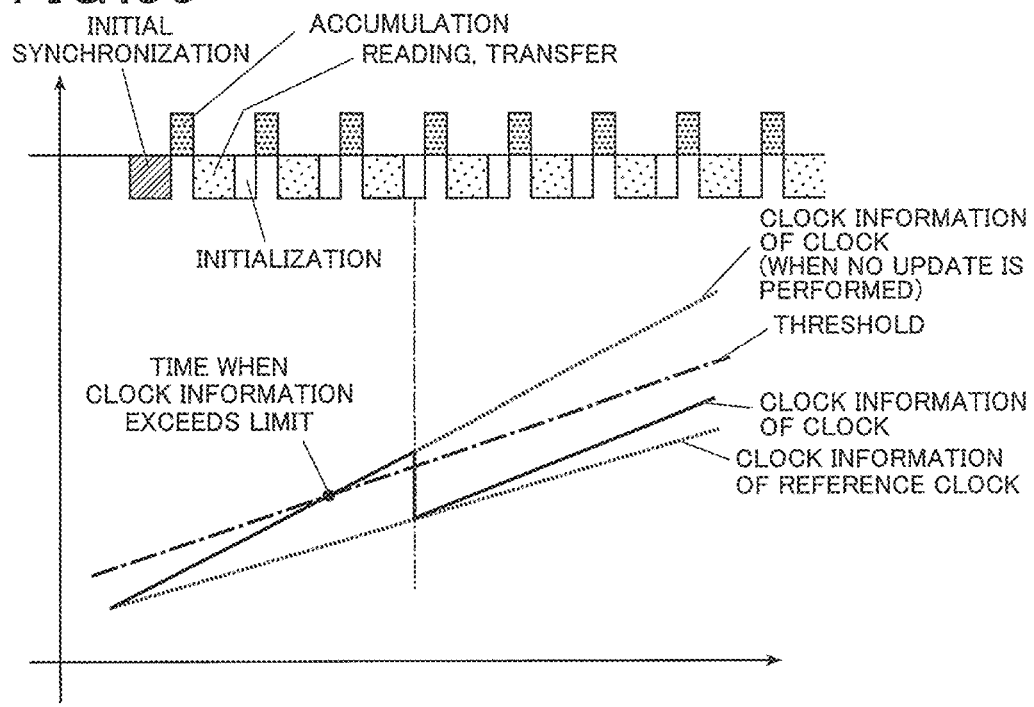
FIG. 50 is a flowchart of an operation of the radiographic imaging system according to Example 6-6.

To address the need, in the above-described embodiments, the time difference (time lag) between the first clock information of the clock information source apparatus 2, 4 and the second clock information of the imager clock 37 may be periodically measured, and the synchronization may be performed only when the time difference exceeds a threshold as illustrated in FIG. 50.

This can reduce the synchronization processing as few as possible and thereby reduce the risk of the influences on output images.

The synchronization may be suspended during a specific step even when the time difference exceeds the threshold. In this case, the synchronization may be performed after the specific step is completed.

For example, the specific step may be accumulation of charges, reading and transfer of image data, initialization or the like that is performed by the imaging apparatus 3.

Since the synchronization during such specific steps may affect images, this can reduce the influence on output images as little as possible.

When frame images are stored, a frame image that is taken at the timing of the synchronization may be associated with information indicating the synchronization is performed.

This allows later specifying the frame image that was taken when the synchronization was performed. When the images are affected by the synchronization, specifying the frame image enables making a determination as to whether the influence shown in the images is due to the synchronization or the subject to be diagnosed.

Example 7-1

Another problem in the above-described embodiments is that when a time lag occurs between the operation of the irradiating apparatus 1 and the operation of the imaging apparatus 3, whether the image quality is affected depends on which apparatus is selected as the base of the synchronization.

To cope with the problem, in the above-described embodiments, the operation of the irradiating apparatus 1 may be aligned with the operation of the imaging apparatus 3 when a time lag of the operation is detected.

Figure 51:
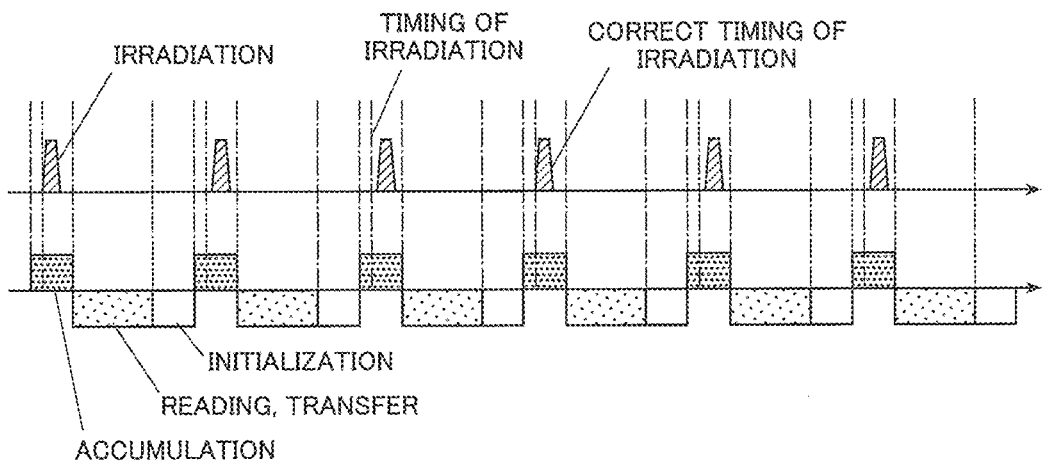
FIG. 51 is a flowchart of an operation of the radiographic imaging system according to Example 7-1.

Specifically, as illustrated in FIG. 51, the timing of irradiation is delayed when it is too early, or the timing of irradiation is put ahead when it is too late.

While correction of the operation of the imaging apparatus 3 is likely to cause variation of contrast between frame images, this configuration can prevent such variation of contrast.

As in Example 6-6, when frame images are stored, a frame image that is taken at the timing of the synchronization may be associated with information indicating the synchronization is performed.

This allows later specifying the frame image that was taken when the synchronization was performed. When the images are affected by the synchronization, specifying the frame image enables making a determination as to whether the influence shown in the images is due to the synchronization or the subject to be diagnosed.

Example 7-2

As described in Example 7-1, there is a problem that whether the image quality is affected depends on which apparatus is selected as the reference of the synchronization. To cope with the problem, in Example 7-1, the operation of the irradiating apparatus 1 is corrected based on the operation of the imaging apparatus 3. Instead, the operation of the imaging apparatus 3 may be aligned with the operation of the irradiating apparatus 1 when a time lag of the operation is detected.

Figure 52:
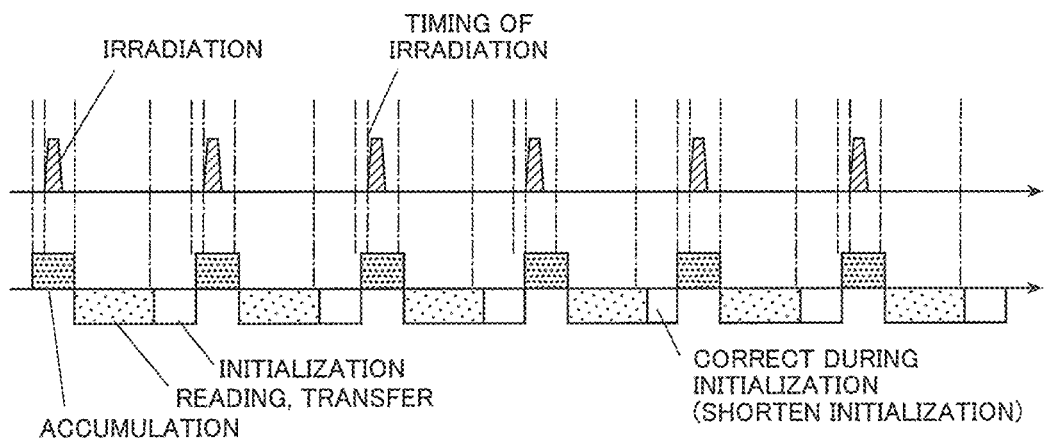
FIG. 52 is a flowchart of an operation of the radiographic imaging system according to Example 7-2.

Specifically, as illustrated in FIG. 52, initialization is shortened to put ahead the timing of accumulation when it is too late, or initialization is extended to delay the timing of accumulation when it is too early.

The synchronization may be suspended during a specific step even when it becomes necessary to perform the synchronization. In this case, the synchronization may be performed after the specific step is completed.

For example, the specific step may be accumulation of charges, reading and transfer of image data, initialization or the like that is performed by the imaging apparatus 3.

Since the synchronization during such specific steps may affect images, this can reduce the influence on output images as little as possible.

As in Example 7-1, when frame images are stored, a frame image that is taken at the timing of the synchronization may be associated with information indicating the synchronization is performed.

This allows later specifying the frame image that was taken when the synchronization was performed. When the images are affected by the synchronization, specifying the frame image enables making a determination as to whether the influence shown in the images is due to the synchronization or the subject to be diagnosed.

Example 7-3

Figure 53:
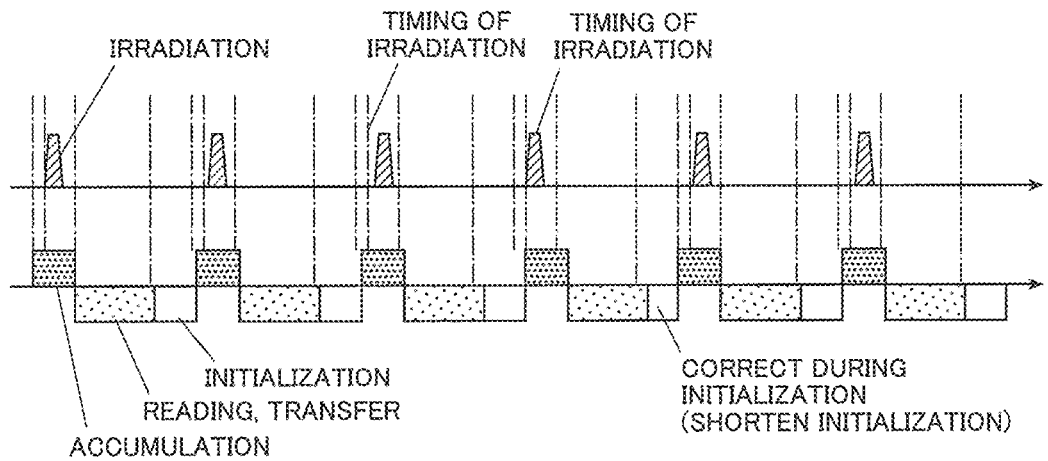
FIG. 53 is a flowchart of an operation of the radiographic imaging system according to Example 7-3.

As described in Example 7-1, there is a problem that whether the image quality is affected depends on which apparatus is selected as the reference of the synchronization. To cope with the problem, in Example 7-1, the operation of the irradiating apparatus 1 is corrected based on the operation of the imaging apparatus 3. Instead, the operation of both the irradiating apparatus 1 and the imaging apparatus 3 may be corrected as illustrated in FIG. 53.

Correction of the operation of the irradiating apparatus 1 and correction of the operation of the imaging apparatus 3 may have respectively different influences on images. In such cases, it is difficult to eliminate the influences when only one of them is corrected. However, in this configuration, the operation of the irradiating apparatus and the operation of the imaging apparatus are both slightly corrected. This can reduce the influences on images.

The first clock information of the clock information source apparatus 2, 4 may be used as a reference to correct the operation of both the irradiating apparatus 1 and the radiation detector.

Since both the irradiating apparatus 1 and the imaging apparatus 3 are connected to the clock information source apparatus 2, 4 as the reference, the synchronization can be performed stably.

The clock information source apparatus 2, 4 can communicate with an external network according to a communication standard such as IEEE 1588 to perform the time synchronization in cooperation with another external clock. Therefore, more accurate clock information can be used as the reference.

The irradiating apparatus 1 and the imaging apparatus 3 generate heat during operation, which may sometimes affect the reference oscillators of the internal clocks. However, the clock information source apparatus 2, 4 can be disposed away from the irradiating apparatus 1 and the imaging apparatus 3 and is less likely to be affected by the heat. Therefore, the clock information source apparatus 2, 4 can output the clock information more stably.

The system may be configured to be able to select an apparatus to be corrected from among the irradiating apparatus 1, the imaging apparatus 3 and both of them according to the contents of an image to be taken and the imaging technique used. Since the synchronization method is selected according to the imaging method and the imaging technique, the influences on images can be kept within the allowable range that varies depending on the imaging method and the imaging technique.

When the operation of both apparatuses is corrected, the proportion of the correction may be changeable. For example, in an analysis of bloodstream, it is important to reduce the variation of contrast between adjacent frame images. In order to reduce the contrast variation, for example, the proportion of the correction may be selected so that the amount of correction of the irradiating apparatus 1 is greater than the amount of correction of the imaging apparatus 3.

Example 7-4

As described in Example 7-1, there is a problem that whether the image quality is affected depends on which apparatus is selected as the reference of the synchronization. To cope with the problem, in Example 7-1 to Example 7-3, the operation of at least one of the irradiating apparatus 1 and the imaging apparatus 3 is corrected. However, even in these configurations, images may sometimes be still affected when the synchronization is performed during a specific step.

To cope with the problem, in the above-described embodiments, the synchronization may be suspended during a specific step in the process of taking each frame image.

For example, the specific step may be accumulation of charges, reading and transfer of image data, initialization or the like that is performed by the imaging apparatus 3.

Since the synchronization during such specific steps is more likely to affect images, this can reduce the influence on output images.

Example 8-1

In the above-described embodiments, the imaging apparatus 3C may generate the reading start times from the imaging sequence start time and the frame rate by itself while the controlling apparatus 12 similarly generate the exposure start times by itself. In this case, when the frame rate is changed at different timing between the imaging apparatus 3C and the controlling apparatus 12, the imaging fails. For example, when frame rate information is sent from the controlling apparatus 12 to the imaging apparatus 3C, the timing of changing the frame rate at the imaging apparatus 3C may sometimes be delayed due to communication delay such as packet loss.

To cope with the problem, in the above-described embodiments, the controlling apparatus 12 and the imaging apparatus 3C may count common frame numbers. When the controlling apparatus 12 (or the imaging apparatus 3C) receives an instruction to change the frame rate, it may send a rate-changing frame number and the frame rate to the imaging apparatus 3C.

To avoid the influence of communication delay, the rate-changing frame number may be calculated as the sum of the current frame number and a certain number that is greater than "expected communication delay/frame cycle+1".

When the number of counts reaches the rate-changing frame number, the controlling apparatus 12A and the imaging apparatus 3C changes the frame rate.

In this configuration, the timing of changing the frame rate is less likely to be delayed.

Instead of the rate-changing frame number, a rate-changing time may be notified. When the rate-changing time is close to a frame transition time, the timing of changing the frame rate may not be synchronized depending on the synchronization accuracy of the clocks. To avoid this, the rate-changing time is selected so that it is not within the ranges of frame transition times±α. The value α is greater than the expected synchronization accuracy in an imaging process.

Example 8-2

As described in Example 8-1, there is a problem that when the imaging apparatus 3C generates the reading start times by itself while the controlling apparatus 12 generates the exposure start times, the timing of changing the frame rate at the imaging apparatus 3C is sometimes delayed due to communication delay. To cope with the problem, Example 8-1 has the following configuration. That is, the controlling apparatus 12 and the imaging apparatus 3C count the common frame numbers. When the controlling apparatus 12 receives an instruction to change the frame rate, it sends the rate-changing frame number and the frame rate to the imaging apparatus 3C. Instead, the imaging apparatus 3C may read an image at the maximum frame rate while the controlling apparatus 12 performs an exposure once every predetermined reading operations of the imaging apparatus 3C so that images are taken at a desired frame rate.

For example, assuming that images are taken at 7.5 fps with the system having the maximum frame rate of 15 fps. In this case, the imaging apparatus 3C reads an image at 15 fps while the controlling apparatus 12 performs a single exposure every time the imaging apparatus 3C reads two frames.

In this configuration, the imaging apparatus can generate the reading start times by itself while the radiation controlling apparatus can generate the exposure start times by itself. Accordingly, the imaging sequence start time and the frame rate are the only information that has to be shared between the imaging apparatus 3C and the controlling apparatus 12A. This can reduce the risk of an imaging failure caused by communication delay or packet loss between the imaging apparatus 3C and the controlling apparatus 12C or the like. Such an imaging failure occurs when a reading start time is received after the time point specified by the reading start time, or when an exposure start time is received after the time point specified by the exposure start time.

In this configuration, unlike Example 8-1, it is not essential to exchange frame rate changing information between the controlling apparatus 12A and the imaging apparatus 3C when the frame rate is changed. Accordingly, the frame rate can be changed in a moment. This allows the user to select a desired frame rate at desired timing. Therefore, the usability of the system is improved.

Example 8-3

In Example 8-2, the imaging apparatus 3C reads several frames at the maximum frame rate while an exposure is performed. Therefore, some of the frame images generated by the imaging apparatus 3C are unexposed images (hereinafter referred to as white images). A problem with this is that such white images degrade the visibility of a dynamic image.

To cope with the problem, white images may be removed in Example 8-2.

Specifically, the average or maximum value of the signal values of the pixels in a predetermined area (including the whole area) is compared with a predetermined threshold with respect to each frame. When the average or maximum value is equal to or less than the threshold, the image is determined as a white image. Images determined as white images may be deleted or associated with white image attribute information so that the frame images associated with the attribute information are not displayed.

The above-described processing may be performed by either the imaging apparatus 3C or the console 14. When the above-described processing is performed by the imaging apparatus 3C, it is possible to reduce the amount of data sent from the imaging apparatus 3C to the console 14. This can reduce the occurrence of delay between taking frame images and displaying them on the console 14.

Example 8-4

As described in Example 8-3, there is a problem in Example 8-2 that some of frame images to be generated are white images. To cope with the problem, in Example 8-3, a frame image is removed when it is determined as a white image based on the signal values of pixels of the frame image. Instead, the determination may be made based on the frame number of each frame image, and a frame image that is determined as a white image is removed.

Specifically, according to a rule that is common between the controlling apparatus 12 and the imaging apparatus 3C, unique frame numbers (e.g. sequential numbers) are given to all frames that are taken in a serial imaging process.

Further, the controlling apparatus 12 has a function of associating information representing whether the image is exposed with each frame number, storing it as exposed frame information and sending the exposed frame information to the imaging apparatus 3C or the console 14.

The imaging apparatus 3C or the console 14 has a function of storing a clock time (e.g. the exposure start time, the exposure end time, a certain time in a frame, or the like) of each frame and referencing the received exposure frame numbers to delete unexposed frame images or to prohibit unexposed frame images from being displayed.

Alternatively, the controlling apparatus 12 may have a function of storing clock times of exposed frames and unexposed frames as information indicating whether each frame image is exposed and sending the information to the imaging apparatus 3 or the console 14. The imaging apparatus 3C or the console 14 has a function of storing the clock times of the frames and comparing them with the received information so as to delete the unexposed frame images or prohibit the unexposed frame images from being displayed.

This configuration eliminates the necessity of making a determination as to whether each image is a white image. This can reduce the load on the imaging apparatus or the console and thereby reduce the delay between taking frame images and displaying them on the console.

Example 8-5

Regarding the above-described embodiments, there is a need for a system that can perform an exposure and the subsequent reading step at suitable timing after the user presses down the exposure switch to start an imaging process.

For example, when the tube 13 is rotated during an imaging period, the suitable timing may be the timing when the tube 12 at a predetermined position (or any one of predetermined positions). When the subject S is asked to breath according to an announcement, the suitable timing may be the timing(s) when a predetermined message is announced. When images are taken while the subject S is changing his/her position, the suitable timing may be the timing when the subject S is in a predetermined position.

To address the need, in the above-described embodiments, the controlling apparatus 12 may determine an exposure start time and a reading start time when it reaches the suitable timing, and the reading start time is sent from the radiation controlling apparatus 12A to the imaging apparatus 3C. Then, the controlling apparatus 12 starts an exposure when the clock information of its own clock reaches the exposure start time while the imaging apparatus starts a reading operation when the clock information of its own clock reaches the reading start time.

The exposure start time and the reading start time are determined based on the expected latency of the wireless communication.

The reading start time is calculated as the sum of the synchronized clock information at the suitable timing and the longer period of time between "the period of time from the current time until the imaging apparatus receives the reading start time and gets ready for the reading operation (which is determined also based on the expected latency of the wireless communication)" and "a period of time required for the controlling apparatus 12 to get ready for exposure+ an exposure time of a single frame".

Further, the exposure start time is at least "the exposure time of a single frame" earlier than the reading start time.

This can prevent an imaging failure that occurs when the imaging apparatus 3C receives a reading start time after the time point specified by the reading start time.

Instead of the controlling apparatus 12A, the imaging apparatus 3C may determine the exposure start time and the reading start time.

Example 8-6

As described in Example 8-5, there is a need for a system that can perform an exposure and the subsequent reading step at suitable timing after the user presses down the exposure switch to start an imaging process. To address the need, in Example 8-5, the controlling apparatus 12 determines an exposure start time and a reading start time when it reaches the suitable timing. Instead, the imaging apparatus 3C may generate a reading start time from the imaging sequence start time and the frame rate by itself while the controlling apparatus 12 generates the exposure start times by itself, so that the imaging apparatus 3C and the controlling apparatus 12 can always take images at the maximum frame rate. The imaging apparatus constantly performs the reading operations at the maximum frame rate while the controlling apparatus 12 controls the tube 13 to start exposure at the first exposure timing after the suitable timing.

In example 1-5, when the expected latency of the wireless communication is large, it takes a long time from the desired timing to the start of exposure. As a result, the exposure cannot sometimes be performed at the specified timing, which results in an imaging failure. However, in this configuration, the maximum delay of the start of exposure from the desired timing can be reduced to one cycle at the maximum frame rate (e.g. approximately 66.6 ms when the frame rate is 15 fps). Therefore, an imaging failure due to the delay can be prevented.

In this configuration, white images are generated. However, problems with white images can be solved by applying the configuration of Example 8-3 or the like.

Example 9-1

In the above-described embodiments, the clock information of the synchronized clocks is used to control exposure and reading. When the synchronization accuracy of the clocks is decreased during a series of exposures for taking two or more serial frame images, the synchronization between exposure and reading may sometimes be lost.

To cope with the problem, in the above-described embodiments, the clock information may be used to perform the synchronization only at the start of an imaging sequence.

Specifically, the radiation controller 121 has a function of starting the operation to emit radiation at predetermined timing when the clock information of the second irradiator clock 126 reaches an imaging start trigger time.

Further, the imaging controller 31 has a function of starting the operation to read charges at predetermined timing when the clock information of the second imager clock 39C reaches an imaging start time.

The timing of the reading sequence performed by the imaging apparatus 3C is preset so as to be later than the timing of the reading sequence performed by the controlling apparatus 12A.

Figure 54:
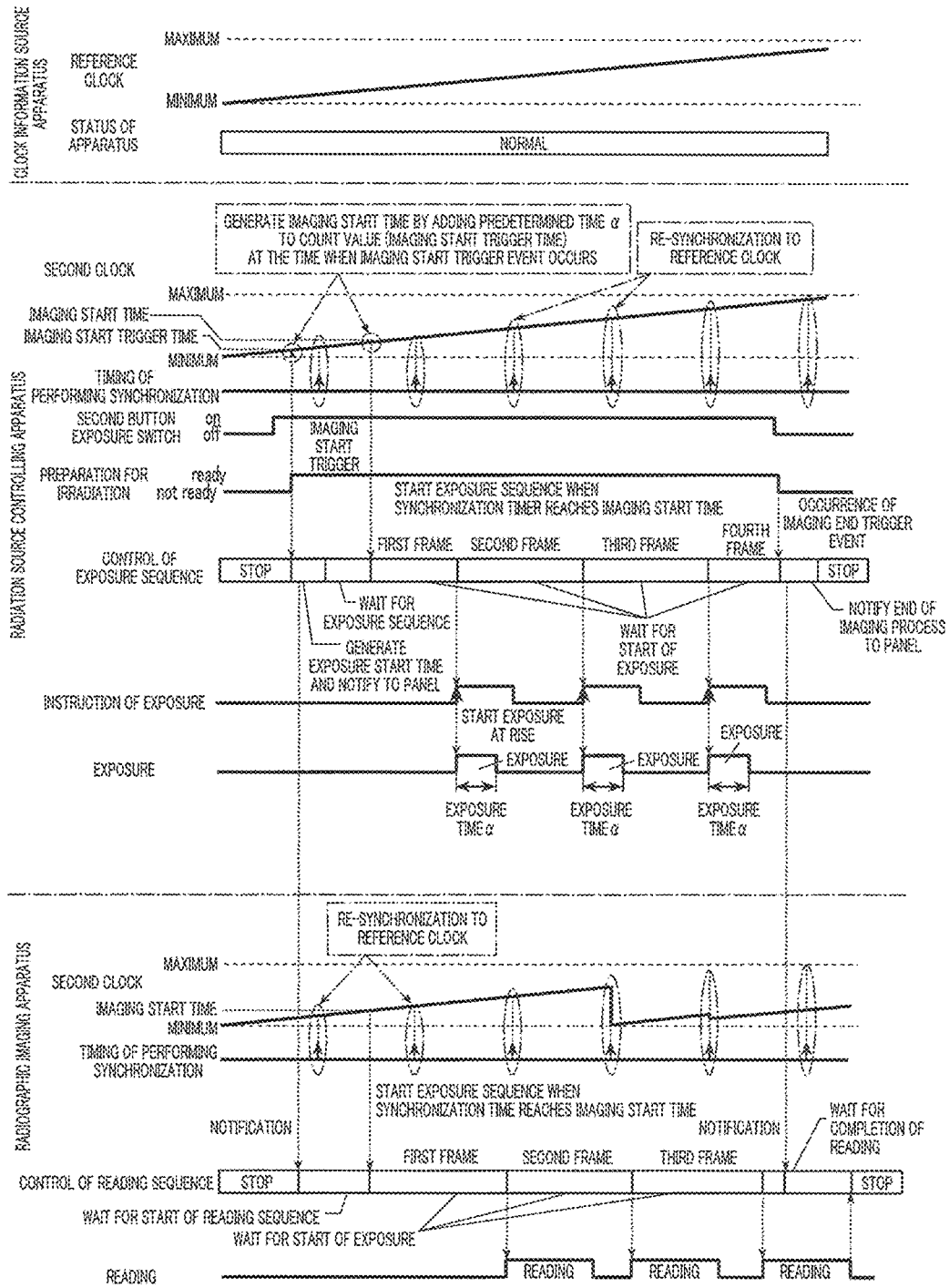
FIG. 54 is a flowchart of an operation of the radiographic imaging system according to Example 9-1.
Figure 55:
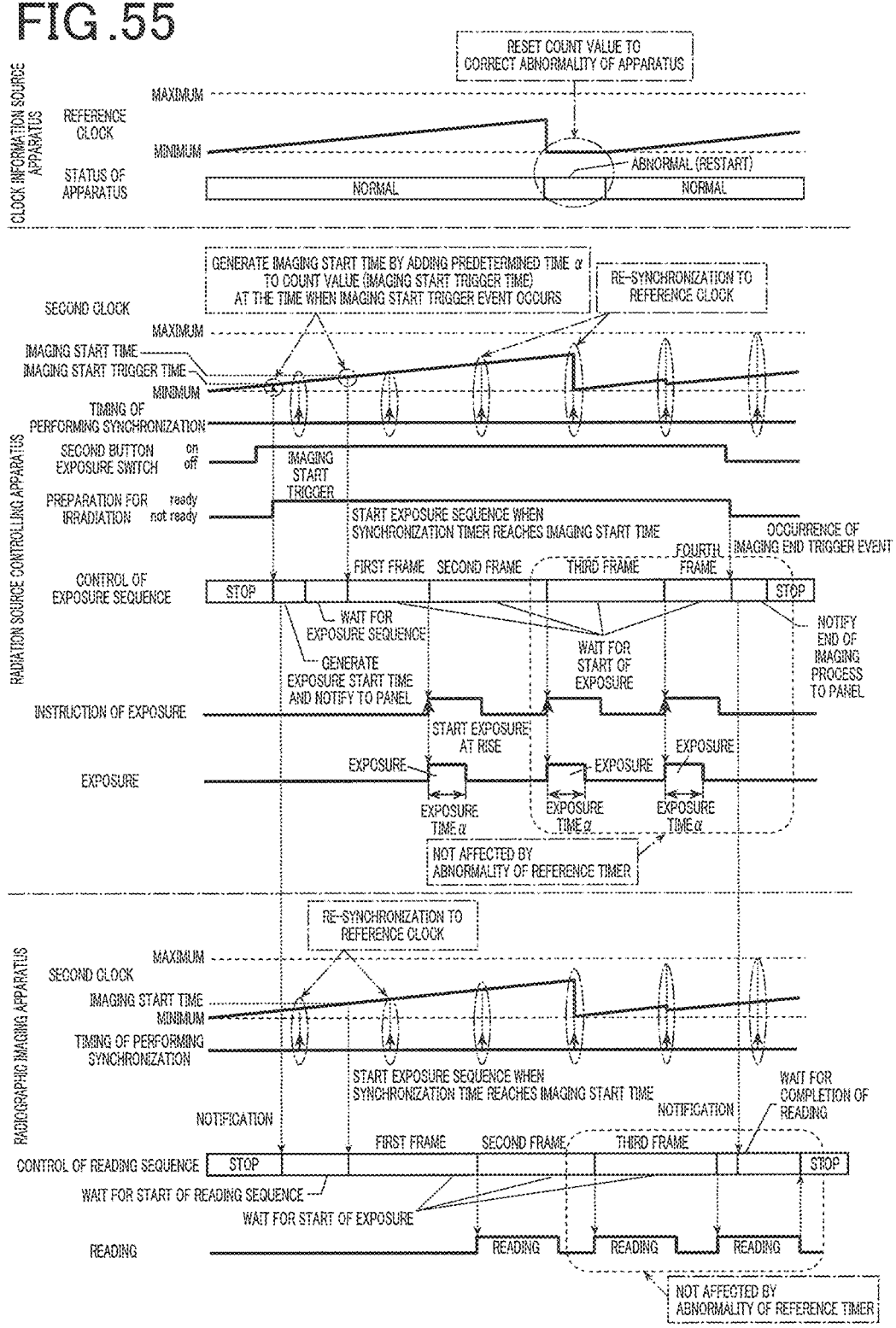
FIG. 55 is a flowchart of an operation of the radiographic imaging system according to Example 9-2.

In this configuration, once the imaging apparatus 3C starts controlling the reading sequence based on the clock information and the controlling apparatus 12A starts controlling the exposure sequence based on the clock information, the clock information is not used for performing the exposure and the reading as illustrated in FIG. 54. As illustrated in FIG. 55, even when an abnormality occurs in the clock information source apparatus 2, 4 during an imaging period so that the clock information of the second clocks 39C, 126 are changed, the controlling apparatus 12A and the imaging apparatus 3C can continue their operations without being affected by the abnormality.

Example 9-2

In the above-described embodiments, the imaging apparatus 3C includes the imager clock 37 and the second imager clock 39, and the imager clock 37 is synchronized with the clock information source apparatus 2, 4 regardless of the operation mode of the second imager clock 39. This configuration is designed to use a typical WLAN module.

Instead, a customized WLAN module may be used to omit the imager clock 37. When the second imager clock 39 is in the synchronization mode, the second imager clock 39C is synchronized with the clock information source apparatus 2, 4.

The omission of the imager clock 37 reduces the number of clocks used in the system. This can reduce the size of the circuit and software or simplify them.

In this example, the imager clock 37 of the imaging apparatus 3C is omitted. Instead, the irradiator clock 125 of the controlling apparatus 12 may be omitted, and the second irradiator clock 126 may be synchronized with the clock information source apparatus 2, 4.

Example 9-3

In the above-described embodiments, the imaging sequence start time is determined when the irradiation-ready signal is received from the high voltage generator 122. However, the wiring and the apparatuses have to be often modified to send the irradiation-ready signal depending on the characteristics and the system configuration of the high voltage generator 122, which results in the higher development cost.

To cope with the problem, in the above described embodiments, an alternative trigger that is different from the irradiation-ready signal may be used to determine the imaging sequence start time.

Examples of alternative triggers includes the following (1) to (3).

(1) The first button of the exposure switch is pressed down.

(2) The second button of the exposure switch is pressed down.

(3) A user instruction is received on a UI such as the console 14, the imaging apparatus 3, the controlling apparatus 12 or the exposure switch 15a.

The period of time after the first button of the exposure switch is pressed down until the second button is pressed down varies depending on the user operation. Further, after the first button of the exposure switch is pressed down, the high voltage generator 122 has to finish a rotor-up operation of the rotating anode of the tube 13 to get ready for irradiation. However, the rotor-up time also varies depending on the conditions. When the above-described trigger (1) is used as the alternative trigger, such variations makes it impossible to predict the length of time after the first button of the exposure switch is pressed down until the system gets ready for irradiation. That is, a problem in this configuration is that the exposure start times and the reading start times cannot be determined.

To cope with the problem, it is effective to modify Step 6 to Step 11 of the above-described flow of a serial imaging process as follows. Step 1 to Step 5 and Step 12 and later are the same as those of the above-described flow. Further, the other supplementary explanations and the like in the above description are omitted.

Step 6

When the controlling apparatus 12 detects a user operation of pressing down the first button of the exposure switch (the controlling apparatus 12 receives an imaging start signal), it sends a corresponding command to the imaging apparatus 3 to notify the detection.

Step 7

When the imaging apparatus 3 receives the command, it shifts into the imaging-ready state.

Then, the imaging apparatus 3 and the controlling apparatus 12 wait for the second clocks 39, 126 to update their own second clock information to the first clock information of the clock information source apparatus 2, 4.

When the update of the clock information of the second clocks 39, 126 is completed, the imaging apparatus 3 calculates the imaging sequence start time by adding the clock information of the second clock 39 at the time of the completion to the imaging sequence waiting time stored in the storage 35. The imaging apparatus 3 stores the calculated imaging sequence start time in the storage 35 and sends it to the controlling apparatus 12.

In this example, the imaging apparatus 3 sends the imaging sequence start time to the controlling apparatus 12. Instead, the controlling apparatus 12 may calculate the imaging sequence start time by adding the clock information of the second clock 126 at the time of the completion to the imaging sequence waiting time stored in the storage 123.

The controlling apparatus 12 may then store the calculated imaging sequence start time in the storage 126 and send it to the imaging apparatus 3.

Step 8

Even after the synchronization with each other is completed, the imaging apparatus 3 and the controlling apparatus 12 continue to make a determination as to whether they are in synchronization with each other.

After the irradiation-ready signal is sent from the high voltage generator 122 to the controller 121, the imaging apparatus 3 and the controlling apparatus 12 may sometimes detect failure of the synchronization in the period of time after the completion of the synchronization between the imaging apparatus 3 and the controlling apparatus 12 until the start of reading the last frame image of the serial imaging process. In this case, the imaging apparatus 3 and the controlling apparatus 12 operate the second clocks 39, 126 in the free-running mode in the period of time after the detection until the start of reading the last frame image of the serial imaging process, and then return the operation mode to the synchronization mode. When the imaging apparatus 3 and the controlling apparatus 12 detect failure of the synchronization, they switch the operation mode to the free-running mode before updating the clock information of the second clocks 39, 126 to the clock information of the clocks 37, 125. This can prevent the clock information of the second clocks 39, 126 from being set to an abnormal value.

Step 9

When the controlling apparatus 12 receives the imaging sequence start time from the imaging apparatus 3, it stores the received imaging sequence start time in the storage 123. Then, the controlling apparatus 12 generates exposure start times of the respective frame images from the stored imaging sequence start time and the frame rate (e.g. 15 fps).

For example, the exposure start times are generated as follows. Specifically, the exposure start time of the first frame image is set to the same time as the imaging sequence start time, and the imaging cycle time (=1/frame rate) is cumulatively added thereto to obtain the exposure start times of the second and later frame images. That is, the exposure start time of the N-th frame image=the imaging sequence start time+(frame number N−1)× the imaging cycle time.

Step 10

The controller 121 sends to the high voltage generator 122 a signal representing an instruction to start exposure of a frame every time the clock information of the second irradiator clock 126 reaches any one of the exposure start times of the respective frames.

As long as the high voltage generator 122 is ready for irradiation, it controls the tube 13 to emit the radiation R for a preset irradiation time every time it receives the signal representing the instruction to start exposure. That is, the controlling apparatus 12 controls the tube 13 to emit radiation R when the clock information of the second irradiator clock 126 reaches a first predetermined value.

Step 11

When the controller 121 detects the occurrence of an event indicating the end of the imaging process, e.g. the first button of the exposure switch 15a is released, the number of frame images taken reaches the maximum number of frames stored in the storage 123, or when the controller 121 receives a shut-down notification from the high voltage generator 122 or the imaging apparatus 3, it sends a command to notify the end of the imaging process to the imaging apparatus 3 via the communicator 124 and does not send any further instruction to start exposure to the high voltage generator 122 during the current imaging process. That is, the imaging process ends.

Further, after the second button of the exposure switch is pressed down, the high voltage generator 122 has to finish a rotor-up operation of the rotating anode of the tube 13 to get ready for irradiation. However, the rotor-up time also varies depending on the conditions. When the above-described trigger (2) is used as the alternative trigger, the longest expected rotor-up time has to be set as the period of time after the second button of the exposure switch is pressed down until the system gets ready for irradiation. That is, the user has to wait for a relatively long time after the second button of the exposure switch is pressed down until the system starts taking images. This causes a problem that the system cannot start taking images at intended timing (e.g. at the maximum inspiratory level).

To cope with the problem, the flow of the serial imaging process that uses the above-described trigger (1) as the alternative trigger may be modified such that "the first button of the exposure switch" is changed to "the second button of the exposure switch".

The above-described trigger (3) may be used as the alternative trigger. In this case, when neither the first button nor the second button of the exposure switch is connected via the controlling apparatus 12 (i.e. the exposure switch is directly connected to the tube 13), a user instruction to start an imaging process is input on a UI such as the console 14, the imaging apparatus 3, the controlling apparatus 12 or the exposure switch. As in the case in which the above-described trigger (1) is used as the alternative trigger, it is impossible to predict the length of time after the user instruction until the system gets ready for irradiation. That is, a problem in this configuration is that the exposure start times and the reading start times cannot be determined.

To cope with the problem, the flow of the serial imaging process that uses the above-described trigger (1) as the alternative trigger may be modified such that "the first button of the exposure switch being pressed down" is changed to "a user instruction on a UI such as the console 14 the imaging apparatus 3, the controlling apparatus 12 or the exposure switch 15a".

Example 9-4

A problem in Example 9-3 is that white images are generated until the high voltage generator 122 and the tube 13 gets ready for irradiation. This problem can be solved by applying the configuration of Example 8-3 or the like.

Example 9-5

As described in Example 9-3, there is a problem that white images are generated until the high voltage generator 122 and the tube 13 get ready for irradiation. To cope with the problem, in Example 9-3, the determination as to whether a frame image is a white image is made based on pixels of the frame image. Instead, when the controller 121 can obtain from the high voltage generator 122 information indicating radiation is being emitted, the determination may be made based on the information.

Specifically, the radiation controller 121 has a function of obtaining the clock information of the second clock 126 at the time when the radiation controller 121 obtains the information indicating emission of radiation for the first time after the imaging sequence start time. The radiation controller 121 stores the obtained clock information in the storage 123 and sends it to the console 14 or the imaging apparatus 3.

Further, the imaging controller 31 has a function of comparing the reading start times of the frames stored in the storage 35 with the received clock information at the time of the first irradiation and deleting an unexposed frame image or prohibiting the console or the like from displaying an unexposed frame image.

This configuration eliminates the necessity of making the determination as to whether each image is a white image based on pixels of the image. This can reduce the load on the imaging apparatus 3 or the console 14 and thereby reduce the delay between taking frame images and displaying them on the console 14.

Example 9-6

As described in Example 9-3, there is a problem that white images are generated until the high voltage generator 122 and the tube 13 get ready for irradiation. To cope with the problem, in Example 9-3, the determination of whether a frame image is a white image is made based on pixels of the frame image. Instead, the imaging apparatus 3 may include a radiation sensor that can measure the dose of radiation. When the measurement value of the radiation sensor exceeds a predetermined threshold after the imaging sequence start time, the imaging apparatus 3 determines that the process of taking the first frame image is started. Then, the imaging apparatus 3 deletes the previous frame images or prohibits the previous images from being displayed.

This configuration eliminates the necessity of making the determination as to whether each image is a white image based on pixels of the image. This can reduce the load on the imaging apparatus 3 or the console 14 and thereby reduce the delay between taking frame images and displaying them on the console 14.

Example 9-7

In Example 9-6, when the radiation detection accuracy of the radiation sensor is high enough to detect the minimum accumulated dose of each frame, the measurement value of the radiation sensor can be read and compared with a threshold with respect to each frame. The sensor is reset with respect to each frame to prepare for the next frame.

However, when the radiation detection accuracy of the radiation sensor is less than the minimum accumulated dose of each frame, the sensor is not be reset with respect to each frame, but the measurement value of the accumulated dose of two or more frames is compared with a threshold. When the measurement value exceeds the threshold, it is determined that an exposure is started. In this configuration, an inexpensive radiation sensor with low detection performance can be used.

Example 9-8

It may sometimes take a long time after the first button of the exposure switch is pressed down until the second button is pressed down. In this case, when the system of Example 9-7 is configured to compare the accumulated dose of two or more frames a threshold, the radiation sensor accumulates noise since it is not reset for a long time. As a result, it may sometimes be erroneously determined that the dose exceeds the threshold.

To cope with the problem, the radiation sensor may be reset every time a predetermined time or a predetermined number of frames have elapsed.

Example 9-9

In the serial imaging process of the above-described embodiments, the number of frames exposed is equal to the number of frames read. However, some imaging systems require an unexposed frame (a frame that is only read) before the first exposed frame. For example, in order to obtain an unexposed frame image for the purpose of stabilization of the temperature in the imaging apparatus or image processing, a predetermined number (or more) of frames are not exposed but only read. Then, the subsequent frames are exposed and read.

When the configurations of the above-described embodiments are applied to such imaging systems that require unexposed frames, the control has to be suitably switched according to whether unexposed frames or exposed frames are taken. Otherwise, radiation may be erroneously emitted while unexposed frame images are taken. As a result, desired images are not obtained, and the imaging fails.

To cope with the problem, it is effective to change Step 6 to Step 16 of the above-described flow of the serial imaging process to the following Step 6 to Step 15. Step 1 to Step 5 are the same as those of the above-described flow. Further, the other supplementary explanations and the like in the above description are omitted.

Step 6

When the synchronization between the clock 37 and the clock information source apparatus 2, 4 is completed, the imaging apparatus 3 shifts into an imaging-ready state.

Then, the imaging apparatus 3 and the controlling apparatus 12 wait for the second clocks 39, 126 to update their own second clock information to the first clock information of the clock information source apparatus 2, 4.

If the update of the clock information is not completed within a predetermined time, the console 14 may be informed of failure of the synchronization. The console 14 may then display a message or the like on a display (not shown) to inform the failure of the synchronization, to prompt the user to perform troubleshooting such as restart of the clock information source apparatus 2, 4 and checking the network configuration, or to recommend using a wired connection to take an image. This can speed up recovery from an abnormality.

When the update of both the clock information of the second clocks 39, 126 is completed, the imaging apparatus 3 calculates an imaging sequence start time by adding an imaging sequence waiting time stored in the storage 35 to the clock information of the second clock 39 at the time of the completion. The imaging apparatus 3 stores the calculated imaging sequence start time in the storage 35 and sends it to the controlling apparatus 12.

In this example, the imaging apparatus 3 sends the imaging sequence start time to the controlling apparatus 12. Instead, the controlling apparatus 12 may calculate the imaging sequence start time by adding the clock information of the second clock 126 at the time of the completion to the imaging sequence waiting time stored in the storage 123. The controlling apparatus 12 may store the calculated imaging sequence start time in the storage 126 and sends it to the imaging apparatus 3.

Step 7

Even after the synchronization with each other is completed, the imaging apparatus 3 and the controlling apparatus 12 continue to make a determination as to whether they are in synchronization with each other.

When the imaging apparatus 3 and the controlling apparatus 12 detect failure of the synchronization in the period of time after the completion of the synchronization of both the imaging apparatus 3 and the controlling apparatus 12 in the imaging-ready state until the start of reading the last frame of the serial imaging process, they operate the second clocks

39, 126 in the free-running mode in the period of time after the detection until the start of reading the last frame of the serial imaging process. Then, they return the operation mode to the synchronization mode.

Step 8

The imaging apparatus 3 generates reading start times of the respective frames based on the imaging sequence start time stored in the storage 123, the frame rate and the accumulation time of each frame image.

In order to avoid emitting radiation in a reading operation, the accumulation time is longer than the irradiation time of each frame.

Step 9

When the controlling apparatus 12 receives the imaging sequence start time from the imaging apparatus 3, it stores the received imaging sequence start time in the storage 123. Then, the controlling apparatus 12 generates exposure start times of the respective frames from the stored imaging sequence start time and the frame rate (e.g. 15 fps).

Step 10

The imaging apparatus 3 starts reading charges accumulated in the radiation detector 32 to generate image data of a frame image every time the clock information of the second imager clock 39 reaches any one of the reading start times of the respective frames. When the imaging apparatus 3 has finished reading frames that are necessary for warming up (or when the imaging apparatus 3 has finished obtaining unexposed frame images that are necessary for image processing), it gives to the controlling apparatus 12 a notification that imaging is allowed. Even after giving the notification of allowance of exposure, the imaging apparatus 3 starts reading charges accumulated in the radiation detector 32 to generate image data of a frame image every time the clock information of the second imager clock 39 reaches any one of the reading start times of the respective frames.

Step 11

When the controller 121 of the controlling apparatus 12 detects a user operation of pressing down the second button of the exposure switch 15*a* (the controller 121 receives the imaging start signal), it sends a corresponding signal to the high voltage generator 122 and shifts into a stand-by state to wait for the ready signal from the high voltage generator 122. The ready signal represents that the high voltage generator 122 is ready for irradiation.

When the high voltage generator 122 receives the imaging start signal, it starts preparation for irradiation. Specifically, the high voltage generator 122 prepares a voltage and a current to be output to the tube 13 and instructs the tube 13 to start rotation of a rotating anode.

Step 12

The controller 121 does not instruct the high voltage generator 122 to start exposure until it receives both the irradiation-ready signal from the high voltage generator 122 and the notification of allowance of exposure from the imaging apparatus. When the controller 121 receives both signals, it sends a communication command to the imaging apparatus so as to give an irradiation-ready notification. Thereafter, the controller 121 sends to the high voltage generator 122 a signal representing an instruction to start exposure every time the clock information of the second irradiator clock 126 reaches any one of the exposure start times of the respective frames.

The high voltage generator 122 controls the tube 13 to emit the radiation R for a preset irradiation time every time it receives the signal representing the instruction to start exposure. That is, the controlling apparatus 12 controls the tube 13 to emit the radiation R when the clock information of the second irradiator clock 126 reaches a first predetermined value.

Step 13

When the controller 121 detects the occurrence of an event indicating the end of the imaging process, e.g. the second button of the exposure switch 15*a* is released, the number of frame images taken reaches the maximum number of frames stored in the storage 123, or the controller 121 receives a shut-down notification from the high voltage generator 122 or the imaging apparatus 3, it sends a command to notify the completion of the imaging process to the imaging apparatus 3 via the communicator 124 and does not send any further instruction to start exposure to the high voltage generator 122 during the current imaging process. That is, the imaging process ends.

The maximum number of frames may be a fixed value stored in the storage 123. Alternatively, the maximum number of frames may be a value that is input on the console 14 by the user, which is sent to the controlling apparatus 12 and stored in the storage 123.

Step 14

After receiving the irradiation-ready signal from the controlling apparatus 12, the imaging apparatus 3 starts reading charges accumulated in the radiation detector 32 to generate image data of a frame image every time the clock information of the second imager clock 39 reaches any one of the reading start times of the respective frames.

Step 15

Then, the imaging apparatus 3 terminates the imaging process when it detects the occurrence of an event indicating the end of the imaging process, e.g. the imaging apparatus 3 receives from the controlling apparatus 12 a command that notifies the completion of the imaging process, or the number of frame images taken reaches the maximum number of frames stored in the storage 35.

Example 10-1

In the above-described embodiments, the controlling apparatus 12A and the imaging apparatus 3 are connected in a wireless manner to perform a serial imaging process. However, when the imaging apparatus 3 is also connected in a wired manner, it is preferred to switch to a method that is less likely to be affected by a decrease of the accuracy of the second imager clock 39 and the error of the frequency of the oscillators of the imaging apparatus 3 and the controlling apparatus 12.

Specifically, the irradiation controlling apparatus 12 generates the exposure start times and the reading start times. The controlling apparatus 12 sends the reading start times to the imaging apparatus 3 though a dedicated line and instructs the tube 13 to emit a radiation at the exposure start times of the respective frames.

Then the imaging apparatus 3 starts reading operations at the reading start times of the respective frames.

The imaging apparatus 3 may have a function of detecting the connection status. When the imaging apparatus 3 detects a wired connection through a cable, it may select the wired serial imaging method as described in this example. When the imaging apparatus 3 determines that there is no wired connection through a cable, it may select the previously-described serial imaging method.

This can reduce user operations and thereby improve the usability.

Example 10-2

The above-described embodiments are intended for wireless serial imaging. However, the number of frames may be set to one. That is, the same control can also be used for wireless still imaging. By using the same control, it is possible to reduce the development cost.

When a wireless still imaging process is performed, the imaging method may be switched to a method that is less likely to be affected a decrease of the accuracy of the clocks and the frequency error of the oscillators of the imaging apparatus 3 and the controlling apparatus 12 (e.g. SRM imaging by AERO-DR, AERO-SYNC imaging or the like) so that the wireless still imaging process can be performed stably.

Further, the console 14 may have a function of switching the imaging method of the imaging apparatus 3 and the controlling apparatus 12 according to whether the user selects wireless still imaging or wireless serial imaging. This can reduce user operations and thereby improve the usability.

Example 11-1

The dynamic change of a radiographic image may be displayed along with the dynamic change of biological information, or the relationship between them may be analyzed, so that the user can understand the condition of the subject S in more detail.

For example, a dynamic image of the chest of the subject S may be taken with a pulse oximeter attached on the subject S. Then, information such as the arterial oxygen saturation (SpO2) and the pulse rate can be obtained from the pulse oximeter while information on the lung ventilation function can be obtained from the dynamic image. By integrally analyzing the information, it is possible to estimate the temporal change of the respiratory function.

However, devices for measuring biological information such as a pulse oximeter are normally independent from a radiographic system, and their operation is based on their individual oscillators. Accordingly, a time difference of the clock information occurs. When each of a device and a radiographic system includes an oscillator with a frequency allowable variation of ±100 ppm, the maximum difference that can occur in one hour is 720 ms (60 sec×60 min× ±0.01%=±360 ms, when the error of one clock is +360 ms while the error of the other clock is −360 ms). In this case, when a dynamic image is taken at 30 fps one hour after the clock information of the clocks are correctly synchronized with each other, the time difference between the dynamic image and the biological information can be approximately 22 frames at the maximum. Such data is not suitable for displaying or analyzing a biological function on a frame basis.

Figure 56:
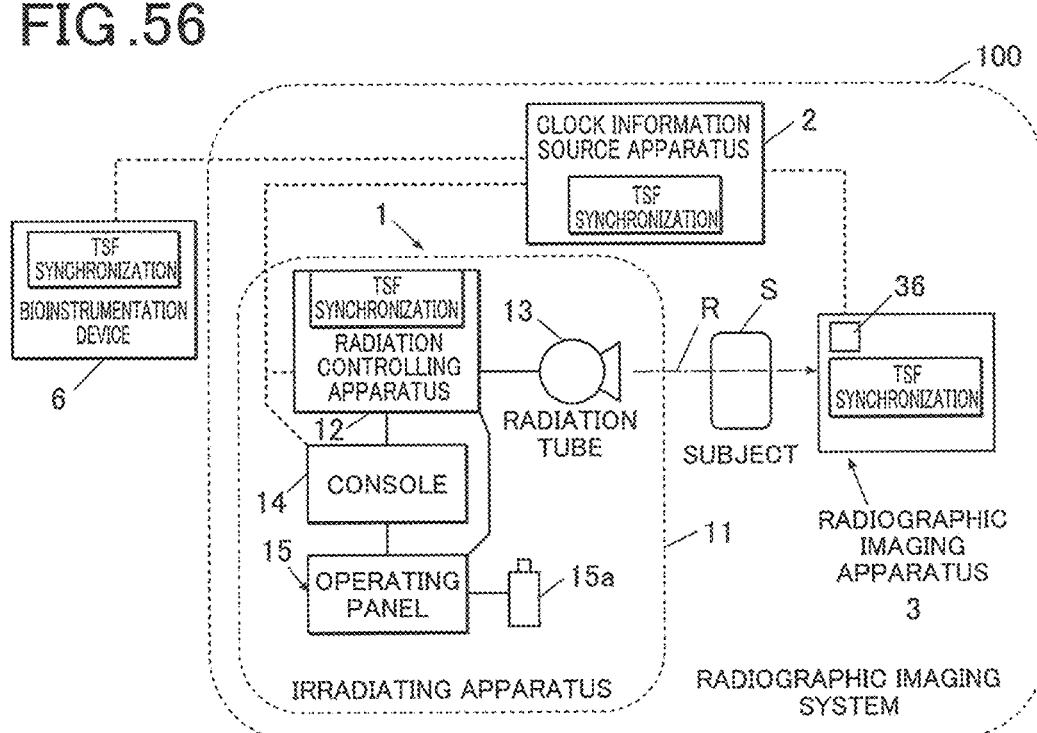
FIG. 56 is a block diagram of the radiographic imaging system according to Example 11-1, illustrating the configuration thereof.

Nowadays a variety of devices have a wireless LAN communication function. In the above-described embodiments, a bioinstrumentation device 6 may be connected to the clock information source apparatus 2, 4 as illustrated in FIG. 56, and the imaging system 100 and the bioinstrumentation device 6 may be synchronized with each other based on the first clock information of the clock information source apparatus 2, 4

Specifically, the imaging system 100 has a function of associating corresponding clock times with frame images when storing the frame images. For example, each frame image is associated with the exposure start time, the exposure end time or the reading start time (a time stamp) of the frame.

The bioinstrumentation device 6 has a function of associating the clock information at the time of sampling biological information with each sampling value when storing the sampling value.

The image data of the radiographic image and the biological information are sent to an apparatus that integrally analyze and display the radiographic image and the biological information, so that the frame images and the sampling values are displayed in synchronization with each other according to the associated clock information. That is, it is possible to display the temporal change of both the frame image and the biological information without any time difference between them.

Further, in addition to display them, it is also possible to use the clock information to understand what biological changes occurred at the same time.

In addition to the clock information source apparatus 2, 4 and the bioinstrumentation device 6, a third device and more may be further connected.

Instead of wireless LAN, the synchronization may be performed according to IEEE1588 or NTP or by using an atomic clock.

The frequency band of wireless LAN may be selectable. In this configuration, for example, when the bioinstrumentation device 6 (pulse oximeter or the like) to be connected supports only 2.4 GHz WLAN, the frequency band of the wireless LAN of the imaging system 100 can be set to 2.4 GHz.

A list of devices that are potentially connected to the imaging system 100 may be prestored in the console 14 or the like along with the available frequency range thereof. When a device is connected to the console 14 via the clock information source apparatus 2, 4, the console 14 references the stored list and changes the frequency range of the imaging apparatus 3 and the controlling apparatus 12. This can eliminate the necessity of checking the frequency range or a user operation for switching the frequency range and thereby improve the usability.

When the TSF is used, the synchronization can be performed to an accuracy of tens to hundreds of microseconds. In this case, for example, when a dynamic image is taken at 30 fps, i.e. the imaging cycle is 33.3 ms, the time difference can be reduced to less than a single frame. Accordingly, radiographic frame images can be associated with sampling values of biological information based on time with respect to each frame. Therefore, the images and the sampling values can be displayed and analyzed with higher accuracy.

Example 11-2

As described in Example 11-1, there is a problem that a time difference of the clock information occurs since the bioinstrumentation device and the radiographic system are normally independent from each other and the operation thereof is based on the individual oscillators. To cope with the problem, in Example 11-1, the bioinstrumentation device is connected to the clock information source apparatus 2, 4. Further, the TSF may be used to perform the synchronization. However, some wireless LAN modules cannot use the TSF to read clock information from an external device.

When the bioinstrumentation device uses such a wireless LAN module, it is required to modify or replace the wireless LAN module or to correct the hardware. This requires long development time and high cost.

In such cases, it is possible to select a more common synchronization method that can be implemented in a software, such as IEEE 1588 or NTP. However, when the NTP is used for controlling the timing of exposure and reading in a radiographic serial imaging process, the insufficient time accuracy sometimes causes an imaging failure.

When the system and the device use different synchronization methods, e.g. one uses the NTP while the other uses the TSF of WLAN, the image cannot be displayed or analyzed in synchronization with the measurement result due to the difference in definition of time stamp values.

Figure 57:
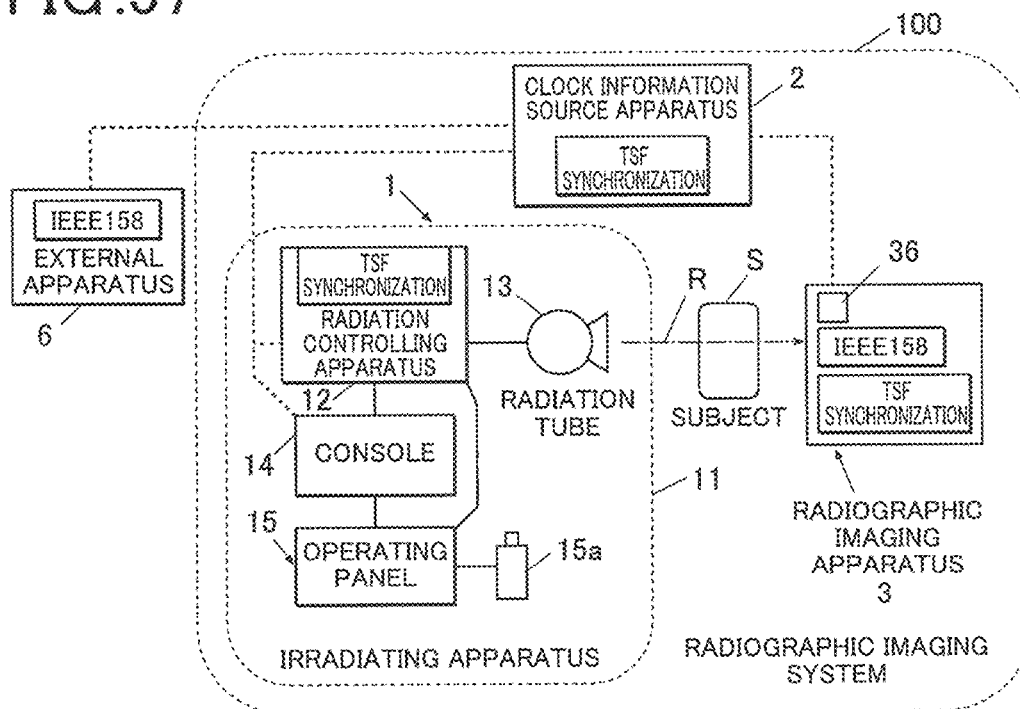
FIG. 57 is a block diagram of the radiographic imaging system according to Example 11-2, illustrating the configuration thereof.

To cope with the problem, in the above-described embodiments, two synchronization methods may be used in parallel as illustrated in FIG. 57.

Specifically, the imaging system 100, which requires accurate time management for the control, uses an accurate time synchronization method (the TSF of WLAN or the like) to perform the synchronization. However, the imaging system 100 uses a normal time synchronization method to add a time stamp to an output such as a frame image.

On the other hand, the bioinstrumentation device 6 (e.g. a pulse oximeter or the like), which does not require accurate time management for the control, uses the normal time synchronization method to add a time stamp to an output such as heart rate.

In this configuration, frame images taken by the imaging system 100 can be associated with sampling values measured by an external device such as the bioinstrumentation device 6 based on time without any modification of the hardware of the bioinstrumentation device 6.

Example 11-3

As described in Example 11-1, there is a problem that a time difference of the clock information occurs since the bioinstrumentation device and the radiographic system are normally independent from each other and the operation thereof is based on the individual oscillators. To cope with the problem, in Example 11-1, the bioinstrumentation device is connected to the clock information source apparatus 2, 4. However, when the bioinstrumentation device to be synchronized is not predetermined, the synchronization method that the bioinstrumentation device can use cannot be specified. A problem in this case that the reference time of time stamps to be used in the imaging system cannot be determined.

Figure 58:
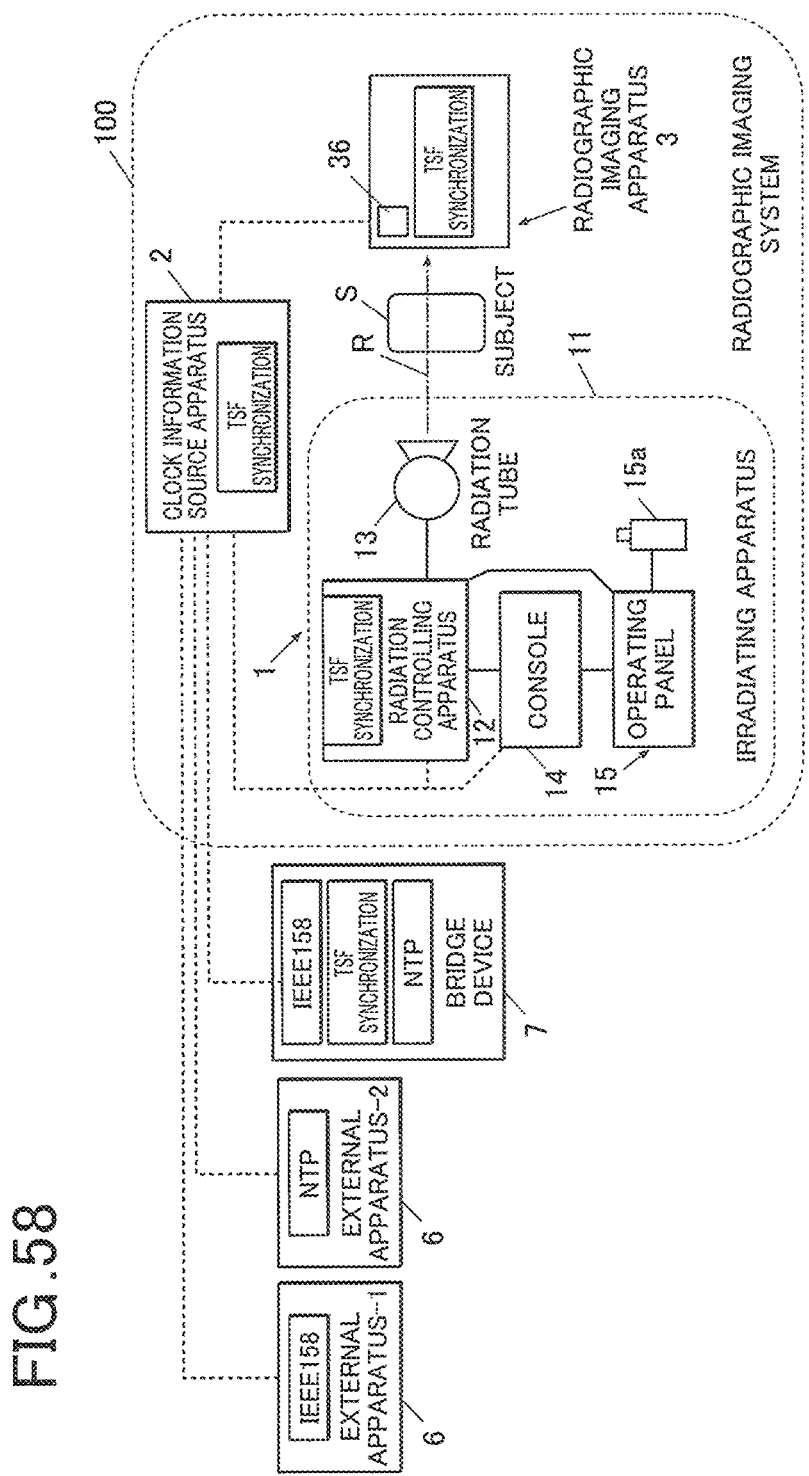
FIG. 58 is a block diagram of the radiographic imaging system according to Example 11-3, illustrating the configuration thereof.

To cope with the problem, in the above-described embodiments, the system may be connected to a bridge device 7 that correlates different reference times with each other as illustrated in FIG. 58.

The bioinstrumentation device 6 and the imaging system add time stamps to images or measurement results based on the respective reference times.

For example, the bridge device 7 is synchronized according to the TSF, the NTP and IEEE 1588 and stores a list of combinations of the respective reference times (e.g. adds a combination of the three reference times to the list at 10 msec intervals).

Modalities send measurement results with time stamps to the bridge device 7, and the bridge device 7 converts the time stamps based on a certain reference time and sends them to the console.

Alternatively, modalities send measurement results to the console 14, and the console makes an inquiry to the bridge device.

With this configuration, it is possible to build an imaging system that can associate measurement results of two or more devices based on time even when the bioinstrumentation device 6 to be connected is not predetermined.

Example 12

In the above-described embodiments, the frame rate may be changeable. In such cases, since the amount of dark charges in a frame image varies depending on the frame rate, a correction table to be used for the correction has to be changed according to the frame rate.

It is desired that the system is configured to be able to display the frame images read by the imaging apparatus 3 on the console 14 with as short delay as possible. This allows the user to find the abnormal position of the subject S or the like early in the imaging period to cancel or restart the imaging process so as to reduce the exposure.

When the frame rate is variable, the imaging apparatus 3 can be configured to select and read a correction table in the storage 35 according to the frame rate to perform the correction. However, a problem in this configuration is that the imaging apparatus 3 takes a long time for the processing, which increases the delay of displaying an image on the console 14.

To cope with the problem, in the above-described embodiments, the imaging apparatus 3 may associate information (time stamp) indicating the time interval between temporally adjacent frame images to each frame image when storing the frame image.

For example, the imaging apparatus 3 stores each frame image along with the reading start time (synchronization clock information) or the reading end time (synchronization clock information) of the frame image.

The imaging apparatus 3 does not perform the correction according to the frame rate but only adds time stamps to frame images and sends them to the console 14.

Based on the received time stamps, the console 14 determines the time intervals between the frame images and sequentially display the frame images at the determined time intervals. The images thus displayed are not corrected by image processing but has quality sufficient to make a determination as to whether images have to be retaken again.

After displaying the images (or in parallel to displaying images when the CPU has sufficient processing power), the console 14 selects a correction table according to the determined time intervals between frame images and performs the correction.

This configuration can minimize the amount of processing performed by the imaging apparatus 3, and the frame images read by the imaging apparatus 3 can be displayed on the console 14 without delay. This allows the user to find the abnormal position of the subject S early in the imaging period to cancel or restart the imaging process so as to reduce the exposure of the subject S.

In the above-described embodiments and examples, the clock information source apparatus 2, 4 is connected to both the controlling apparatus 12, 2A and the console 14. However, the present invention is not limited to this connection. For example, the clock information source apparatus 2, 4 may be connected only to the radiation controlling apparatus 12, 12A, or the clock information source apparatus 2, 4 may be connected only to the console 14.

Since the irradiating apparatus 1 is provided to emit radiation, the timing of emitting radiation can be controlled more accurately when the controlling apparatus 12, 12A is directly connected to the clock information source apparatus 2, 4.

On the other hand, since the console 14 is provided to control the overall imaging system 100, the console 14 can perform the synchronization check or the like more efficiently when the console 14 is directly connected to the clock information source apparatus 2, 4.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent applications No. 2018-056477 and No. 2018-056482, both filed on Mar. 23, 2018, are incorporated herein by reference in their entirety.

What is claimed is:

1. A radiographic imaging system, comprising:
an irradiating apparatus which generates radiation;
a first clock which keeps time and which works with the irradiating apparatus;
a radiographic imaging apparatus which generates image data based on received radiation,
wherein the radiographic imaging apparatus comprises a second clock which keeps time; and
a hardware processor,
wherein the hardware processor
(i) obtains a clock value of the first clock at a predetermined time point and a clock value of the second clock at the predetermined time point respectively as first clock information and second clock information,
(ii) makes a determination as to whether a specific condition is met based on the obtained first clock information and the obtained second clock information, and
(iii) in response to the specific condition being met, performs a specific output.

2. The radiographic imaging system according to claim 1, wherein as the specific output, the hardware processor performs a correction to bring the clock value of at least one of the first clock and the second clock closer to the clock value of another of the first clock and the second clock.

3. The radiographic imaging system according to claim 2, wherein the hardware processor performs the correction to bring the clock value of one of the first clock and the second clock closer to the clock value of the other of the first clock and the second clock before the irradiating apparatus generates the radiation.

4. The radiographic imaging system according to claim 3, wherein the hardware processor performs the specific output in response to determining that the specific condition is met in an imaging period after performing the correction.

5. The radiographic imaging system according to claim 1, wherein the hardware processor determines that the specific condition is met when a difference between the first clock information and the second clock information exceeds a specific value.

6. The radiographic imaging system according to claim 1, wherein the hardware processor
obtains the first clock information and the second clock information at predetermined time points in a specific period of time,
calculates differences between the obtained first clock information and the obtained second clock information, and
determines that the specific condition is met when an average of the calculated differences exceeds a specific value.

7. The radiographic imaging system according to claim 1, wherein the hardware processor
obtains the first clock information and the second clock information at predetermined time points in a specific period of time,
calculates a difference between the first clock information and the second clock information every time the hardware processor obtains the first clock information and the second clock information,
calculates an amount of change between the calculated difference and a previously calculated difference, and
determines that the specific condition is met when the calculated amount of change exceeds a previously calculated amount of change.

8. The radiographic imaging system according to claim 1, wherein as the specific output, the hardware processor corrects the clock information of one of the first clock and the second clock by a certain ratio or a certain amount with reference to another of the first clock and the second clock so that the clock information of one clock is closer to the clock information of the other clock.

9. The radiographic imaging system according to claim 1, wherein as the specific output, the hardware processor corrects the clock information of one of the first clock and the second clock with reference to another of the first clock and the second clock so that the clock information of one clock is closer to the clock information of the other clock.

10. The radiographic imaging system according to claim 1, wherein as the specific output, the hardware processor stops operation of at least one of generation of the radiation by the irradiating apparatus and generation of the image data by the radiographic imaging apparatus.

* * * * *